US012601725B2

(12) United States Patent
Beckler et al.

(10) Patent No.: US 12,601,725 B2
(45) Date of Patent: Apr. 14, 2026

(54) LONG-TERM BENTHIC INCUBATION AND MEASURING SYSTEM AND METHOD

(71) Applicant: FLORIDA ATLANTIC UNIVERSITY BOARD OF TRUSTEES, Boca Raton, FL (US)

(72) Inventors: Jordon Beckler, Ft. Pierce, FL (US); Csaba Vaczo, Ft. Pierce, FL (US)

(73) Assignee: FLORIDA ATLANTIC UNIVERSITY BOARD OF TRUSTEES, Boca Raton, FL (US)

( * ) Notice: Subject to any disclaimer, the term of this patent is extended or adjusted under 35 U.S.C. 154(b) by 294 days.

(21) Appl. No.: 18/405,523

(22) Filed: Jan. 5, 2024

(65) Prior Publication Data

US 2024/0230613 A1      Jul. 11, 2024

Related U.S. Application Data

(60) Provisional application No. 63/478,580, filed on Jan. 5, 2023.

(51) Int. Cl.
G01N 33/18 (2006.01)
G01N 1/02 (2006.01)
(Continued)

(52) U.S. Cl.
CPC .............. G01N 33/18 (2013.01); G01N 1/14 (2013.01); G01N 1/38 (2013.01); G01N 35/1081 (2013.01);
(Continued)

(58) Field of Classification Search
CPC .. G01N 33/18; G01N 2001/1031; G01N 1/14; G01N 1/38; G01N 35/1081;
(Continued)

(56) References Cited

U.S. PATENT DOCUMENTS 5,473,952 A * 12/1995 Lieberman ............... G01N 1/12
73/864.31
7,856,899 B2 12/2010 Furtaw et al.
(Continued)

OTHER PUBLICATIONS

Tengberg, A., F. De Bovee, P. Hall, W. Berelson, D. Chadwick, G. Ciceri, P. Crassous, A. Devol, S. Emerson, J. Gage, R. Glud, F. Graziottini, J. Gundersen, D. Hammond, W. Helder, K. Hinga, O. Holby, R. Jahnke, A. Khripounoff, S. Lieberman, V. Nuppenau, O. Pfannkuchen. Reimers, G. Rowe, A. Sahami, F. Sayles, M. Schurter, D. Smallman, B. Wehrli and P. De Wilde (1995). "Benthic chamber and profiling landers in oceanography—A review of design, technical solutions and functioning." Progress in Oceanography 35(3): 253-294.

(Continued)

*Primary Examiner* — Thomas M Hammond, III
(74) *Attorney, Agent, or Firm* — Meunier Carlin & Curfman LLC

(57) ABSTRACT

The exemplary system and method configured to perform benthic flux incubation and measurement in an on-going continuous manner via motorized or non-motorized actuators that moves one or more sampling chambers (i) between different sampling regions or (ii) maintains the sampling chamber over a single region, for long term repeated measurements. The exemplary system and method can incubate and sample over multiple benthic sampling regions to acquire repeated measurements of both (i) fluxes and (ii) background processes and conditions (e.g., via ambient water incubations or ambient water concentration measurements), the results of which can be combined and processed by the exemplary system to generate data requiring minimal post-processing.

21 Claims, 18 Drawing Sheets

(51) Int. Cl.
| | |
|---|---|
| *G01N 1/10* | (2006.01) |
| *G01N 1/14* | (2006.01) |
| *G01N 1/38* | (2006.01) |
| *G01N 35/10* | (2006.01) |

(52) U.S. Cl.
CPC ............... *G01N 2001/021* (2013.01); *G01N 2001/1025* (2013.01); *G01N 2001/1031* (2013.01); *G01N 2001/1418* (2013.01); *G01N 2001/388* (2013.01)

(58) Field of Classification Search
CPC ..... G01N 2001/021; G01N 2001/1025; G01N 2001/1418; G01N 2001/388; G01N 1/20; G01N 33/1886
See application file for complete search history.

(56) References Cited

U.S. PATENT DOCUMENTS

2019/0368978 A1* 12/2019 Sheryll ................... E21B 7/124
2023/0354785 A1* 11/2023 Mcmanamay ........... G01N 1/20

OTHER PUBLICATIONS

Kononets, M., A. Tengberg, M. Nilsson, N. Ekeroth, A. Hylen, E. K. Robertson, S. Van De Velde, S. Bonaglia, T. Rütting, S. Blomqvist and P. O. J. Hall (2021). "In situ incubations with the Gothenburg benthic chamber landers: Applications and quality control." Journal of Marine Systems 214: 103475.

Orcutt, B. N., L. L. Lapham, J. Delaney, N. Sarode, K. S. Marshall, K. J. Whaley-Martin, G. Slater, C. G. Wheat and P. R. Girguis (2017). "Microbial response to oil enrichment in Gulf of Mexico sediment measured using a novel long-term benthic lander system." Elementa: Science of the Anthropocene 5:18.

Friedl, G., C. Dinkel and B. Wehrli (1998). "Benthic fluxes of nutrients in the northwestern Black Sea." Marine Chemistry 62(1-2): 77-88.

Berelson, W., J. McManus, K. Coale, K. Johnson, D. Burdige, T. Kilgore, D. Colodner, F. Chavez, R. Kudela and J. Boucher (2003). "A time series of benthic flux measurements from Monterey Bay, CA." Continental Shelf Research 23(5): 457-481.

Long, M. H. (2021). "Aquatic Biogeochemical Eddy Covariance Fluxes in the Presence of Waves." Journal of Geophysical Research: Oceans 126(2).

Johnson, K. S., J. P. Barry, L. J. Coletti, S. E. Fitzwater, H. W. Jannasch and C. F. Lovera (2011). "Nitrate and oxygen flux across the sediment-water interface observed by eddy correlation measurements on the open continental shelf." Limnology and Oceanography Methods 9(11):543-553.

Pamatmat, M. M. and D. Fenton (1968). "An Instrument for Measuring Subtidal Benthic Metabolism in Situ 1." Limnology and Oceanography 13(3): 537-540.

Berelson, W. M. and D. E. Hammond (1986). "The calibration of a new free-vehicle benthic flux chamber for use in the deep sea." Deep Sea Research Part A. Oceanographic Research Papers 33(10): 1439-1454.

Jahnke, R. A. and M. B. Christiansen (1989). "A free-vehicle benthic chamber instrument for sea floor studies." Deep Sea Research Part A. Oceanographic Research Papers 36(4): 625-637.

Tengberg, A., P. O. J. Hall, U. Andersson, B. Lindén, O. Styrenius, G. Boland, F. de Bovee, B. Carlsson, S. Ceradini, A. Devol, G.

Duineveld, J. U. Friemann, R. N. Glud, A. Khripounoff, J. Leather, P. Linke, L. Lund-Hansen, G. Rowe, P. Santschi, P. de Wilde and U. Witte (2005). "Intercalibration of benthic flux chambers." Marine Chemistry 94(1-4): 147-173.

Sommer, S., J. Gier, T. Treude, U. Lomnitz, M. Dengler, J. Cardich and A. W. Dale (2016). "Depletion of oxygen, nitrate and nitrite in the Peruvian oxygen minimum zone cause an imbalance of benthic nitrogen fluxes." Deep Sea Research Part I: Oceanographic Research Papers 112: 113-122.

Morse, J. W., G. Boland and G. T. Rowe (1999). "A 'gilled' benthic chamber for extended measurement of sediment-water fluxes." Marine Chemistry 66: 255-230.

Sommer, S., M. Türk, S. Kriwanek and O. Pfannkuche (2008). "Gas exchange system for extended in situ benthic chamber flux measurements under controlled oxygen conditions: First application-Sea bed methane emission measurements at Captain Arutyunov mud volcano." Limnology and Oceanography: Methods 6(1): 23-33.

Spagnoli, F., P. Penna, G. Giuliani, L. Masini and V. Martinotti (2019). "The AMERIGO Lander and the Automatic Benthic Chamber (CBA): Two New Instruments to Measure Benthic Fluxes of Dissolved Chemical Species." Sensors (Basel) 19(11).

Sayles, F. L. and W. H. Dickinson (1991). "The ROLAI2D lander: A benthic lander for the study of exchange across the sediment-water interface." Deep Sea Research Part A. Oceanographic Research Papers 38(5): 505-529.

Nielsen, L. P. and R. N. Glud (1996)."Denitrification in a coastal sediment measured in situ by the nitrogen isotope pairing technique applied to a benthic flux camber." Marine Ecology Progress Series 137: 181-186.

Jouffray, J.-B., R. Blasiak, A. V. Norström, H. Österblom and M. Nyström (2020). "The Blue Acceleration: The Trajectory of Human Expansion into the Ocean." One Earth 2(1): 43-54.

Apitz, S. E. (2012). "Conceptualizing the role of sediment in sustaining ecosystem services: Sediment-ecosystem regional assessment (SEcoRA)." Sci Total Environ 415: 9-30.

Haffert, L., M. Haeckel, H. de Stigter and F. Janssen (2020). "Assessing the temporal scale of deep sea mining impacts on sediment biogeochemistry." Biogeosciences 17(10): 2767-2789.

Jahnke, R. A., J. R. Nelson, R. L. Marinelli and J. E. Eckman (2000). "Benthic flux of biogenic elements on the Southeastern US continental shelf: influence of pore water advective transport and benthic microalgae." Continental Shelf Research 20(1): 109-127.

Glazer, B. T., A. G. Marsh, K. Stierhoff and G. W. Luther (2004). "The dynamic response of optical oxygen sensors and voltametric electrodes to temporal changes in dissolved oxygen concentrations." Analytica Chimica Acta 518(1-2): 93-100.

Meiggs, D. and M. Taillefert (2011). "The effect of riverine discharge on biogeochemical processes in estuarine sediments." Limnology and Oceanography 56(5):1797-1810.

Mahmud, M. A. P., F. Ejeian, S. Azadi, M. Myers, B. Pejcic, R. Abbassi, A. Razmjou and M. Asadnia (2020). "Recent progress in sensing nitrate, nitrite, phosphate, and ammonium in aquatic environment." Chemosphere 259.

Niemisto, J., Kononets, M., Ekeroth, N., Tallberg, P., Tengberg, A., Hall, P.O.J., Benthic fluxes of oxygen and inorganic nutrients in the archipelago of gulf of Finland, Baltic Sea—effects of sediment resuspension measured in situ. J. Sea Res. 135, 95-106, 2018.

Coogan, J., Rheuban, J.E. and Long, M.H. (2022), Evaluating benthic flux measurements from a gradient flux system. Limnol Oceanogr Methods, 20: 222-232. https://doi.org/10.1002/lom3.10482. Abstract.

\* cited by examiner

Buoyed shallow water deployment (< 200 m)

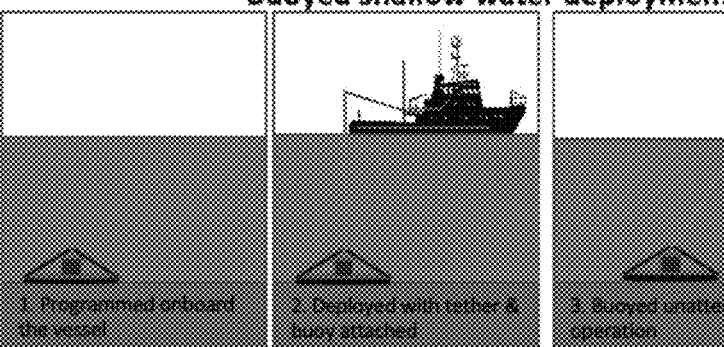
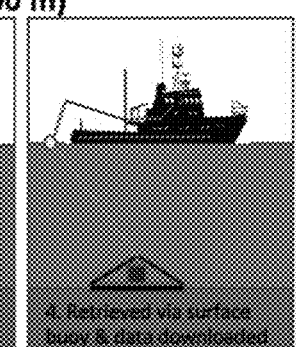

Free-vehicle deep version (6,000 m possible with modifications )

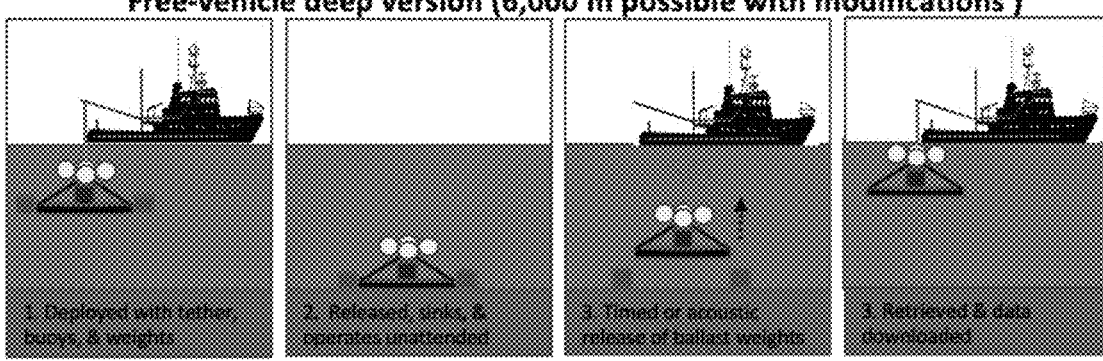

Ocean Observing Network: Autonomous Vehicle retrieval

Ocean Observing Network: Permanent installation, sensors on CAROSEL

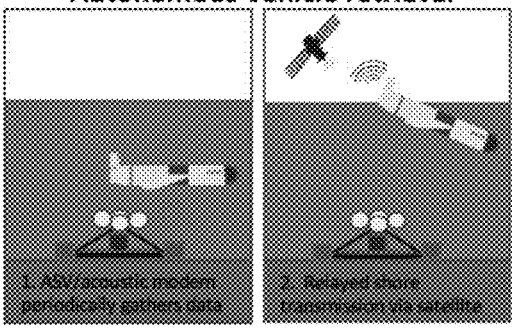
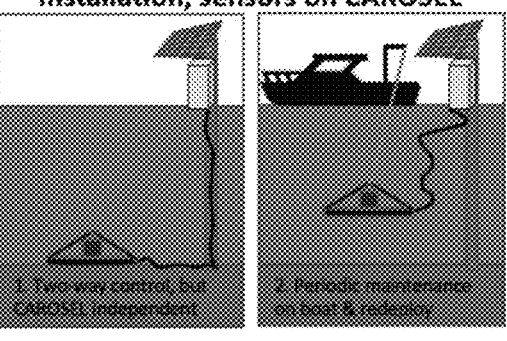

Ocean Observing Network: Augmenting existing sensor suite with benthic flux monitoring capabilities (CAROSEL serves as sampling interface)

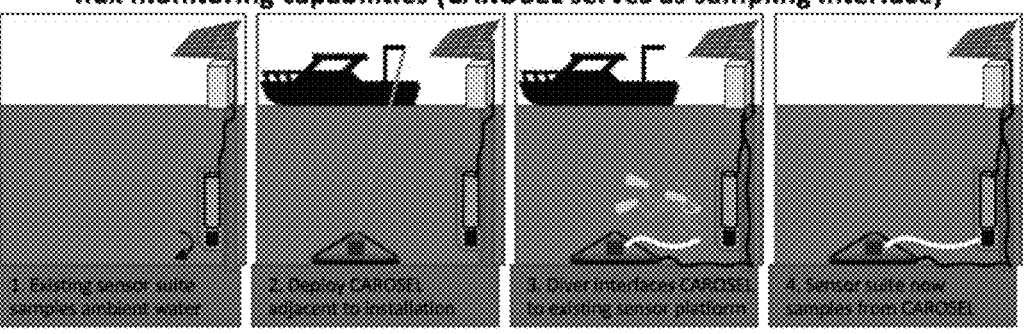

*FIG. 4A*

SITE SELECTION

620

RAW DATA TIME SERIES: Site L001

◌ Benthic incubation (porthole #)    ◯ Water column

● Ambient water incubation (porthole #)

6/19/24    <Date/time slider>    6/20/24

00:00                    16:00

*632*

Raw Data time series variable   +  -

*634*

DERIVED INFORMATION: L001

Water depth and Dissolved Inorganic Nitrogen

Site L001 Water Column DIN turnover
times with respect to Site L001 sediment
fluxes or Kissimmee River fluxes <Date/time slider>
652

Derived information variable
654

LONG-TERM BENTHIC INCUBATION AND MEASURING SYSTEM AND METHOD

CROSS-REFERENCE TO RELATED APPLICATIONS

This application claims priority to, and the benefit of, U.S. Provisional Patent Application 63/478,580, filed Jan. 5, 2023, which is incorporated herein by reference in its entirety.

TECHNICAL FIELD

This disclosure relates to the testing of seabed sediment and, more particularly, to devices for sampling and analyzing sedimentary environments on site, particularly at the benthic zone.

BACKGROUND

In situ analyses of sedimentary environments have numerous advantages over other techniques, such as sediment coring and lab analyses, including improved sampling resolution, cost savings on labor, and the reduction of sampling artifacts (i.e., changes to the natural system). In the field of chemical oceanography, both direct chemical concentrations and material fluxes are the two most common types of measurements.

Benthic flux research has been driven by ocean processes that occur on longer timescales than terrestrial or estuarine aquatic ecosystems, so discrete "one-off" measurements often do not suffice. Benthic flux chamber incubation devices are generally configured for single use, often having a single chamber that is deployed to a benthic region to conduct the monitoring of, for example, dissolved oxygen, carbon, and nutrient budgets. The system can then be retrieved onboard a research vessel to be redeployed at a new location.

There is a benefit to improving the benthic flux chamber incubation devices and measurement techniques of the sea floor.

SUMMARY

An exemplary system and method are disclosed for benthic flux incubation and measurement in an on-going continuous manner via motorized or non-motorized actuators that move one or more sampling chambers (i) between different sampling regions or (ii) maintain the sampling chamber over a single region, for long term repeated measurements. That is, the sampling chamber can be positioned via the actuators at a given sampling location to incubate and sample via a pre-defined sampling protocol over a period of time before being repositioned to another sampling location located near the current sampling location. Of course, the sampling chamber can be autonomously actuated to reset the contents of the sampling system and re-perform the incubation and sampling over the same sampling location.

The exemplary system and method can incubate and sample over multiple benthic sampling regions to acquire repeated measurements of both (i) benthic fluxes and (ii) background conditions and processes (e.g., via ambient water concentration measurements or incubations, respectively), the results of which can be combined and processed by the exemplary system to generate data requiring minimal post-processing. The background conditions and processes (e.g., inferred from ambient water concentration measurements or ambient water incubations) can also be presented to provide a contextual reference or baseline measurements for the benthic flux incubation measurement. Uniquely, this versatility can be obtained by employing only a single common sensor suite and a single shared benthic chamber. Examples include measures of "true" sediment flux and turnover time that can be used to monitor or direct treatment of a body of water.

The exemplary system is configured, preferably, to be modular to be re-configurable for different sampling applications (i.e., interchangeable sensor combination sets) and readily deployable to incubate and acquire measurements over the same or multiple benthic sampling regions with minimal user intervention. The exemplary system can be configured for the streamlined operation of a regulatory monitoring program, and because of these user-centric/operation-centric features, the system can be deployed by users having minimal or reduced user training as compared to current measurement systems.

In an aspect, a system (e.g., benthic lander platform) is disclosed for measuring benthic fluxes of dissolved analytes, the system comprising: an isolation structure having a plurality of pre-defined benthic flux sampling regions, including a first sampling region and a second sampling region, wherein each of the plurality of pre-defined benthic flux sampling regions is defined by a set of isolation walls; a sampling chamber (e.g., benthic flux chamber) movably coupled to the isolation structure to move among the plurality of pre-defined benthic flux sampling regions, including the first sampling region and the second sampling region, wherein the sampling chamber and a benthic flux sampling region defines a sampling volume (generally constant with natural variations due to benthic surface topographical variability for a seafloor) for a benthic flux measurement; an actuator coupled to the isolation structure to move the sampling chamber among the plurality of pre-defined benthic flux sampling regions; and a sample collection mechanism or a set of one or more sensors for collecting or measuring the benthic flux, wherein the set of one or more sensors includes a first sensor and is operatively coupled to the sampling chamber.

The term "benthic fluxes" generally refers to the exchanges of dissolved geochemical analytes between sediments and the overlying water column. Benthic incubation refers to a time period in which a benthic region (i.e., a water column parcel) is maintained in isolation on contact with sediments for the purpose of monitoring changes in chemical concentrations in this isolated water column parcel over time of some analyte of interest (e.g., nutrients, carbon, dissolved oxygen, contaminants or numerous other biogeochemical analytes of interest). "Benthic flux incubation" measurements obtained via benthic incubations may be based on monitoring, via time-series measurements, the rates of material concentration change within the chamber over time. Encapsulated chamber water concentrations will typically increase for those analytes displaying a greater concentration in sediments than in the overlying water column, e.g., ammonium or phosphate, or will decrease if sediment concentrations are less than in the water column, e.g., dissolved oxygen. These rates may be obtained via fitting (e.g., linear or otherwise fitting) from a plot of the measured concentration as a function of time after the incubation start. This "rate" of accumulation may be normalized or formatted into units of moles (accumulating) per liter per hour (moles/L·hr). The rate may be multiplied by the volume of the enclosed parcel of water within a sampling chamber to provide a measured unit of total moles (accumulating) per hour (moles/hr). The measured unit of total moles per hour may be divided by the sediment/benthic surface area to finally provide a "benthic flux," e.g., in a commonly accepted measured unit of moles per square meter per hour (moles/m² hr). Other units may be employed.

"Ambient water concentration measurements" refers to the direct measurement of an analyte of interest in the water ideally obtained without the influence of any incubation system. The "ambient water concentration measurements" combined with "benthic fluxes" can yield information such as the turnover times of water column analyte inventories with respect to benthic fluxes, i.e., constraining the relative importance of "benthic fluxes" and thus sediment influence on the water column.

"Ambient water incubations" refers to the incubation of a parcel of water in an enclosed chamber but isolated from any sediment influence, and time-series monitoring of the rate of change of some analyte's concentration, and finally fitting, to ultimately generate units of moles/L·hr. By combining rates derived from "ambient water incubations" with those obtained from "benthic flux incubations," the user is able to ultimately correct for processes localized specifically to the isolated water parcel during "benthic flux incubations" that would otherwise be inferred as contributing to "benthic fluxes."

An actuator may be motorized (employing electrical energy to actuate) or non-motorized (e.g., employing stored mechanical energy in springs or external mechanical energy, e.g., via a lead screw to actuate).

In some embodiments, the first sensor is fixably mounted to the system, wherein the sampling chamber includes a sampling port that is routed, via one or more tubes or channels, to the first sensor or the sample collection mechanism.

In some embodiments, the first sensor is fixably mounted to the sampling chamber, including a first sensor, and wherein a sensor head of the first sensor or an intake port is in direct contact with the contents of the sampling chamber. In some embodiments, the first sensors (e.g., electrochemical sensors or optical sensors) can be measured by being in contact with the contents of the sampling chamber.

In some embodiments, the sampling chamber comprises a chamber body and a chamber lid configured, via an actuator (motorized or mechanized), to move between an open configuration and a closed configuration.

In some embodiments, the sampling chamber is operatively coupled to a pump to circulate fluid in the sampling chamber (e.g., to mix the contents of the chamber for equalized or homogeneous measurement). The same pump may be used to circulate the fluid through a flow cell to provide an access point for one or more sensors to measure the fluid. In other embodiments, a separate pump or propeller mixing system is employed.

In some embodiments, the first sampling region has a perimeter defined by a sampling hole (e.g., porthole) in the isolation structure.

In some embodiments, each benthic flux sampling region of the isolation structure includes a downward-facing rim along its perimeter (e.g., to penetrate the sediment to ensure the isolation of the sediment sampling region to be incubated).

In some embodiments, the first sensor includes an electrochemical, optical, or fluidic sensor (e.g., dissolved oxygen, carbon dioxide or dissolved inorganic carbon, dissolved organic matter or colored dissolved organic matter, pH, phosphate, nitrate, ammonium, methane, turbidity, or any described herein), or a combination thereof.

In some embodiments, the set of one or more sensors further includes a second sensor comprising at least one of an optical sensor, a temperature sensor, an acoustic sensor, a light sensor, a pressure sensor, a pH sensor, an optode sensor, a combination thereof, or any described herein.

In some embodiments, the isolation structure forms a circular array of the benthic flux sampling regions.

In some embodiments, the isolation structure forms a non-circular array (e.g., rectangular array, linear array, etc.) of the benthic flux sampling regions.

In another aspect, a method is disclosed for measuring seafloor benthic flux, the method comprising: placing a benthic flux sampling system at a seafloor, the benthic flux sampling system comprising: an isolation structure having a plurality of pre-defined benthic flux sampling regions, including a first sampling region and a second sampling region, wherein each of the plurality of pre-defined benthic flux sampling regions is defined by a set of isolation walls; a sampling chamber (e.g., benthic flux chamber) movably coupled to the isolation structure to relocate among the plurality of pre-defined benthic flux sampling regions, including the first sampling region and the second sampling region, wherein the sampling chamber and a benthic flux sampling region defines a constant volume for a seafloor benthic flux measurement; an actuator coupled to the isolation structure to move the sampling chamber among the plurality of pre-defined benthic flux sampling regions; and a set of one or more sensors for measuring the seafloor benthic flux, wherein the set of one or more sensors is operatively coupled to the sampling chamber.

The method further includes positioning the sampling chamber at the first sampling region; measuring the benthic flux according to a first pre-defined measurement protocol at the first sampling region during a pre-defined period; positioning the sampling chamber at the second sampling region; measuring the benthic flux according to a second pre-defined measurement protocol at the second sampling region after the pre-defined period; and storing the measured benthic flux time-series concentration, or a parameter derived thereof, the first sampling region and the second sampling region for analysis. In some embodiments, the method to measure the benthic flux includes actuating the sampling chamber into a sealed configuration but isolated from sediments (i.e., containing only ambient water, collecting measurements (e.g., sub-hourly) while the sampling chamber is in the sealed configuration that can be later plotted or used to determine a rate of accumulation (e.g., for nutrients) or decrease (e.g., for dissolved oxygen) that may be fitted (e.g., linear or otherwise fitting) in a plot of the concentration of a measure and as a function of time after the incubation start.

In some embodiments, the steps of positioning the sampling chamber at the first sampling region and measuring the initial benthic flux employ a motorized actuation (or rotation) that is guided by a controller.

In some embodiments, the step of measuring the benthic flux at the first sampling region is guided by the controller (e.g., via computer readable instructions, e.g., based on user-defined setting).

In some embodiments, the step of measuring the benthic flux occurs when the sampling chamber is in an open structure configuration and when the sampling chamber is later in a closed structure configuration.

In some embodiments, the method further includes conducting ambient water incubations contemporaneously (before, during, or after, but at about the same time) with the measuring of the benthic flux, wherein the measured ambient water incubation is employed to adjust the measured benthic flux to a true sediment-only benthic flux measurement (e.g., via a subtraction operation of the ambient water incubations from the measured benthic flux).

In some embodiments, the ambient water incubations are measured in the sampling chamber prior to or after the benthic flux measurement.

In some embodiments, the ambient water incubations are measured in a second sampling chamber prior to, concurrent with, or after the benthic flux measurement.

In some embodiments, the sampling chamber is perturbed (e.g., contents mixed, e.g., via a pump actuation) immediately prior to and/or during the step of measuring the benthic flux.

In another aspect, a system (e.g., re-configurable benthic lander platform) is disclosed for measuring seafloor sediment flux, the system comprising an isolation structure having a plurality of pre-defined sediment flux sampling regions, including a first sampling region and a second sampling region, wherein each of the plurality of pre-defined sediment flux sampling regions is defined by a set of isolation walls; a sampling chamber (e.g., benthic flux chamber) movably coupled to the isolation structure to move among the plurality of pre-defined sediment flux sampling regions, including the first sampling region and the second sampling region, wherein the sampling chamber and a sediment flux sampling region defines a constant volume for a seafloor sediment flux measurement; and an actuator coupled to the isolation structure to move the sampling chamber among the plurality of pre-defined sediment flux sampling regions; wherein the system can be equipped with a sample collection mechanism or a set of one or more sensors for collecting or measuring the benthic flux, wherein the set of one or more sensors or the sample collection mechanism is operatively coupled to the sampling chamber.

In some embodiments, the set of one or more sensors is fixably mounted to the system, wherein the sampling chamber includes a sampling port that is routed, via a fluidic tube, to the set of one or more sensors.

In some embodiments, the set of one or more sensors is fixably mounted to the sampling chamber, wherein the sampling chamber includes a sampling port that is routed, via a fluidic cable, to the set of one or more sensors.

In some embodiments, the system further includes a controller, the controller having computer-readable instruction stored thereon, wherein execution of the instruction by a processor causes the processor to perform the positioning, measuring, and storing operation of the above-discussed claims.

In another aspect, a method is disclosed, comprising: receiving, by a processor, data values of measurements acquired from sensors of benthic flux for a body of water, including a first measurement associated with benthic flux incubation and a second measurement associated with ambient water incubation; determining, by the processor, a value for true sediment flux via a computing operation (e.g., subtraction operation, correction operation, normalizing operation, e.g., division, an inference operation, or their equivalents) that combines the data values of the first measurement associated with benthic flux incubation with data values of the second measurement associated with ambient water incubation, wherein the value for true sediment flux is made accessible for presentation (in a graphical user interface or report) in monitoring, assessment, or treatment of the body of water. In some embodiments, the true sediment flux may be determined by a transfer function/equation that employs the data values of the first measurement set associated with benthic flux incubation and the data values of the second measurement set associated with ambient water incubation. In some embodiments, the true sediment flux can be determined by a machine learning classifier using the measurements as inputs. Data values may be (i) raw values acquired from each incubation acquired per hour, calculated rates (e.g., not adjusted for volume or sediment surface area), or fluxes (i.e., normalized for sediment surface area).

In some embodiments, the method further includes receiving, by the processor, data values of a third measurement set associated with open chamber water column measurements; and determining, by a processor, value, e.g., a turnover time, using the determined value for true sediment flux and the data values of the third measurements associated with open chamber water column measurements, wherein the value for turnover time is made accessible for presentation (in a graphical user interface or report) in the monitoring, assessment, or treatment of the body of water.

BRIEF DESCRIPTION OF THE DRAWINGS

The accompanying drawings, which are incorporated in and constitute a part of this specification, illustrate embodiments and, together with the description, serve to explain the principles of the methods and systems.

FIG. 4A illustrates the various deployment scenarios of the platform in accordance with an illustrative embodiment.

DETAILED DESCRIPTION

To facilitate an understanding of the principles and features of various embodiments of the present invention, they are explained hereinafter with reference to their implementation in illustrative embodiments.

Each and every feature described herein, and each and every combination of two or more of such features, is included within the scope of the present invention provided that the features included in such a combination are not mutually inconsistent.

Example Systems

Figure 1A:
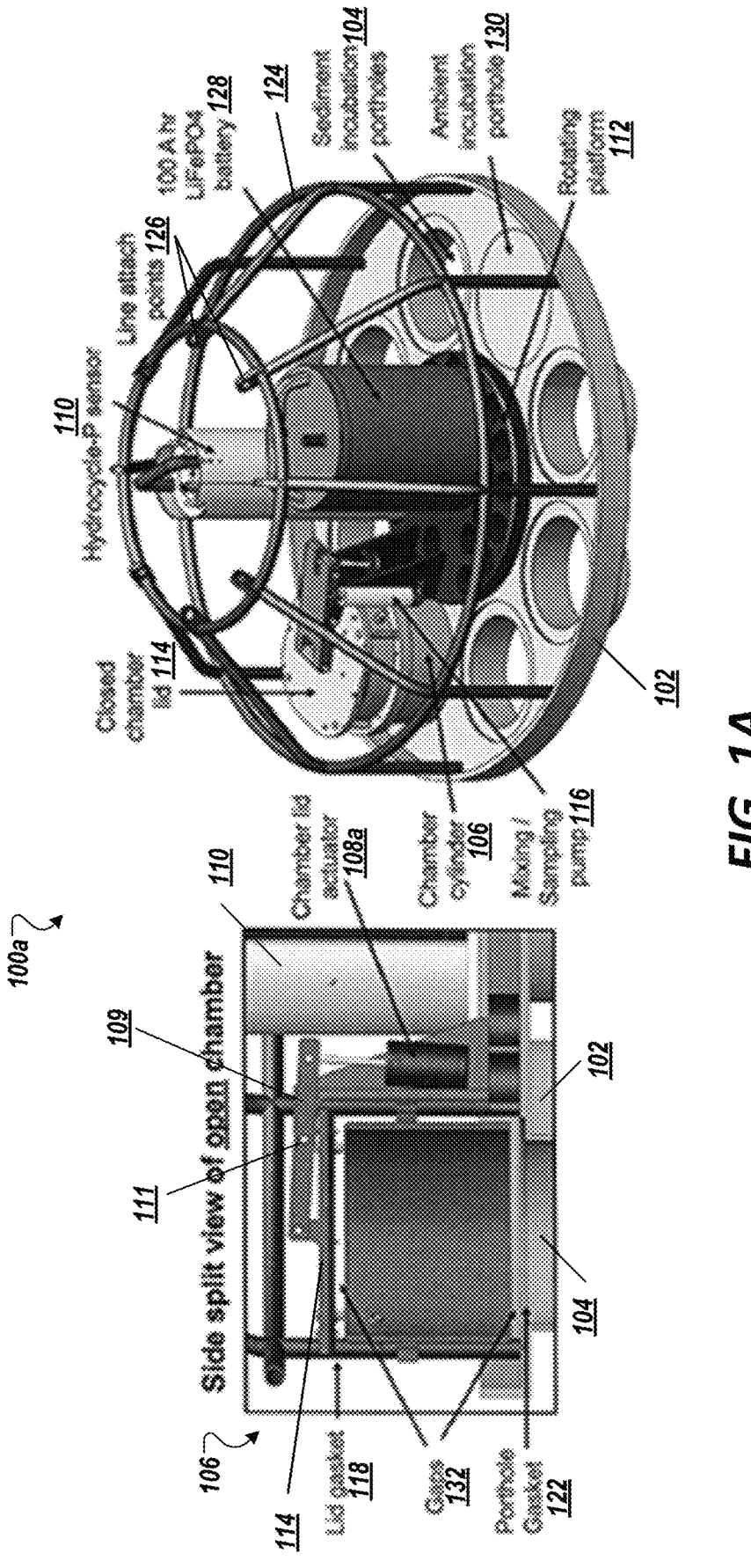
FIGS. 1A and 1B are diagrams showing examples of the benthic lander platform configured to incubate and measure benthic flux in accordance with an illustrative embodiment.
Figure 1B:
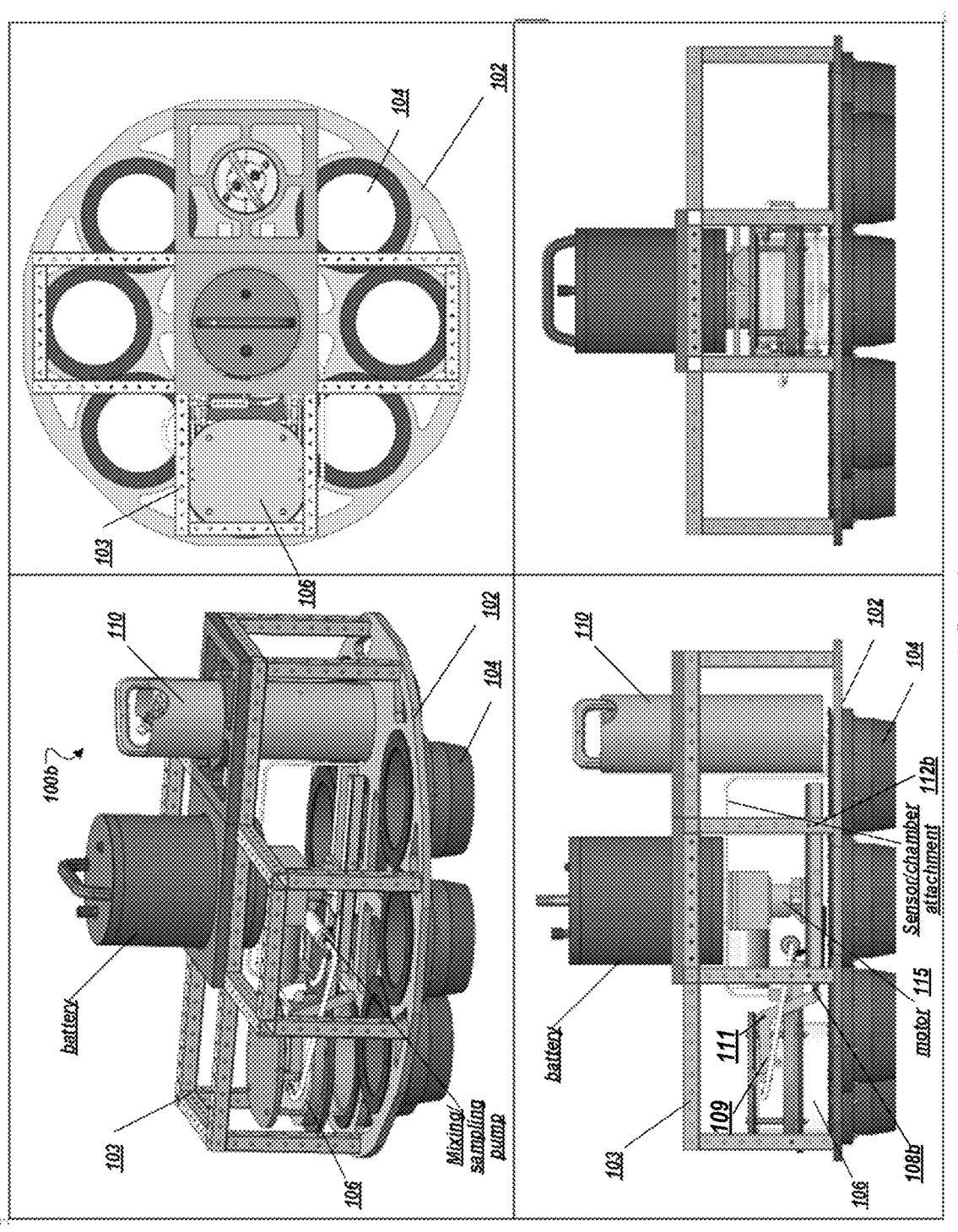
Figure 1C:
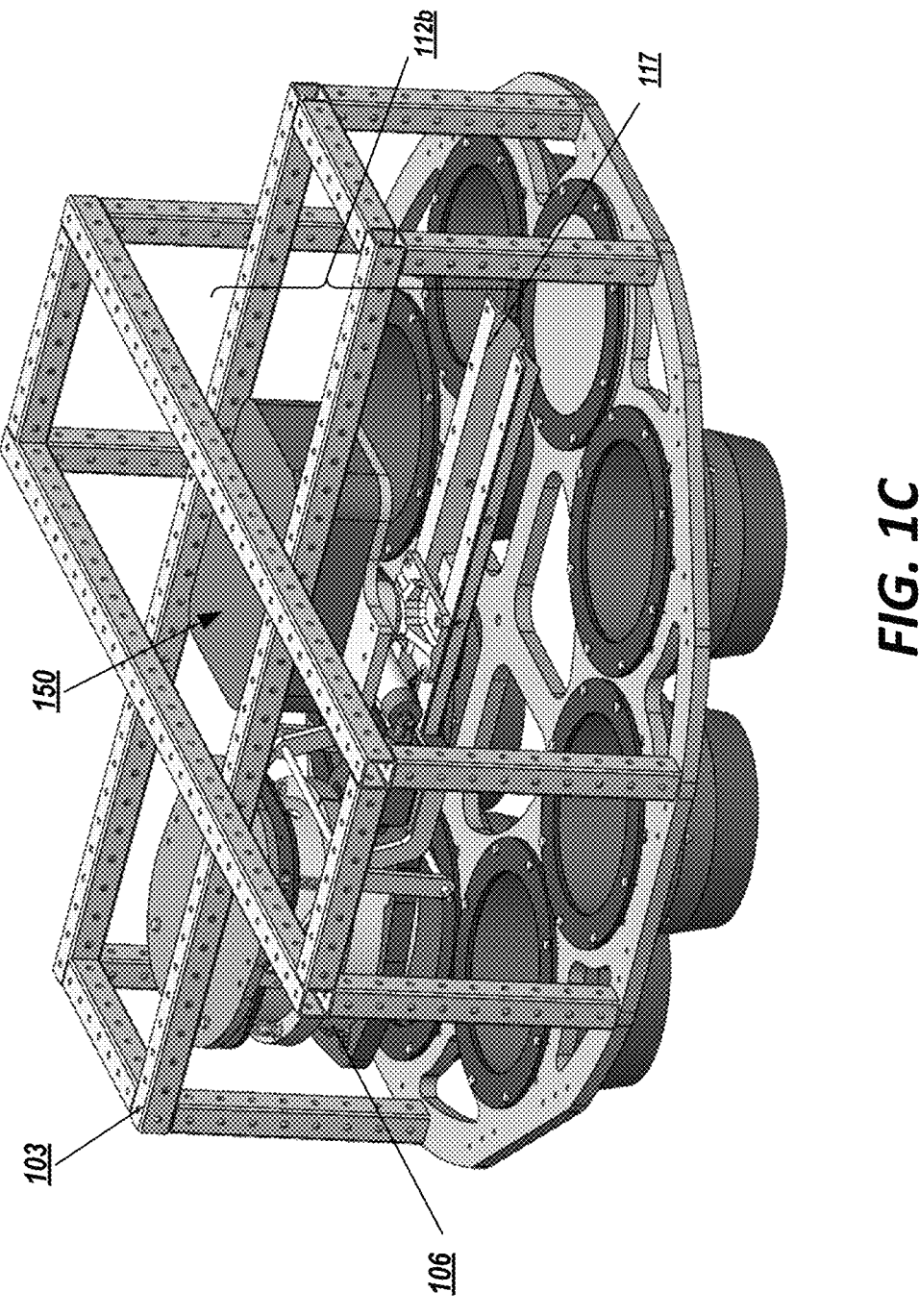
FIGS. 1C-1I also shows another example configuration of the benthic lander platform of FIG. 1B with details of the drive mechanism shown in FIGS. 1E-1I.

FIGS. 1A and 1B are diagrams showing examples of the benthic lander platform 100 (shown as 100a and 100b)

configured to incubate and measure benthic flux in accordance with an illustrative embodiment. FIG. 1C shows another configuration of the system of FIG. 1B. The platform 100 can be configured as a chamber array for long-term observation of sediment exchange. For readability, the various piping, valves, sensors, and fluidic components are not shown (see FIG. 3).

Figure 1D:
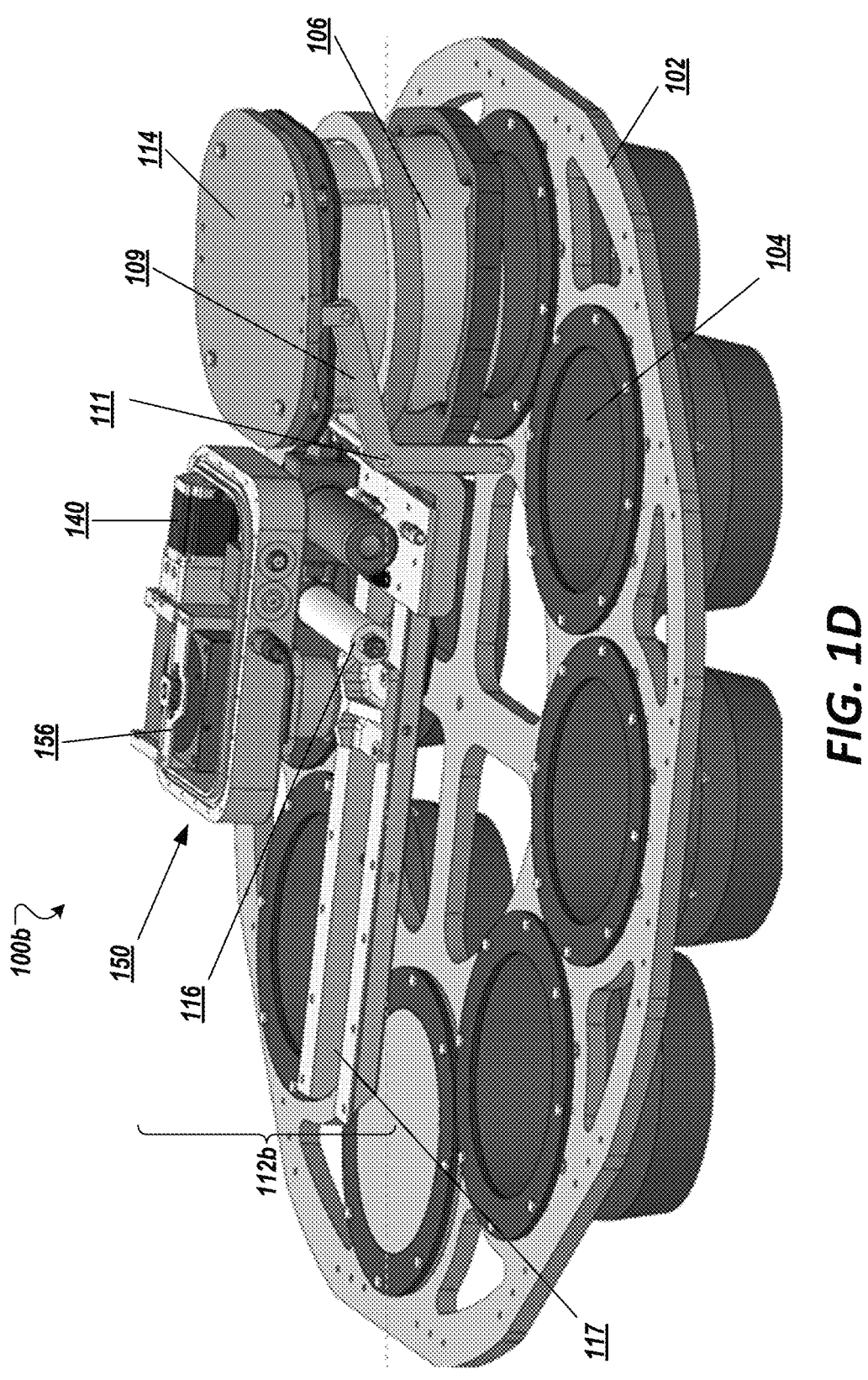

Rotating Sampling Structure. In the example shown in FIGS. 1A and 1B, the benthic lander platform 100 includes a base structure 102 that also serves as an isolation structure for a plurality of pre-defined sediment flux sampling regions 104 (shown as "Sediment incubation portholes" 104), e.g., for sampling benthic flux, via a sampling chamber 106 (shown as "Chamber cylinder 106"). In the example of FIG. 1A, the sampling and measurement components of the platform 100a are mounted on a rotating structure 112 (shown as a rotating carousel 112a) movably attached to the base structure 102. A motor assembly 115 having a motor 140 (see FIG. 1D) mounted in a rotation assembly 150 on the rotating structure 112 or the base structure 102 is configured to move the rotating structure 112 relative to the base structure 102. In some embodiments, the rotating structure is geared coupled to an external mechanically driven lead screw, e.g., actuated by a vessel, that provides movement of the rotating structure 112 and sampling chamber 106. In FIG. 1B, the components of the platform 100b are mounted to the rotating structure 112 (shown as a rotating arm or rotating platform 112b) having a rotating arm 117 that is coupled to a motor assembly 115 (shown as "motor" 115) fixably attached to a superstructure 103 that is fixably attached or extended from the base structure 102.

In the example, a lid gasket 118 and a porthole gasket 122 is included on either side of the sampling chamber 106 to form a seal between the benthic flux sampling regions 104 defined by the base structure 102 and the sampling chamber 106 (e.g., the lid 114 of the sampling chamber 106). As shown in FIG. 1A, gaps 132 are formed on the top and bottom of the sampling chamber 106 to allow ambient water to enter, when desired. In some implementations, the gap is only on the top or the bottom of the sampling chamber.

Indeed, in each of FIGS. 1A and 1B, the plurality of pre-defined benthic flux sampling regions 104 are defined by the isolation structure by each of the walls of the portholes 104. The base structure 102, e.g., as an isolation structure, is coupled with a sampling chamber 106 configured to move in relation to the base structure 102 among the plurality of pre-defined benthic flux sampling regions 104. The sampling chamber 106 can move relative to the base structure 102 to cover and interact with one of the benthic flux sampling regions 104 before controllably and selectively moving to another adjacent benthic flux sampling region 104. The sampling chamber 106 and a benthic flux sampling region 104 define a measurement volume for a benthic flux measurement.

Sampling Chamber Assembly. The sampling chamber 106 is coupled to a motorized actuator 108 (see, e.g., FIG. 1A, shown as "chamber lid actuator" 108a or FIG. 1B, shown as 108b) that is configured to move a mounting arm 109 that is hingeably connected to the sampling chamber 106 to move a lid 114 between an open position and a close position. In FIG. 1A, the motorized actuator 108a is configured to linearly move the mounting arm 109 (shown as a straight beam) around a hinge 111 to open and/or close the lid 114 movably coupled to the sampling chamber 106. In FIG. 1B, a motor 108b is coupled to the mounting arm 109 (shown as an L beam) around the hinge 111 to open and/or close the lid 114.

Figures 2A, 2B:
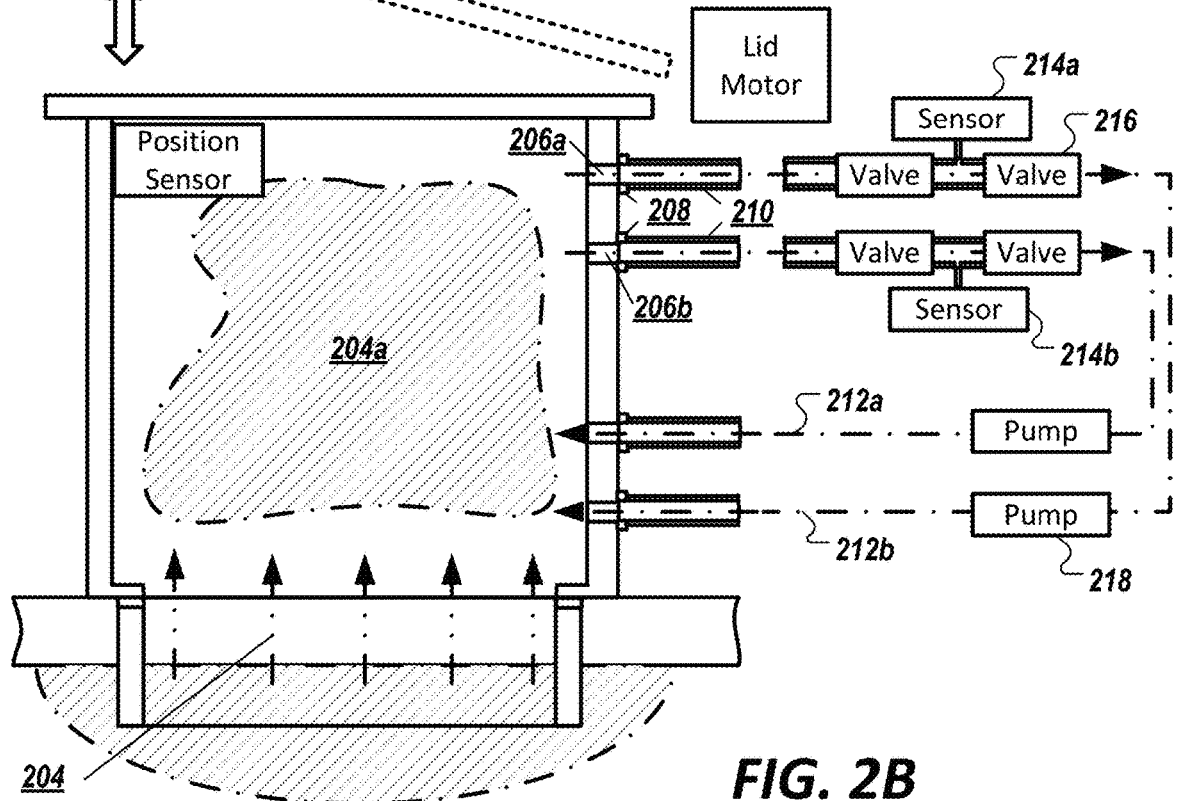
FIGS. 2A and 2B show an example operation for long-term benthic flux measurement in accordance with an illustrative embodiment.

Long-term Benthic Flux Measurement. FIGS. 2A and 2B show an example operation for long-term benthic flux measurement. In FIG. 2A, the system 100 is configured to move (202) the sampling chamber 106 between different sampling locations to minimally affect or impede the downward deposition of solid particulates and minimally reuse and perturb a single sediment location, thus allowing repeated benthic flux measurements conducted over a long period of time. The flux accumulates (shown as 204a) in the sampling chamber 106. Because benthic fluxes (shown by arrow 204) may be affected by the degradation of the downward deposition of solid particulates, the operation of the exemplary system would minimize any inhibition of this deposition relative to a single reused sediment region or re-incubated sediment region.

Any number of sampling chambers (e.g., 106) may be implemented, e.g., from 1 chamber (e.g., 106) to N number of sampling ports (e.g., 104) to N:N where there is a sampling chamber (e.g., 106) for each sampling port (e.g., 104). The number of chambers (e.g., 106) can be increased at the expense of seafloor-area-per-chamber (larger chambers essentially smooth heterogeneities). For a constant deployment length, the more chambers, the less per-chamber repeat visit frequency, and in turn, the less artifactual inhibition of natural sedimentation. It is also possible to conduct an ambient water time-series incubation (closed to the sediments) by rotating the chamber to visit the ambient incubation porthole (e.g., FIG. 1A, 130 and FIG. 1C, 106) and descending to form a seal. The configuration shown in FIGS. 1A and 1B provide for separation between the sampling regions (e.g., 104). In addition, the ambient incubation sampling may be performed between each benthic flux sampling by moving the sampling chamber to the ambient incubation position (e.g., FIG. 1A, 130 and FIG. 1C, 106), not necessarily to the nearest port among measurements at a given port.

Flux Measurement. Referring to FIG. 1A, the benthic lander platform 100 includes a sensor assembly 110 (shown as "Hydrocycle-P sensor" 110 for this example, a sensor designed by Seabird Inc. to monitor dissolved phosphate concentrations) comprising a set of one or more sensors for measuring biogeochemical concentrations to infer benthic fluxes. In the example shown in FIGS. 1A and 1B, the sensor assembly 110 is mounted to the rotating platform 104 to move concurrently with the sampling chamber 106. In other embodiments, the sensors can be mounted to the frame structure (103). For the latter case, the chamber assembly and rotating platform should rotate entirely in one direction through the series of portholes 1:N and then reverse direction from N:1 to ensure any fluidic cables remain untangled in the event of long term incubations where multiple incubations are performed at individual portholes. Examples of sensors that may be employed with the platform (e.g., 100a, 100b) are provided in Table 1 (below).

The sensor assembly 110, which may consist of multiple sensors, is connected to sampling chamber 106 via a series of tubes (or channels) and/or manifolds (e.g., flow cell manifolds). The sensor assembly 110, or sensor heads, may also be mounted to the sampling chamber 106. In some embodiments, rather than a sensor assembly or additional to, the benthic lander platform 100 includes one or more sample containers to collect and store samples from the sampling chamber to subsequently be retrieved and processed manually for later laboratory analysis.

In some embodiments, the collection operation may collect timed samples, e.g., with 50 mL syringes, for post-retrieval analysis of the lander back at the lab. This may be the only means for many applications for which in situ sensors are not practical, e.g., organic contaminants or heavy metals that require, e.g., a mass spectrometer. The collection vessels may be implemented in an array or carousel, as each benthic flux incubation requires several samples collected as a function of time, and numerous incubations are expected to be conducted during a single deployment (e.g., a 6×6 matrix syringes or other configurations).

In FIGS. 1A-C, the sampling chamber 106 is additionally coupled to a mixing/sampling pump 116 that is configured to draw contents of the sampling chamber 106 to a fluidic manifold containing sensor heads or interfaced with sensor inlet tubing of the sensor assembly 110 located in the remote location of the system. The mixing/sampling pump may be actuated in a recirculating mode to provide mixing of the contents of the sampling chamber 106 prior to the contents being sampled and measured by the sensor. The single mixing/sampling pump 116 reduces the cost of the system and improves reliability by having fewer components. It should be appreciated that other configurations may be employed, e.g., employing separate pumps for mixing and sampling.

Figure 1F:
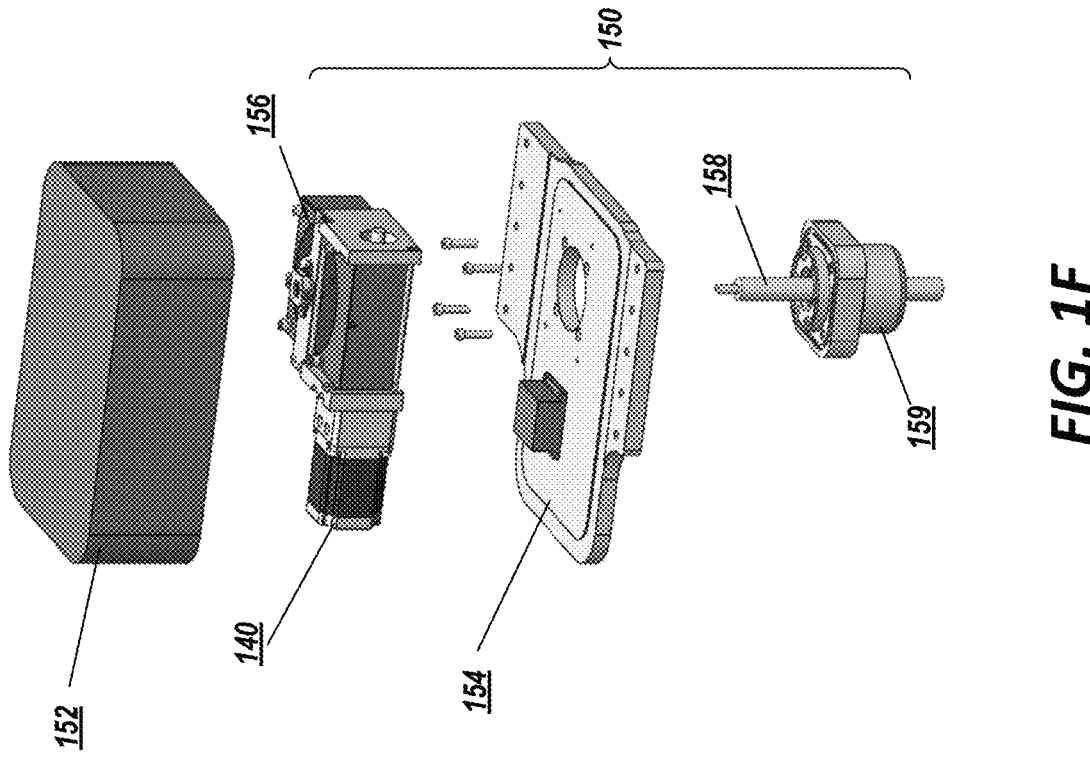
Figure 1E:
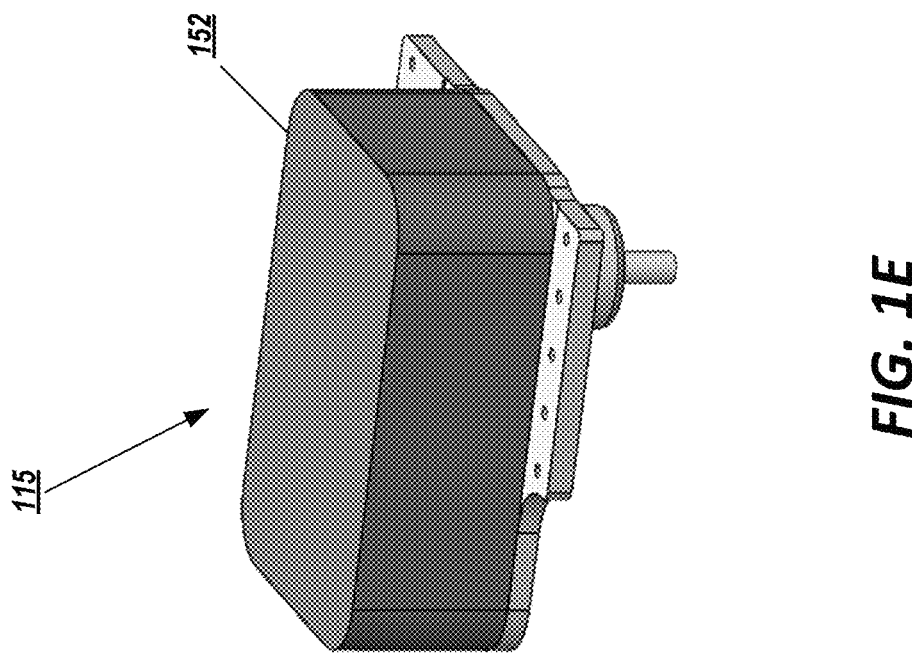

Motor assembly. FIGS. 1E-1I provide additional details on the motor assembly 115 and rotation assembly 150. In FIG. 1E, a cover 152, as an underwater pressure housing, is shown to house and seal other components from the external environment (e.g., the water). In FIG. 1F, the cover 152 is shown mounted to a base 154 with components housed therebetween.

Referring still to FIG. 1F, the motor 140 (e.g., a stepper motor) is shown positioned between the cover 152 and the base 154. The motor 140 is coupled to a gearbox or motor coupler 156. The gearbox 156 is then coupled to a shaft 158 extending beyond the base 154 to power the rotation of the rotating structure 112. The shaft 158 and the overall rotation assembly 150 is a high-torque, low velocity system configured to avoid creating a flow condition (e.g., turbulence) that would disturb the sediment.

The motor assembly 115 includes sensors to provide absolute positioning to move the sampling chamber 106 around to each sampling port 104. For example, the exact location and rotation distance of the rotating structure 112 and/or the sampling chamber 106 is measured and tracked by encoders (e.g., an encoder, resolver, or similar device in the gearbox or motor coupler 156). As a result, the drive mechanisms do not require a zeroing or reinitialization process to a home position.

Figures 1G, 1H:
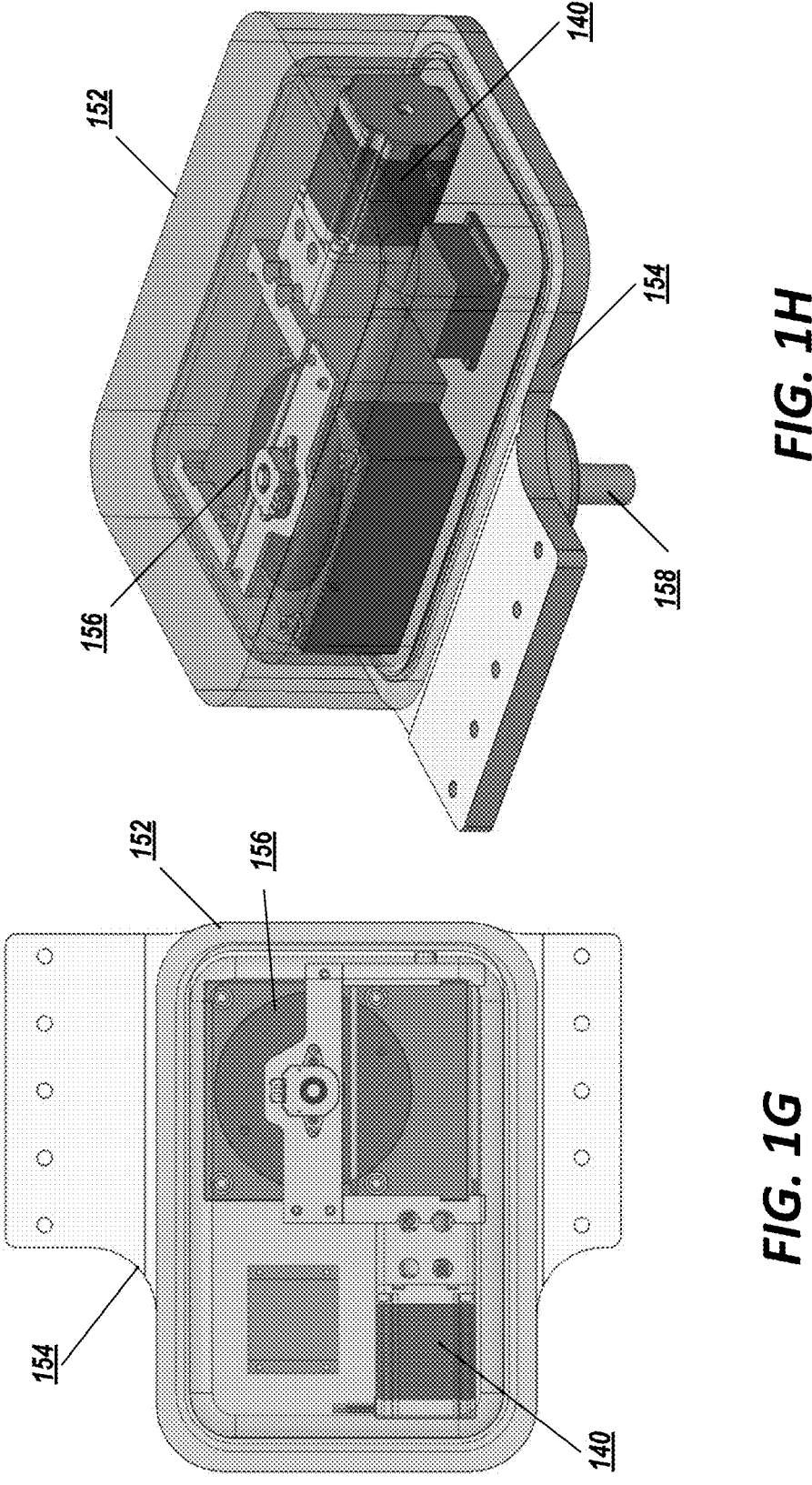
Figure 1I:
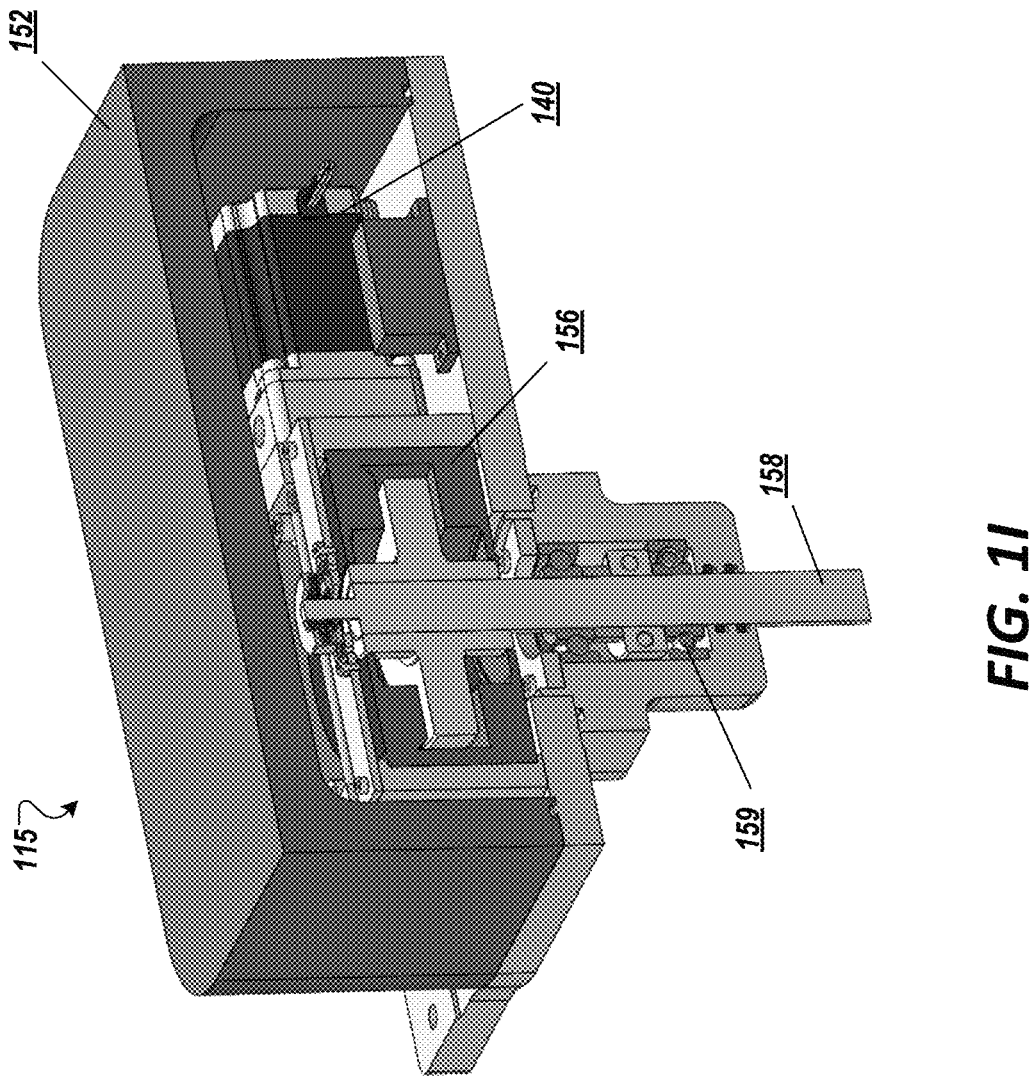

The rotation assembly 150 includes the shaft 158 that operates with bearing assembly 159 and connects to the gearbox or motor coupler 156 on one side and to the rotating arm 117. FIGS. 1G and 1H show assembled views of the motor assembly 115. FIG. 1I shows a cut-through view of the motor assembly 115.

FIG. 2B shows an example implementation of the chamber sampling sub-system. In FIG. 2B, the sampling chamber 106 includes ports 206 (shown as 206a, 206b) having connectors 208 that couple to pipe 210. Multiple parallel lines 212 may be implemented in which each line has one or more sensors 214, or a single line 212 can be implemented having multiple sensors 214. In FIG. 2B, the lines 212 (shown as 212a, 212b) are each coupled to a sensor 214 (shown as 214a, 214b) to which disparate flows for measurement can be controlled via actuatable valves 216. The valves 216 may be in a normally closed configuration and open for measurement when energized. Each line 212a, 212b may include a pump 218 to sample the contents of the sampling chamber 106 and, in the example shown in FIG.

2B, return the content to the chamber 106. In some configurations, e.g., when the measurement generates a waste stream, the samples are routed to the space outside the chamber 106. Other configurations of the sensor assembly may be implemented. In some embodiments, the sensor may be configured to pass-thru into the chamber (e.g., cable connection on the tail end of the sensor outside the chamber, with the sensor head penetrating internally). During measurement, the lid 114 is closed to maintain the accumulated benthic flux in the sampling chamber for a predefined period of time.

Most current benthic flux chamber incubations have been conducted for the purposes of fundamental monitoring, such as establishing carbon, dissolved oxygen, nutrient, or contaminant biogeochemical budgets. Current in situ benthic flux monitoring devices tend to be research-grade, requiring expert operators and complicated logistics, often that can be supported by a moderately-sized oceanographic research vessel. The exemplary system, via its features and designs discussed above, can substantially reduce the preparation- and labor-intensive work of multiple technicians, streamline the deployment and extraction process, improve usability, improve scalability and flexibility, and substantially reduce the cost of operation.

Referenced Measurement. In another aspect of the measurement, and as shown in FIGS. 1A and 1B, the benthic lander platform 100 is further configured by moving the sampling chamber 106 to a closed port 130 (shown as "Ambient incubation porthole 130") to incubate and measure ambient water incubations. In the open position, there is a gap 132 formed between the lid 114 of the sampling chamber 106 and the chamber sidewall, e.g., facilitated with springs attached between the chamber sidewall and chamber lid 114, that allows flushing and equilibration of chamber contents with ambient external waters. That is, the springs connected to the chamber lid 114 and the chamber cylinder 106 can actuate to ensure that the lid lifts off the cylinder when the platform is lifted from a settled position. The opened lid forms the gaps 132 in the sampling chamber 106 that allow the ambient water column to enter and equilibrate over time, and time-series measurements (not incubations) may be measured. The sensors for the measurement may be positioned in the lid 114 or accessible to the flow cell, with the recirculating pump 116 being employed to sample the ambient waters instead of incubated water parcels (so long as enough time is allowed for said equilibration). To minimize residual influence from the sediments, this ambient water sampling protocol should be performed while the chamber is positioned above the ambient incubation porthole 130 (albeit with the lid open). In this configuration, benthic flux measurements, ambient water incubations, and ambient water concentration measurements can be conducted with only a single chamber, single mixing/sampling pump, and single set of sensors, without needing additional pumps or valves to accomplish the redirection of sample streams. Of course, additional hardware, e.g., incubation chamber assemblies, pumps, and sensors, can be added for redundancy or parallel operations when desired.

Figures 2C, 2D, 2E, 2F:
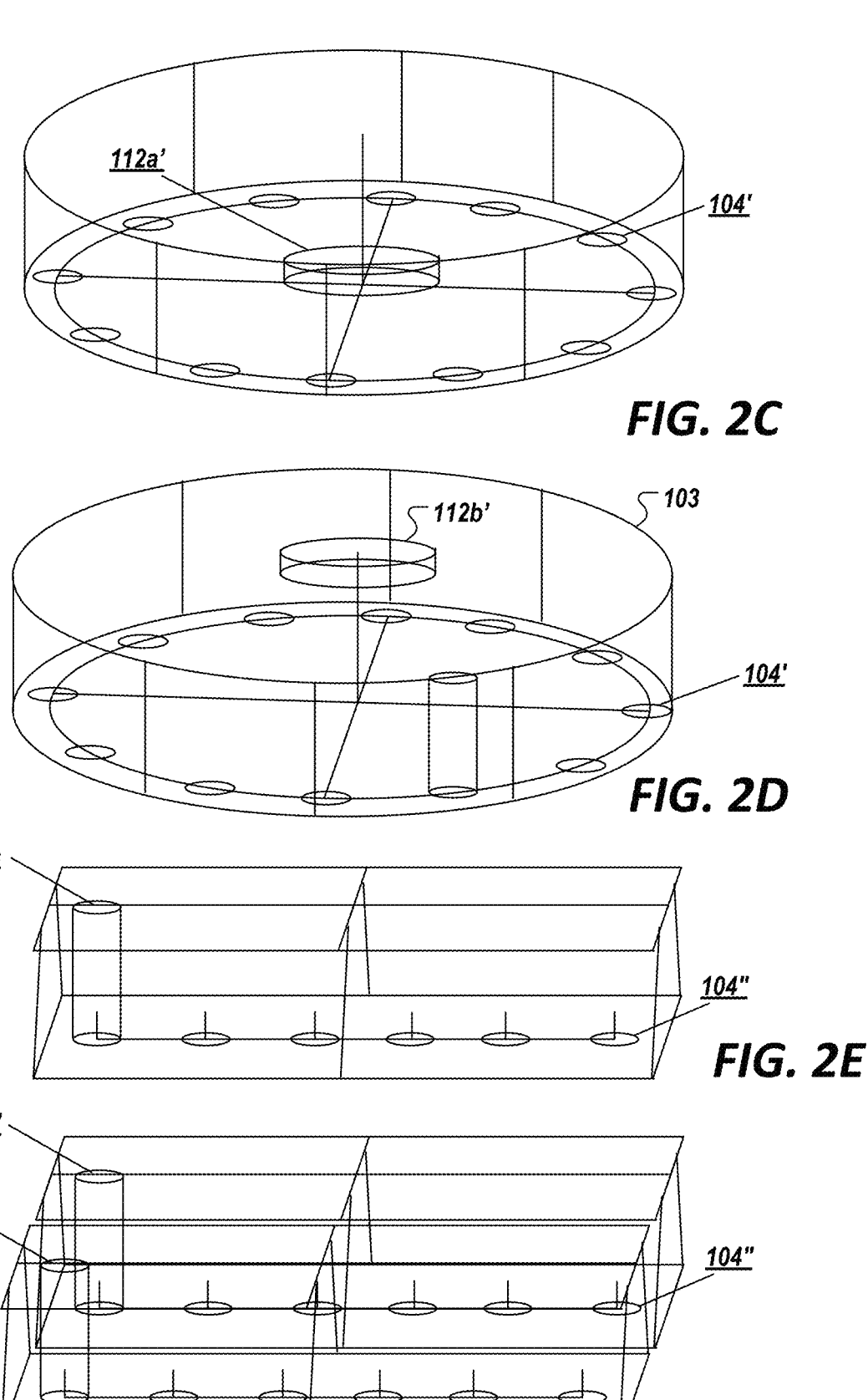
FIGS. 2C-2F show example configurations of the base structure and movable structures in accordance with an illustrative embodiment.

System Topology. Although shown as a circular window, other shapes (e.g., oval, squares, rectangle, etc.) may be employed for the benthic flux sampling regions 104. In some embodiments, the base structure 102 may be configured as a grid or linear array that allows the sampling chamber to be moved in a linear manner or in an x-y grid direction. FIGS. 2C-2F show example configurations of the base structure 102 and movable structures. In FIG. 2C, the base structure 102, having circularly arranged sampling ports 104 (shown as 104') is movably coupled to a base rotating platform 112 (shown as 112a'). In FIG. 2D, the base structure 102 having circularly-arranged sampling ports 104' has a superstructure 103 having a hanging rotating platform (shown as 112b'). In FIG. 2E, the base structure 102 having linearly-arranged sampling ports 104 (shown as 104") is movably coupled to a linear moving sampling platform 112 (shown as 112c). In FIG. 2F, the base structure 102, having two linearly-arranged sampling ports 104 is movably coupled to two linear moving sampling platforms (shown as 112c' and 112c") to form a 2×N array. The multiple ports and fewer sampling chambers 106 allow fewer components (e.g., sensors, sensor connections, and hardware actuation) to be implemented. In a fixed sampling chamber topology (not shown), the sampling chamber (e.g., 106) can be fixably attached to the base structure, and the lid assembly is allowed to move.

Deployment Structure. In FIG. 1A, the base structure 102 is attached to a cage structure 124 having line attachment points 126 on the top side of the platform 100a. The line attachment points 126 are configured to couple to deployment and mooring/buoy lines (e.g., to a boat on the surface). A centrally located battery 128 (shown as "100 A hr LiFePO4 battery 128) is coupled to the rotating platform 112 and configured to provide power for components of the platform 100a. Similar attachment structures can be implemented on the superstructure 103 of platform 100b.

Example Measurement Circuit

Figure 3:
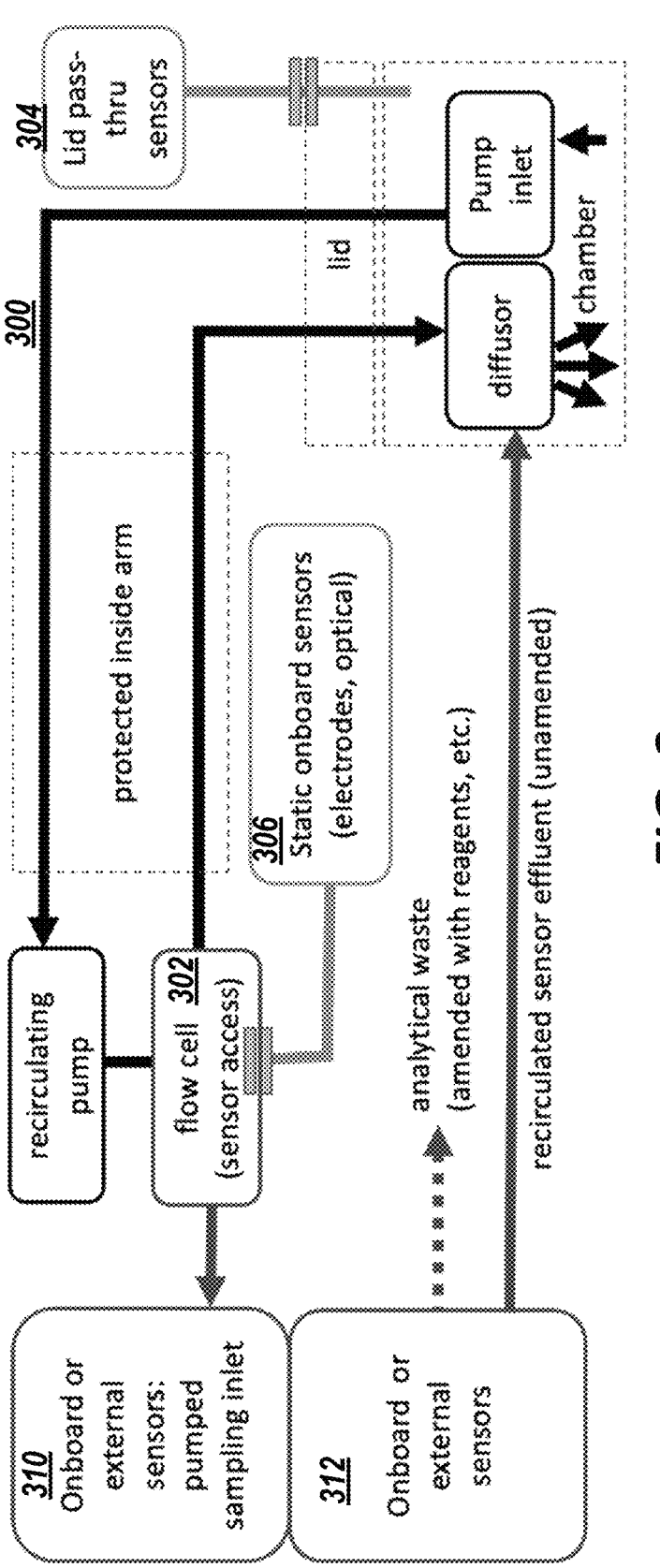
FIG. 3 is an example flow path of a recirculating path that provides chamber mixing and accessibility for ancillary sensors in accordance with an illustrative embodiment.

FIG. 3 is an example measurement flow path 300 that recirculates samples acquired from the sampling chamber 106. The recirculating path provides chamber mixing and accessibility for ancillary sensors.

When access to this recirculating flow path 300 is desired for sensors, an optional flow cell 302 (in purple) may be positioned in line with the recirculating fluidic path. Simple static sensors that are capable of just being exposed to the recirculating water/chamber contents can be positioned with the sensor heads either directly in the chamber lid or in this flow cell (green sensor blocks, labeled 304 and 306). Lastly, sensors external to the platform 100 or those onboard the platform 100 that intake fluidic samples (in red, labeled 310, 312) can also access the recirculating fluidic path via the flow cell. These sensors can either return the samples to the chamber or, if samples were modified with reagents (e.g., for colorimetric analyses), discard the waste to a separate waste container (e.g., an IV bag) or the environment (depending on the nature of the waste). In some embodiments, fluidic sensors consuming samples may be selected based on small volume consumption so as to minimally perturb incubated sample volumes.

Table 1 shows examples of sensors that may be employed with the platform (e.g., 100a, 100b) and this list is not exhaustive.

TABLE 1

| Example Sensors | | |
| --- | --- | --- |
| Analyte | Example sensor(s) | Frequency/Duration |
| salinity/conductivity & temperature | Onset HOBO or Solinst Levellogger (in the lid), Seabird HydroCAT | <1 s |
| Dissolved oxygen, hydrogen sulfide, and sediment respiration indicators dissolved iron(II) & manganese(II) (if desired) | Hg/Au voltammetry (in the lid); Analytical Instrument Systems ISEA-X | 4 electrodes (i.e., all listed analytes at 4 locations) every 10 min |
| Dissolved oxygen | Clark electrode (in chamber lid) | <1 s |
| Dissolved oxygen | optode (in the lid); Aanderaa or Pyroscience | <1 s |
| Hydrogen sulfide, dissolved oxygen, pH, redox potential, hydrogen gas, nitric oxide or nitrous oxide | Electrochemical (in chamber lid); Unisense | 1 s |
| Nutrients (phosphate) | Colorimetric: Seabird Hydrocycle-P (w/flow cell); Clearwater sensors Phosphate | <30 min |
| Nutrients (nitrate) | Optical: (Seabird SUNA w/ flow cell or YSI EXO2 in the lid) | <1 min |
| Nutrients (nitrate) | Colorimetric: Clearwater sensors Nitrate + Nitrite | <30 min |
| Nutrients (nitrate, nitrite, phosphate, ammonia, urea) | Colorimetric: Systea WIZ | <30 min |
| pH | ISFET/solid state: Seabird SeaPHOx or SeaFET; ANB Sensors OC300) | <1 s |
| pH | Colorimetric: Sunbirst SAMI-pH | <30 min |
| pH & ORP | Electrochemical (for freshwater): Seabird 27 | <1 s |
| Dissolved organic carbon (DOC) | Fluorometric (CDOM fluorometer): Turner C3, Seabird HydroCAT-EP | <1 s |
| Dissolved organic carbon (DOC) | Absorption: Wetlabs ac-s | <1 s |
| Particulates | Backscatter sensor: Seabird BB3; or Sequoia Scientific LISST sensor series | <1 s |
| pCO2 | Colorimetric: Sunburst SAMI-CO2; infrared: Pro-Oceanus CO-2 Pro | <30 min |

TABLE 1-continued

Example Sensors

| Analyte | Example sensor(s) | Frequency/Duration |
|---|---|---|
| Contaminants: Heavy Metals | Electrochemical (various) | <30 min |
| Contaminants: Organics | Electrochemical (various) | <30 min |
| Contaminants: Organics | Automated Passive diffusive sampling device for later lab analyses (e.g., Technicap THOE) - requires substantial additional integration | <1 day |
| Contaminants: Multiple | Automated water sampling device for later lab analyses: McLane Remote Access Sampler; Analytical Instrument Systems Syringe-1 | <30 min |

Sampling Chamber Mixing/Sampling Operation

Referring to FIGS. 1A and 1B, the single chamber assembly comprises a chamber lid, chamber lid actuator, chamber cylinder, lid gasket, and a mixing/sampling pump.

In the example shown in the figures, the chamber lid is removably attached to the chamber cylinder with a spring mechanism. When the chamber lid actuator is retracted, the single chamber assembly is configured to relax to an open position to create a gap between the chamber lid actuator and the chamber assembly. This action deliberately allows for leakage (i.e., to reset and thus allow a new incubation to proceed or for sampling the ambient waters). When the chamber is positioned over a porthole and the actuator is extended, the chamber lid and the chamber cylinder form a seal with the porthole. The assembly is considered to be in the closed position when this occurs. In the open position, the assembly prevents air bubble capture and sediment pressurization effects during position transitions and allows sampling of ambient bottom water as well.

In the example shown in the figures, the platform 100 includes a lander base structure 102, which is set on the seafloor at the time of deployment to create a physical interface between the sediment and the chamber. The planar shape of the base structure limits penetration of the overall platform 100 into the sediments and provides a static foundation for operations. The base structure 102 includes individual sediment portholes 104 (preferably between 4 and 10, depending on the desired size), each porthole 104 capable of accepting and forming a gasket seal with the single chamber assembly in order to start each incubation while also minimally perturbing natural sedimentation and horizontal advective flow (water currents) when not in use.

Each porthole 104 on the base structure 102 is open to the sediment in its default setting, but a user may seal one or more of the portholes by covering the porthole with a disc, allowing control/reference ambient water incubations of the benthic boundary layer waters isolated from sediments by closing the chamber on this sealed porthole. This sealing allows the quantification of non-sediment-driven background processes such as nutrient assimilation, respiration and nutrient release, or photosynthetic dissolved oxygen production. With the shown configuration of the chamber assembly and pumping/mixing system, it is also possible to sample while in the relaxed or open position. This allows time series sampling of ambient waters, which means the samples will not be incubated over time. In an alternative embodiment, the chamber assembly can be positioned over any solid plane to allow the chamber assembly to be sealed and conduct ambient incubations.

Each porthole 104 of the base structure 102 also includes a downward-facing rim along its perimeter, which beneficially ensures that each porthole forms a seal with the sediment in contrast to a more conventional benthic incubation chamber, which would directly penetrate the sediment itself, thus limiting carryover of sediment during repeat incubations. The base of the platform controls the rim's penetration depth. The base of the platform includes a short upward-facing vertical flange around the entire perimeter that forms a barrier against the ingress of adjacent sediments resuspended during deployment.

In certain embodiments, the system 100 may allow adjustment for benthic topography. Upon deployment, if encountering local topographic highs, each porthole flange can slide upward, unobstructed, to ensure the platform is positioned horizontally on the seafloor and the remaining portholes do not penetrate too far into the seafloor. For each porthole 104, the flange adjustment would not interfere with the chamber depression mechanism, but it does alter the chamber volume. The chamber volume may be measured via massbalance techniques using an injected tracer (e.g., chloride, bromide, or iodide) and the inclusion of an appropriate sensor or sampling mechanism to allow measurement of the resulting tracer concentration in the chamber, a known procedure.

If a user desires to have prolonged, repeated measurements of fluxes (e.g., weeks to months), and a certain level of perturbation is acceptable, each of the sediment portholes 104 may be revisited by the chamber assembly. This avoids the frequent reuse of a single porthole and, thus, the induction of perturbations to that specific sediment area that could otherwise result in artifacts when inferring benthic fluxes. A sequence of porthole visits can be routinely implemented after a preset period of inactivity.

The opening and closing of the chamber are driven by software, so incubations may be conducted either during the day or night or both sequentially. This allows for discrimination between photosynthetic and respiration-linked processes when the chamber is constructed of optically transparent material such as polycarbonate or acrylic. A user could also achieve this by attaching two chambers, one opaque and one transparent, to the positioning mechanism.

In certain embodiments, sensors may be attached directly to the chamber lid. Non-limiting examples of such sensors include electrodes, optodes, or optics "puck" sensors. Uniquely, the use of a single-chamber design allows for the use of only a single sensor set per platform (e.g., 100) rather than having to use a separate set of sensors for each chamber, porthole, or ambient water sampling location. This also reduces the effort needed for sensor inter-calibration.

In certain embodiments, fluidic sensors may be used. The chamber or ambient water contents may be aspirated via a single sampling inlet tube affixed permanently into a port in the chamber lid, directed through the chamber lid into a centralized analytical flow stream accessible to the onboard or external sensor of choice (FIG. 1B with onboard sensor depicted), and back through the chamber lid along a return fluidic path for dispensing into the chamber (minus any small volume potentially removed by any in situ sensor(s) equipped onboard the platform 100 or external to the platform). This sampling mechanism is enabled via a standard underwater pump that also serves as the primary chamber circulation system.

In certain embodiments, the chamber lid includes a check valve to allow automatic pressure-based re-equilibration with ambient water when sample aliquot volumes are removed from the fluidic flow path via any in-line sensor, thus limiting artifactual flux enhancements due to pressure differentials. Depending on the specific sensor sample size requirements, this volume should rarely exceed 5% of the total chamber volume (e.g., 500 mL sampled from a 10 L chamber) and can be accounted for during flux calculations.

In certain embodiments, the platform controller hardware is configured, via computer instructions, to activate the mixing and sampling pump at preprogrammed intervals that will typically correspond with the benthic chamber placement and incubation start time. Pass-thru power ports and bidirectional communications/control ports may be employed to enable the platform to control ancillary sensors as well. In alternate embodiments, the platform 100 is configured with power regulators to allow it to interface with a wide range of supply voltages from external power supplies.

In alternate embodiments, the platform 100 is configured to operate adjacent to a separate, external sensor suite such that the sample inlet mechanism for these existing sensors would be interfaced with the platform 100's chamber circulation system (i.e., pump and inline sampling flow cell). This can allow the measurement of benthic fluxes while not sacrificing the original ability of the external sensor suite to still collect ambient water measurements since the platform 100 can facilitate the completion of both tasks (although ambient water measurements would be prohibited during the incubation steps). If real-time control and data transmission are desired for incorporation into existing networks, the platform 100 can include a Hardwired, RF, Cellular, or Satellite modem, or can be integrated to the external sensor suites telemetry system to share communication capabilities.

In some embodiments, the platform 100 is configured to reset or flush the contents of the sampling chamber from the act of lifting the chamber or platform. In an example, the act of lifting the chamber may automatically result in a spring-induced opening of the chamber lid, allowing the flushing of the chamber contents from both the bottom and top of the chamber while also eliminating bubbles.

The sampling chamber is always equilibrated with the ambient waters after a short period of time after it is opened and the sample pump is actuated, thus inherently "resetting" it and setting the stage for a follow-up incubation with a flushed chamber. It also allows measurement of the ambient water (without conducting an incubation).

Example Controls and Software Operation

The platform is configured to operate autonomously according to a sequence file that specifies the variables of the deployment.

Computer-executable instructions, such as program modules, being executed by a computer may be used. Generally, program modules include routines, programs, objects, components, data structures, etc., that perform particular tasks or implement particular abstract data types. In its most basic configuration, the controller includes at least one processing unit and memory. Depending on the exact configuration and type of computing device, memory may be volatile (such as random-access memory (RAM)), non-volatile (such as read-only memory (ROM), flash memory, etc.), or some combination of the two. The computing device may include additional storage (removable and/or non-removable).

The various operations described herein may be implemented in connection with hardware components or software components or, where appropriate, with a combination of both. Illustrative types of hardware components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. The methods and apparatus of the presently disclosed subject matter, or certain aspects or portions thereof, may take the form of program code (i.e., instructions) embodied in tangible media, such as flash drives, hard drives, or any other machine-readable storage medium where, when the program code is loaded into and executed by a machine, such as a computer, the machine becomes an apparatus for practicing the presently disclosed subject matter.

Although exemplary implementations may refer to utilizing aspects of the presently disclosed subject matter in the context of one or more stand-alone computer systems, the subject matter is not so limited but rather may be implemented in connection with any computing environment, such as a network or distributed computing environment. Still, further aspects of the presently disclosed subject matter may be implemented in or across a plurality of processing chips or devices, and storage may similarly be implemented across a plurality of devices. Such devices might include personal computers, network servers, handheld devices, Autonomous Underwater Vehicles (e.g., when the AUV serves as a relay for the data collection), and wearable devices (e.g., on divers), for example.

Examples of the variables include incubation details, such as chamber location and open/closed status, or sampling details, such as delay, frequency or repeat number, duration, etc. The sequence file is automatically generated by the deployment planner software. Tables. 2A-2E show example sequence files to control benthic measurement flux by the exemplary platform 100. The values are user-definable for a measurement of interest. The values presented are examples for one scenario. The values for analysis may also be user-defineable.

In FIG. 2A, the sequence file is configured to specify the deployment length and incubation times.

TABLE 2A

| Deployment Logistics | Units | Values |
|---|---|---|
| Deployment length | days | 30 |
| Daytime incubation start time | | 9:00 |
| Nighttime incubation start time | | 22:00 |

FIGS. 2B and 2C provide for the number of sediment flux incubation and ambient water incubation based on the time of day and the duration length of each incubation.

TABLE 2B

| Sediment flux incubations | Unit | Values |
|---|---|---|
| Number of Daytime sediment flux incubations | | 6 |
| Number of Nighttime sediment flux incubations | | 6 |
| Length of each Daytime sediment flux incubation | hours | 8 |
| Length of each Nighttime sediment flux incubation | hours | 8 |
| Time before sediment incubations to move to position | hours | 0.1 |

TABLE 2C

| Ambient water incubations | Unit | Values |
|---|---|---|
| Number of Daytime ambient incubations | | 6 |
| Number of Nighttime ambient incubations | | 6 |
| Length of each Daytime ambient incubation | hours | 8 |
| Length of each Nighttime ambient incubation | hours | 8 |
| Time before water incubations to move to position | hours | 0.1 |

FIGS. 2D and 2E provide for the ambient water sampling parameters and the benthic sampling parameters.

TABLE 2D

| Ambient water sampling | Unit | Values |
|---|---|---|
| Collect before and after sediment flux incubations? | | y |
| Collect before and after ambient incubations? | | y |
| Number of additional measurements on incubation days | | 4 |
| Number of measurements on non-incubation days | | 8 |
| Time before water sampling to move into position | hours | 1 |
| Time ambient water sampling to occur @ 15/20/30/60 minute intervals? | | 60 |

("−1" defaults to even distribution regardless of timing)

TABLE 2E

| Sampling & timing pump | Unit | Values |
|---|---|---|
| Return to ambient water sampling position after incubations? | | y |
| Pump always on? | | y |
| Pump on time prior to event (if above is "no") | hours | 0.5 |
| Delay after lid close to activate sample relay | minutes | 3 |
| Sensor power relay always on? | | n |
| Frequency of sensor power relay on during incubations (if above is "no") | minutes | 60 |
| Minutes per sample cycle (to leave sensor power relay activated) (if above is no") | minutes | 30 |

According to the user inputs, the deployment planner software can be used to receive parameters for a set of control operations for the benthic platform (e.g., 100). Table 3 shows a set of example control operations in the control of the pump, sensors, and acquisition hardware.

TABLE 3

| Step Number | Time (sec) | Action/Step |
|---|---|---|
| 3 | 35 | Activate pump |
| 4 | 55 | Relay: Activate P sensor (1 cycle) |
| 5 | 75 | Relay: Deactivate P sensor |
| 6 | 75 | Position: Ambient Flux (Chamber 1) |
| 7 | 100 | Relay: Activate P sensor (19 cycles) |
| 8 | 500 | Relay: Deactivate P sensor |
| 9 | 500 | Position: Sediment Flux (Chamber 2) |
| 10 | 525 | Relay: Activate P sensor (19 cycles) |
| 11 | 925 | Relay: Deactivate P sensor |
| 12 | 925 | Position: Ambient |

TABLE 3-continued

| Step Number | Time (sec) | Action/Step |
|---|---|---|
| 13 | 945 | Relay: Activate P sensor (1 cycle) |
| 14 | 965 | Relay: Deactivate P sensor |
| 15 | 965 | Deactivate pump |
| 16 | 965 | Pause 120 minutes |
| 17 | 1085 | Activate pump |
| 18 | 1105 | Relay: Activate P sensor (1 cycle) |
| 19 | 1125 | Relay: Deactivate P sensor |
| 20 | 1125 | Deactivate pump |
| 21 | 1125 | Repeat steps 16 through 20 through 3600 minutes (day 2) |
| | 3600 | Begin sequence. Revisit the Ambient Flux position (Chamber 1), but then for sediment flux move to unused Chamber 3 |

Planner Software. The deployment planner software is configured to be user-friendly, with the inherent level of complexity of sequence planning automatically handled by the software. By default, the sensor will evenly spread the desired number of incubations of a single type (e.g., sediment/dark) over the duration of the deployment. The benthic flux incubations and ambient incubations will also, by default, best align so that they are conducted as close in time to one another to ensure comparability and mathematical extraction of information that requires data from both types of incubations. Ambient samples can be conducted immediately before and after the incubations, allowing, e.g., the calculation of the turnover time of the water column inventory with respect to the benthic fluxes. Ambient samples can then be collected on a separate timeline throughout the duration of the deployment at a set frequency when incubations are not active. The sampling/mixing pump is automatically turned on and off at ideal periods during the deployment to minimize carryover but also conserve power. The anticipated power requirements are provided via the user interface pre-deployment to ensure the total power consumption is within the available capacity.

In certain embodiments, the system's onboard computer automatically generates a time-series log, e.g., ASCII-formatted, containing the data outputs of any sensor interfaced with the platform's controller. The log file can be downloaded and easily imported into any plotting software by the operator at the end of the deployment. With generic in situ sensors (see Table 2) that directly output time-series concentration data, the software package is capable of automatically matching up the data with relevant logistical events. For example, each sediment or ambient water incubation can be represented as a subset time series adjusted to have the zero time points correspond to that incubation's start time (i.e., lid closing). Alternatively, an ambient water concentration time series plot is automatically generated to provide an environmental context for any incubation results.

Flux Rate Calculation. Flux rates can be automatically calculated via the onboard controller based on the rate of accumulation in the chamber normalized to the sediment surface area. The system may apply corrections for the chamber-isolated volume if an inert tracer was injected or for each time step to account for the removal of water samples from the chamber. For example, if the chamber is allowed to constantly re-equilibrate with respect to pressure changes via the equilibration tube described in [11], then the system may account for the dilution of the chamber-measured analytes with this external water (which can be assumed to have a chemical composition of the chamber incubation at time zero or the ambient water concentration measurements conducted immediately before or after the incubation). Water column biogeochemical process rates from any ambient water column incubations (i.e., incubations conducted isolated from sediments) may be used to account for water column localized processes, e.g., nutrients accumulating in the chamber due to respiration. Quality control checks for both rates may consider the congruity of sensor data derived from the incubation chambers in the context of the ambient water column measurements. The quality control checks may include: 1) determining whether the ambient samples collected immediately before deployment are consistent with those of the first timepoint of an incubation; 2) determining whether the time series rate of change of the concentration is linear and whether there are multiple rates of accumulation or a sudden shift (suggesting a change in biogeochemical processes or leak); and 3) determining whether the tracer fluid behaves as expected. These types of checks can reduce the potential for user bias and ensure a greater level of data cross-comparability, especially between operators.

Sample Collection. Water samples may also be collected, filtered, and preserved in situ as a function of time with the installation of an optional sampling device that aspirates from the sampling flow cell and collects samples. Samples using individual 60 mL syringes, for example, can be collected, allowing later analyses of those analytes not measurable in situ. The syringes can be prefilled with a preservative, such as acid or a metabolic inhibitor (e.g., to stop denitrification), or can be equipped with a filter to stop reactions, sterilize, or simplify post-deployment laboratory logistics [16] [3].

Solution Injection. At any time during deployment, a preloaded solution or suspension may be injected into any chamber with the installation of the above-described sampler. This includes a non-reactive tracer solution such as bromide, iodide, or even deionized water that can be used to calculate the volume of the chambers or physical mixing based on the mass balance of the excess amount present in the sealed chamber after versus before injection. This technique is well-known and may account for uncertainties with respect to the depth of penetration of each porthole or sediment surface topographical variability, which ultimately affects the chamber's incubation volume and, thus, the material accumulation rates. This mechanism may additionally be employed to introduce treatments for the purpose of conducting seafloor experiments. For example, alum, iron, clay, or calcium carbonate suspensions can be injected to evaluate nutrient phosphate sequestration [2], or isotopically labeled nutrients can be added to monitor specific biogeochemical processes, such as $N^{15}$—$NO_3^-$ to monitor denitrification rates [17].

Chamber Mixing. Chamber mixing may be implemented via the sampling/mixing pump integrated into the chamber assembly, which circulates water in the chamber with a turnover time of approximately 5-10 minutes. The flow mixes in the chamber with a horizontal diffuser to minimize undesired sediment resuspension. Gentle mixing of the chambers can ensure homogeneity to obtain representative samples, as is an established practice in the art, but sediment erosion can alternatively be deliberately induced at greater flow rates to quantify natural sediment shear-linked resuspension fluxes. Turbidity sensors can be installed directly in the chamber lid to quantify this level of resuspension, although targeting specific levels of resuspension is challenging [2]. The deliberate resuspension can be programmed to be activated at any point during any one of the incubations, and based on the turbidity sensor's output, the control software can regulate the flow rate of the sampling and mixing pump to maintain desired turbidity levels.

Example Platform Specification

In certain embodiments, the platform may be configured to be approximately 4 feet in diameter, 2.5 feet tall, and less than 200 pounds. Deployment of one or more platforms can be accomplished from a small boat in shallow water in a single outing (for example, similar-sized platforms are routinely deployed from a 26-foot center console boat with a Davit crane and a light-duty, battery-powered winch). The compact and user-friendly design of the platform may allow for several platforms to be deployed, thus offering improvements in not only temporal but also spatial coverage compared to existing benthic landers that conduct in situ benthic flux chamber incubations.

Maintenance. This system is relatively easy to clean and maintain by having only a single chamber instead of separate chambers for repeated or replicated measurements. The base template and the protective bumpers are simple (inexpensive) and can be replaced with relative ease if damaged. Biofouling-resistant plastic and rubber are used for both the chamber lid/cylinder gasket and cylinder/porthole gasket.

Example Continuous Incubation and Measurement Operation

The platform 100 can overcome the specific main constraints faced by conventional benthic flux landers that would prevent their adoption for applied monitoring. The platform 100 is designed with end-users in mind, so it is simple to program and operate, thus yielding relevant information for applied monitoring. It is essentially the first benthic flux sensing platform designed for sediment-centric scientists conducting fundamental research but also for operators less experienced with sediment research, such as environmental/water managers or aquaculturists.

When unimpeded sedimentation is required for obtaining accurate results for many applications with processes that occur on relatively rapid timescales (e.g., <1 week such as capturing dynamic benthic nutrient feedbacks such as those related to algae bloom death and decay), then current in situ benthic incubation seafloor lander platforms are not acceptable even if they allowed the re-opening the lid to reset and allow multiple incubations. The design of the platform (e.g., 100) enables each time series incubation to be minimally disrupted with a mostly "fresh" sediment column during each incubation.

For a 6-porthole design, for example, an 8-hour incubation can be conducted at the first position, and then the five remaining positions can be used once each, in series, every other day, to obtain benthic flux measurements with a frequency of 48 hours. On the $13^{th}$ day, the first porthole can be reused, and the set of portholes can be cycled through again. A 24-day incubation can be accomplished with <3% inhibition of depositing sediment with respect to having all chambers closed for the entire duration. The primary base template platform can be perforated to minimize biogeochemical effects from propagating to the underlying sediments, e.g., related to inducing anoxia. To ensure wide adoption, the platform is relatively compact and lightweight and can be deployed from a small boat, allowing deployment in shallower water bodies compared to most existing larger seafloor lander platforms that conduct benthic chamber incubations. Some documented exceptions include the Automatic Benthic Chamber (CBA) [15] and the Gottenberg small lander [2], but both still yield only a single benthic flux measurement per deployment. Unlike, to our knowledge, any sediment-incubating benthic landers to date, the platform can also conduct ambient bottom water incubations. This is critical for inshore or shallow-water monitoring, as there are certain processes contributing to the benthic fluxes beyond sediments. For example, nutrient uptake can be modified by benthic algae blooms or submerged aquatic vegetation, or dissolved oxygen consumption may be strongly linked to water column respiration instead of sediment respiration. The platform can double as a stationary platform to monitor other relevant parameters related to both sediments and the benthic boundary layer, e.g., those that serve as ancillary indicators of application-specific sediment properties.

The platform's design and initial implementation for long-term soluble reactive phosphorous monitoring (SRP or phosphate), as depicted in FIGS. 1A and 1B, is timely, given the recognition of the importance and demand for benthic phosphate fluxes in many applications (e.g., eutrophication and aquaculture monitoring), as well as the emergence of appropriate fluidic sensors.

To allow for improved sampling of sedimentary environments is a continuous, autonomous platform including a single chamber assembly, a center point wherein the single chamber assembly mechanically pivots around the center point, a base template having at least one porthole, and a rotating platform with power, control, and communications hardware. The example benthic lander platform is designed to fit the needs of everyday applied industry and regulatory monitoring programs by (1) being modular, easily deployable, and requiring minimal user training, (2) generating data requiring minimal post-processing, and (3) allowing long-term repeated measurements of both fluxes and background processes and conditions.

The platform 100 includes control and software infrastructure that is configured to control the platform. The software infrastructure may automate all aspects of the coding required for the platform's control and data acquisition systems. The only requirement for the user may be to define the deployment parameters; all motion, timing, acquisition, and logging commands are transparent to the user unless they specifically opt for more precise control.

The platform 100 may conduct repeated incubations not only of the sediments to obtain fluxes but also of the ambient bottom waters. Additionally, ambient bottom water measurements (non-incubated) may also be collected periodically by deliberately not sealing the chamber. These measurements are of particularly high utility for data interpretation immediately before and after incubation. Since the platform is configured to move the incubation chamber to a different location, each incubation may minimally affect the next incubation by not inhibiting sedimentation. A sampling flow cell in line with the fluidic pumping/mixing path that provides one or more sensors sequential access to chamber contents or ambient waters at all physical chamber positions is also included on the platform. Alternatively, sensors may also be embedded in the chamber lid to access the chamber contents. A table of example sensor choices, as shown in Table 1 (above), and as a non-exhaustive list, is provided to showcase the range of biogeochemical analyte fluxes potentially measurable using the platform.

Example Method of Operation

FIG. 4A illustrates the various deployment scenarios of the platform 100 in accordance with an illustrative embodiment. In some embodiments, the platform (e.g., 100) is referred to as the CAROSEL (Chamber Array for Observing Sediment Exchanges Long-term). The general method of deploying the lander includes connecting a main controller to the platform while the platform is on the deck of a boat using a serial/ethernet or WIFI/Bluetooth interface and a laptop or tablet computer. In certain embodiments, the platform can have its own software, e.g., a web-interface with an IP address. A user would then program the platform to start at a certain time, after a certain amount of time, or upon removing a magnetic trigger, which is a well-known method in the art. Multiple deployment scenarios are possible, as is typical for oceanographic deployments (FIG. 4A), with stored data obtainable upon the system's retrieval or alternatively in near real-time via the addition of shore-linked communication capabilities typical of oceanographic monitoring systems.

In shallow water, deployment can proceed via a davit crane with a winch or cable and a strong marine line or rope first connected to the top of the platform. The platform is then slowly lowered into place on the seafloor, consistent with the practice that is well-known in the art. The platform can then start independently and can be left to operate autonomously at the seafloor for the duration of the deployment. A user would return a few weeks later and repeat the steps in reverse to retrieve the platform. When a user connects to the platform when back on the boat deck, a user can check the status of the instrument to make sure it ran the entire duration, look at the data, check the battery voltage, etc. It is possible to collect any autonomously-acquired samples, replace the battery with a charged battery, clean any fouling, refill any sensor reagents, and deploy the platform again that same day.

In any shallow configuration, direct, near real-time data transfer to users on shore is possible via a cellular or satellite modem mounted on a fixed platform near the deployed platform (e.g., 100). Data may include either the raw concentration time series, processed derived fluxes, or both, although the latter is what is ultimately desirable from a typical user application standpoint. However, raw data can provide more troubleshooting capabilities, and indeed, two-way communication can allow troubleshooting and deployment configuration adjustments while the platform (e.g., 100) is still deployed. For example, if incubations are too long and chambers become anoxic during deployments, the deployment length can be reprogrammed remotely.

For deep waters, a user may also deploy the platform (e.g., 100) with an acoustic measurement or timed release, a method well-known in oceanographic operations. This method would require the attachment of both floats and sacrificial ballast weights to the platform. The platform can be lowered into place, and the line can be released with a quick release. In this embodiment, the platform can remain stationary and operate at the seafloor with no lines or buoys attached. When a user is ready to retrieve the platform, they may trigger a release by sending an acoustic signal from the boat through the water to the platform. This results in the extra ballast weights being dropped from the platform, which can subsequently float to the surface for retrieval. The weights are left to degrade on the seafloor. Preferably, the weights are made from scrap iron, which does not contribute to pollution. If near-real-time measurements are desired prior to retrieving the platform, it can be fitted with an acoustic beacon and/or modem to allow a periodic visit by an autonomous vehicle. The vehicle can download data from an acoustic modem on the platform (e.g., 100) and then subsequently surface and transmit data back to shore via satellite communications.

If it is desired that the system interfaces with an existing fixed-location sensor suite to provide this external sensor suite with new benthic flux monitoring capabilities, divers may be required immediately after deployment to connect the platform's primary mixing/sampling fluidic path (e.g., the flow cell manifold) with the respective external sensor sample intake(s) or sensor head. This can be accomplished with the design of sensor-specific adaptors to allow easy connection of the sensor intake/head with the platform's fluidic path.

In the top diagram (labeled "Buoyed shallow water deployment"), an example method is shown for a typical shallow deployment in which the platform 100 is programmed onboard the ship or boat and deployed unattended until retrieval.

The platform 100 can also be deployed in deeper waters as a free vehicle, where longer lengths of a tether line may be cost or logistically prohibitive. While the structure is by default positively buoyant due to the addition of buoys, it is made negatively buoyant for the duration of the deployment by adding ballast weights. The weights are then jettisoned at the desired retrieval time by a timed release or acoustic release so that the platform then floats to the surface for retrieval by the operators. In the second panel (labeled "free-vehicle deep version"), the method is shown for deeper water operation in which the platform 100 is deployed as an initially negatively buoyant free-vehicle. Immediately prior to retrieval, the platform 100 is configured to release its scrap ballast weight and return to the surface for retrieval.

In another deployment mode, the platform can be tethered to a surface buoy or fixed structure with remote communication capability to allow transmission of data to the operator in near-real time.

In another deployment mode (labeled "Ocean Observing Network: Autonomous Vehicle retrieval"), the method is shown for longer duration monitoring in which real-time data is desired, but no ocean surface communications are present. In this example, an autonomous underwater vehicle or autonomous surface vehicle can periodically collect data from the platform 100, e.g., with an underwater modem, and relay the data to the satellite upon surfacing for ultimate transmittal to shore.

In the fourth diagram (labeled "Ocean Observing Network: Permanent installation"), the method is shown for shallow water or cabled observatory systems. In this example, the platform 100 is configured to be deployed as part of a fixed location installation, e.g., equipped with power (solar) and communications infrastructure that can relay information to shore. In some embodiments, the sensor can be powered directly from shore via a local energy storage module (e.g., battery or A/C power) and can store data only locally until retrieval.

In an alternate embodiment, an existing sensor suite that is already monitoring water column parameters, e.g., as part of an ocean observing system, can be conferred the capability to monitor benthic fluxes by interfacing it with the platform (FIG. 4A, bottom panel). The platform is deployed adjacent to this sensor suite, and the platform's mixing/sampling pump is fluidically interfaced with the sample intake system of the existing external sensor suite so that this external sensor suite now essentially conducts periodic measurements of the circulating chamber contents. While the external sensor suite can still conduct ambient water column measurements as originally intended (i.e., during instances when the platform's chamber lid is in the open position), the system would sacrifice the ability to conduct ambient measurements while the platform is conducting the incubations, thus creating gaps in the time series ambient concentration data. In this deployment mode, both the platform's mechanics and the external sensor suite can operate completely independently relative to one another, so long as the platform's chamber position is known at any time during which the external sensor suite collects a sample. For example, if the external sensor suite is designed to sample on the hour, every hour, then the platform can be programmed to transition between incubation/ambient sample routines around this constraint. The external sensor suite can still remotely transmit data to the operator, as before the modification.

In the fifth diagram (labeled "Ocean Observing Network: Augmenting existing sensor . . . "), the platform 100 is shown deployed adjacent to an existing ocean-observing sensor suite, and the external sensor suite is fluidically connected to the platform to intake samples from the recirculating chamber waters via the platform's flow cell. The platform 100 can be programmed to operate independently from this external sensor suite or can be synched and controlled by this external sensor suite.

Multiple benthic incubations can be conducted over a period of days to weeks (e.g., 6 to 12 time points) while minimally impeding horizontal advection and the natural sedimentation or deposition and resuspension processes between time points. These processes are important drivers of temporal variation. Instead of having multiple independent benthic chambers, the fundamental mechanism is a single chamber assembly (lid and cylinder) that mechanically pivots around a center point by use of a motorized rotary stage and can be lowered into place (via actuation) to start an incubation, although other mechanisms are also possible, such as cartesian manipulation within a "checkerboard"-like 2-dimensional horizontal grid of portholes via a motorized 3-axis linear positioning system. Furthermore, the chamber, e.g., via the porthole configuration, is not inserted directly into the sediments due to risks involving undesirable carryover and contamination of sediments into subsequent incubations.

Figure 4B:
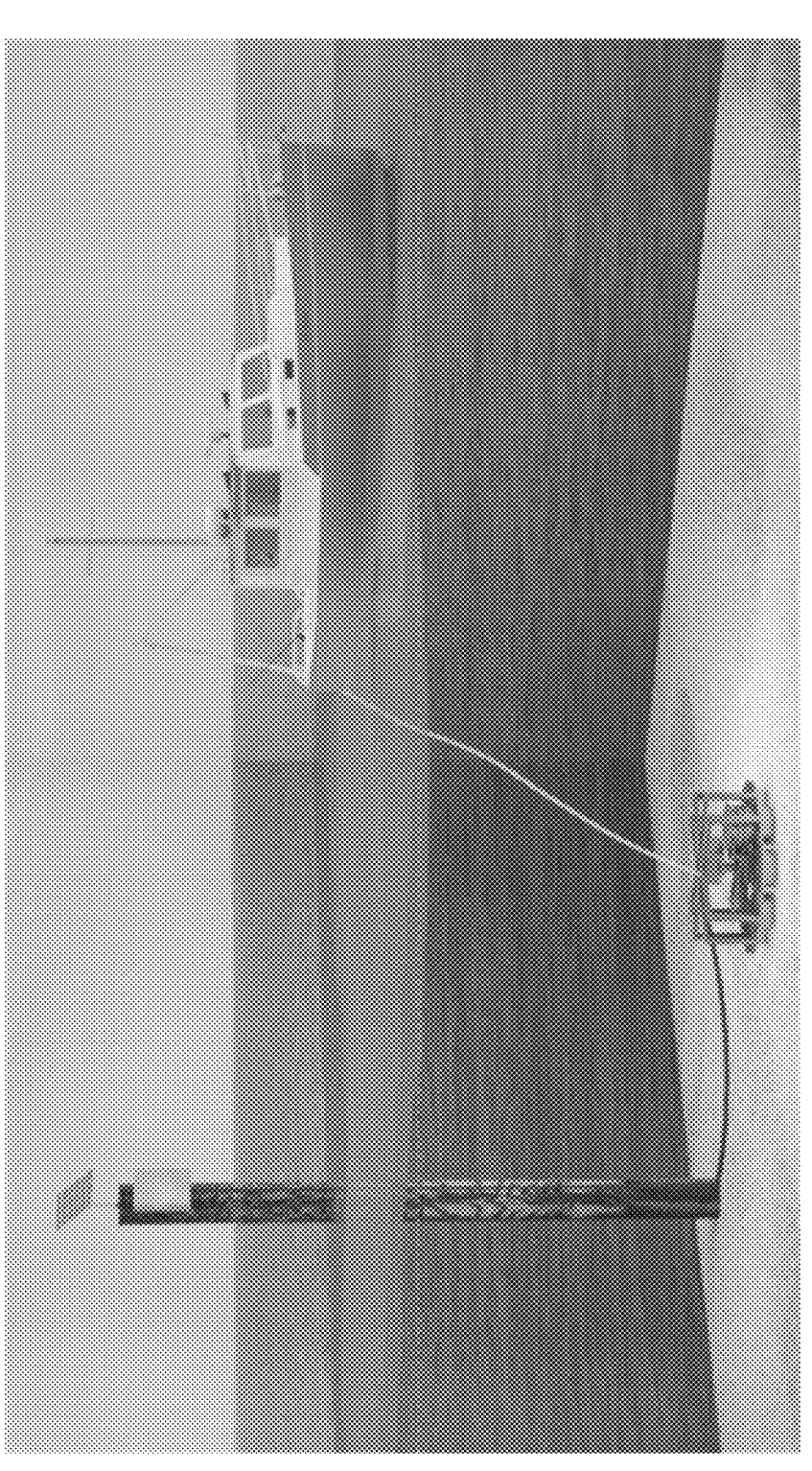
FIG. 4B illustrates an example deployment scenario of the platform in accordance with an illustrative embodiment.

FIG. 4B illustrates an example deployment scenario of the platform in accordance with an illustrative embodiment. In FIG. 4B, the platform is shown being deployed and retrieved via a vessel and is allowed to operate independently via a solar/communication module.

Example Applications

The exemplary platform (e.g., 100a, 100b) can be used for a number of measurement applications. Table 4 shows examples of onboard or external sensor configuration packages that could be implemented using the exemplary platform (e.g., 100a, 100b) to accomplish the respective application-specific objectives.

TABLE 4

| | Monitoring objective | Recommended analytes | Sensor brand/model |
|---|---|---|---|
| Example #1 | Eutrophication Harmful Algal Bloom Hypoxia | Dissolved oxygen Redox analytes (including hydrogen sulfide) Nitrate + nitrite Phosphate Ammonium | Aanderaa optode Analytical Instrument Systems ISEA-X with Hg/Au electrodes Clearwater sensors Nitrate + Nitrite Clearwater sensors Phosphate Clearwater sensors Ammonium (expected 2023) |
| Example #2 | Carbon mitigation Ocean acidification | pH pCO2 Dissolved organic carbon Methane | ANB Sensors OC300 Sunburst SAMI-CO2 Seabird BB3 (with CDOM fluorescence and established fluorescence/DOC proxy) Pro-Oceanus Mini CH4 |
| Example #3 | Contaminants | Heavy metals (e.g., Hg, Pb, Zn, Cd), hydrogen sulfide, dissolved oxygen Multiple, via direct water sampling and post-retrieval analyses | Analytical Instrument Systems ISEA-X with Hg/Au electrodes McLane Remote Access Sampler |

Other configurations may be employed, e.g., using the sensors described herein.

Example Benthic Measurement Data Portal

The systems, methods, and devices disclosed herein (e.g., the platform 100 of FIGS. 1A and 1B) may produce, compile, and deliver data to a local or remote server for visualization. For example, this disclosure contemplates a data visualization tool including a data portal (e.g., a web-based data portal) for selectively and easily visualizing the compiled and/or processed data from the platform 100.

Figure 5:
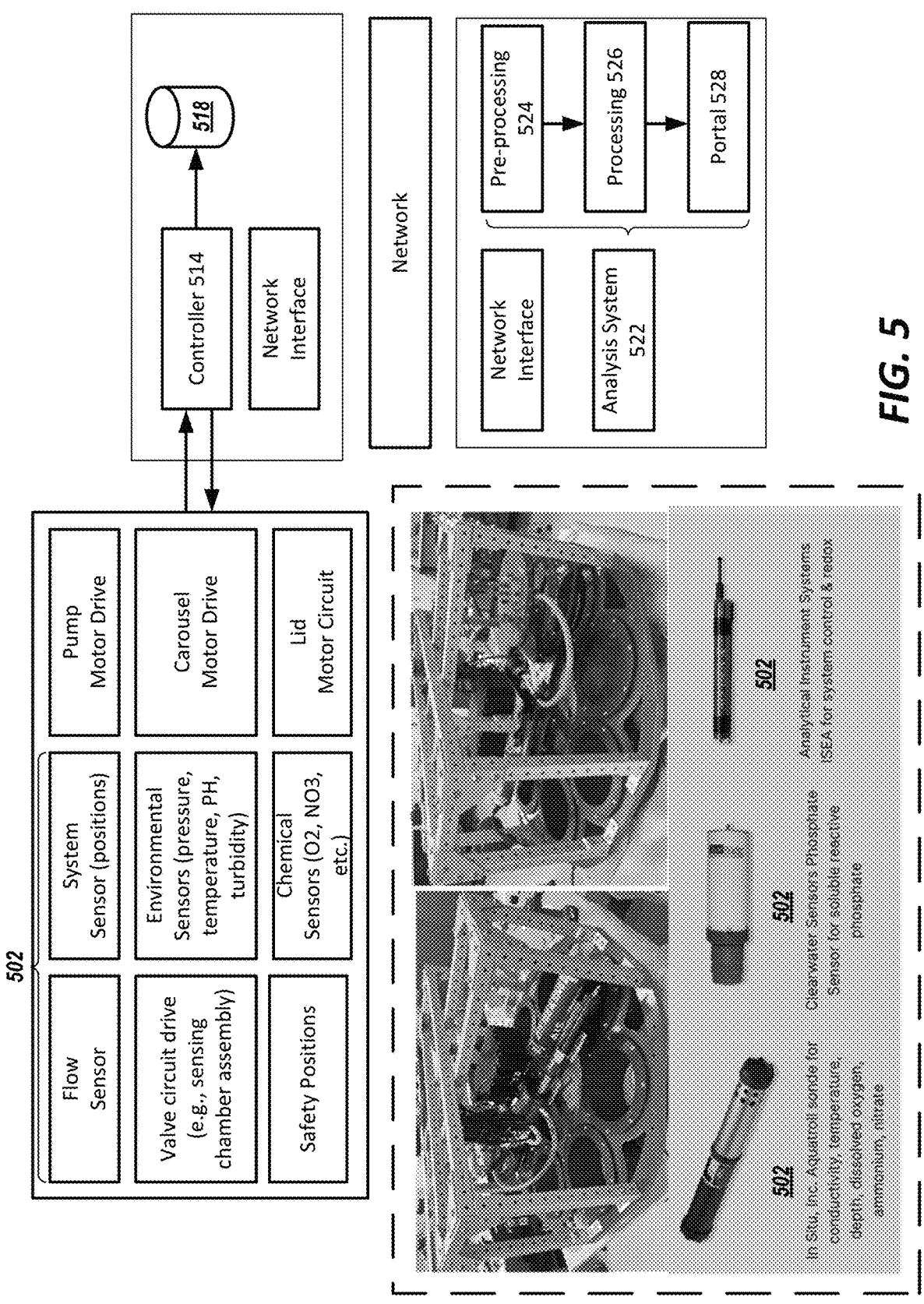
FIG. 5 shows an experimental/prototypical embodiment of a platform of this disclosure. in accordance with an illustrative embodiment.

FIG. 5 shows an example control system 500 for the exemplary platform. In the example shown in FIG. 5, the control system 500 of the platform (e.g., 100) includes a suite of sensors 502, a sensor interface or controller 514, and a data store 518.

The suite of sensors 502 includes (1) sensors for the measurement of sample conductivity, sample temperature, sample depth, sample dissolved oxygen, sample ammonium concentration, sample nitrate concentration, sample soluble reactive phosphate concentration, sample dissolved oxygen concentration, sample hydrogen sulfide concentration, and sample sediment respiration indicators, e.g., dissolved iron (II) and manganese(II) concentration. In other implementations, the platform 100 includes a suite of sensors, including additional or alternative data collection and transmission devices, as previously described and listed in Table 1.

In some embodiments, the sensor interface or controller 514 is configured (as a sensor controller or as a sensor interface) to connect to a remote monitoring station or receiver station that is configured to function as the data store 518. In other embodiments, the controller 514 is configured to connect to integrated or ruggedized data acquisition hardware on the platform 100 (not shown).

The sensors 502 of the platform 100 are configured to measure data in any one of a variety of methods/operations described herein. For example, FIG. 4A and its corresponding description provide exemplary data collection/retrieval systems. These include local storage (e.g., on a memory/processor of the platform), remote storage (e.g., cloud-based storage), local transmission (e.g., direct connection or close-range communication), and long-range transmission (e.g., via satellite), among other options. In some embodiments, the sensor interface or controller 514 includes components and integrating circuitries to facilitate connection to a computer.

The data store 518 may provide the acquired sensor data to an analysis system 522 located locally or external to the platform, the analysis system 522 is configured to generate, for example, a benthic flux value from the sensor data. In FIG. 5, the analysis system 522 is shown as a part of the receiving station or localized controller (e.g., on a boat or nearby buoy). In other embodiments, the analysis system 522 may be remote to the platform 100, and the associated infrastructure (e.g., a server or a cloud infrastructure that is configured to receive the acquired sensor data to analyze for the benthic flux, rate of photosynthesis, and other values and trends of interest).

The analysis system 522 may include a pre-processing step 524 wherein the raw sensor data is compiled and processed according to a desired value or operation (e.g., normalizing or averaging certain values over time). Then, the analysis system 522 is configured to perform data processing operation at the processing step 526. At the processing step 526, the analysis system 522 processes and manipulates the raw data to produce values of interest. For example, the processing step 526 may calculate the flux time series of several different analytes (such as dissolved oxygen, nitrate, or ammonium, as shown in the example display portal in FIG. 6). The values calculated and derived by the analysis system 522 at the processing step may be displayed on a series of graphs and plots (including raw data, calculated data, or both) at the display step 528 in FIG. 5. Such data display may be a comprehensive Data Visualization Portal accessible by users of the platform 100 and other researchers or users. An example data visualization portal from the display step 528 is shown in FIG. 6.

Web-Based Data Portal. In one example, the data and data products obtained with the platform 100 are best visualized via a web-based cloud visualization and control portal that receives near-real-time raw or processed data via a telemetry system (e.g., from the data processing shown in FIG. 5) and also allows two-way communications to enable control adjustments to the deployment parameters. Alternatively, the platform 100 may itself host a potentially simplified version of this software that can be accessed via direct connection with, for example, ethernet or serial communications. Each user of the platform 100 may have a proprietary version of the display that contains only information from their own deployed sensors (and any relevant publicly available external data sources), or the user can opt to share the platform 100 data sets with other platform users to create a larger database.

Externally available data sources may also be included, such as satellite maps of parameters such as true color, chlorophyll, turbidity, or dissolved organic carbon, as well as nearby river flows and time-series water quality concentrations, stationary buoys, or even mobile autonomous monitoring platforms.

Software Display and Associated Data Product Information. The web-based data portal and associated software can display several types of information at once and may allow a user to manipulate the data or display in numerous ways, including, e.g., map-based and tabular displays of the water body with deployed platforms indicated by geographically-distributed icons. The user may select a specific individual deployment icon, which can populate tabular and graphical information on the remainder of the visualization portal specific to that selected site. The icons themselves may be colored or have shapes or sizes indicative (e.g., proportional) of a specific measurement, such as the measured benthic flux or any other parameter specific to that site. The map background or overlay may be colored or shaded according to externally-acquired remote sensing data acquired by, for example, satellite or drone, allowing comparison to, for example, spatially measured benthic flux and chlorophyll to determine if there is any direct relationship in which benthic fluxes are affecting the distribution of harmful algal populations or oceanic and atmospheric carbon distributions. Also, on the map, external point sources such as river inputs may be displayed or selectable to allow river flow or associated parameters to populate the remainder of the visualization portal. Additionally, external data sources such as meteorological, oceanographic, or water quality buoys may also be selectable and enable population.

The web-based data portal and associated software may include, when a platform or external information source/site is selected, a table that provides the most recent status and set of measurements from that source. The user may use a slider feature to cycle through historical measurements. For the platform 100, this information may contain the date and time of the measurement, the chamber position at that time (e.g., ambient water measurement, benthic flux incubation, ambient water incubation), and any sensor measurements for that time, either deployed within the benthic chamber or externally.

The web-based data portal and associated software may include, when a platform 100 or external information source/site is selected, time series graphs of the raw data output from sensors equipped on that specific platform that are populated on the visualization portal. Each sensor's data can be continuous regardless of whether the platform 100 is changing the chamber position (e.g., ambient water measurement, benthic flux incubation, ambient water incubation), although the data symbol on the graphs may change according to the chamber position. For example, the time series for a chemical analyte expected to flux from the sediment and thus accumulate in the chamber may be displayed at 30-minute intervals (the sensor operational frequency) with time on the x-axis and chemical concentration on the y-axis, in which concentration measurements increase for six hours during a benthic flux incubation (indicated by discrete data points corresponding the platform 100 incubation portal location number that is active, e.g., "2"). Then, concentrations reset to baseline conditions for a short period of time when the chamber is opened and reset (indicated by discrete "O" symbols). Then, concentrations increase for the next six hours, although at a slower rate, when the chamber is conducting an ambient water incubation isolated from the sediments (discrete data symbols indicated by a "6" symbol, assuming position #6 is that in which a plate is used to isolate the chamber from the sediments during an ambient water incubation). This display format is useful for a rapid visualization of platform 100 functionality and to ensure appropriate behavior of the chemical analytes in the chamber as expected during operation. The user can use data and time sliders to visualize historical data.

The web-based data portal and associated software may include user-selectable input, e.g., via toggle switches, to overlay on the above raw data chemical concentration time-series graphs the computationally auto-fitted rate of change (linear or otherwise) that is used for flux calculations. This can ensure that the fits are appropriate, and any QA/QC error checking that is detected during the fitting routines may also be indicated by a different line color or dash type corresponding to that specific error. Options to conduct corrections, such as manual fitting, may also be provided.

The web-based data portal and associated software may include the fitted rates of change, as above, to populate another set of derived flux graphs with a different timescale than the raw data. For example, whereas raw data may be collected every 30 minutes as limited by the sensor response frequency, each incubation that yields a single benthic flux measurement may last six hours, and thus, this new set of graphs can have an x-axis tick mark frequency on this latter order and an overall range of several weeks (although the user can select the range with sliders). At least three types of fluxes can be displayed per analyte on separate time-series plots or on the same plot as indicated using different symbols or colors, with the x-axis corresponding to date/time and the y-axis in units of moles or grams per sediment surface area per unit time. Benthic Fluxes can be determined from the rate of change of an analyte in which the chamber is sealed on a porthole that is not isolated from the sediments and thus is influenced by both the encapsulated water and sediments (corresponding to the more conventional benthic fluxes used in this discipline). Water fluxes correspond to the rate of change of analytes during Ambient Water Incubations in which the chamber is sealed on a porthole that is otherwise isolated from the sediments (e.g. with a solid plate). Because these two fluxes are inherently normalized to the sediment surface area and are independent of any chamber volume changes, the system can derive a "true" sediment flux by difference, which represents only the fluxes from the sediments. This true sediment flux is valuable information for water researchers and is superior to conventional benthic flux measurements, which cannot isolate the influence of convoluting water column-located processes.

The web-based data portal and associated software may include graphs or tabular data containing Derived Data Products that are populated using the transformation of any or all of the information as described above (i.e., external data sources, sensor measurements from platform 100, or derived flux measurements). These are described in more detail below.

FIGS. 6A-6E show an example benthic measurement data portal 600 with simulated data, e.g., as curated by portal 528.

Figure 6A:
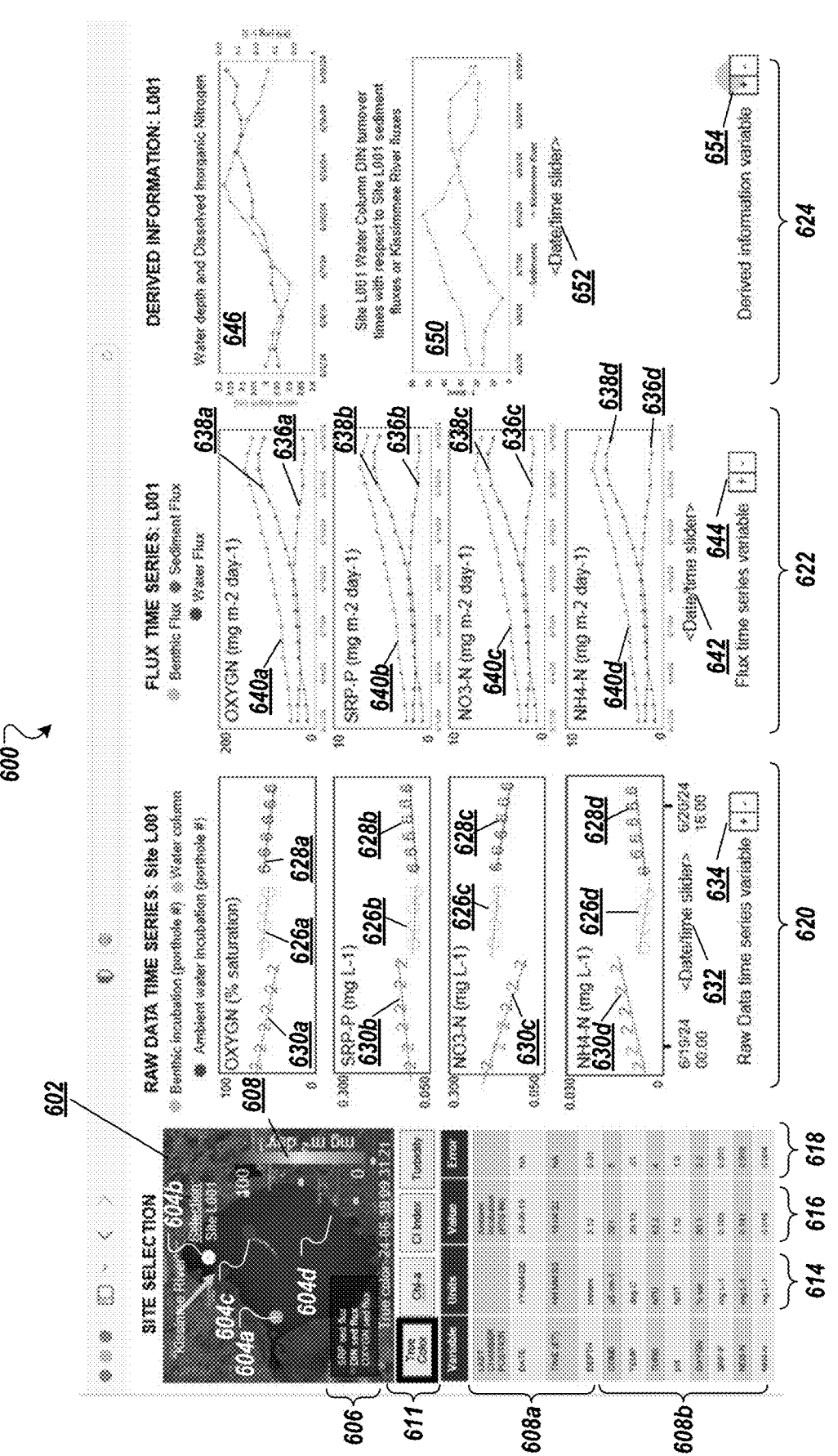
FIGS. 6A-6E show an example data portal for visualization of the measurement by the benthic lander platform in accordance with an illustrative embodiment.

FIG. 6A shows a combined view of the data portal 600. FIGS. 6B, 6C, 6D, and 6E show sub-sections of the views of FIGS. 6A, again all with simulated data.

Figure 6B:
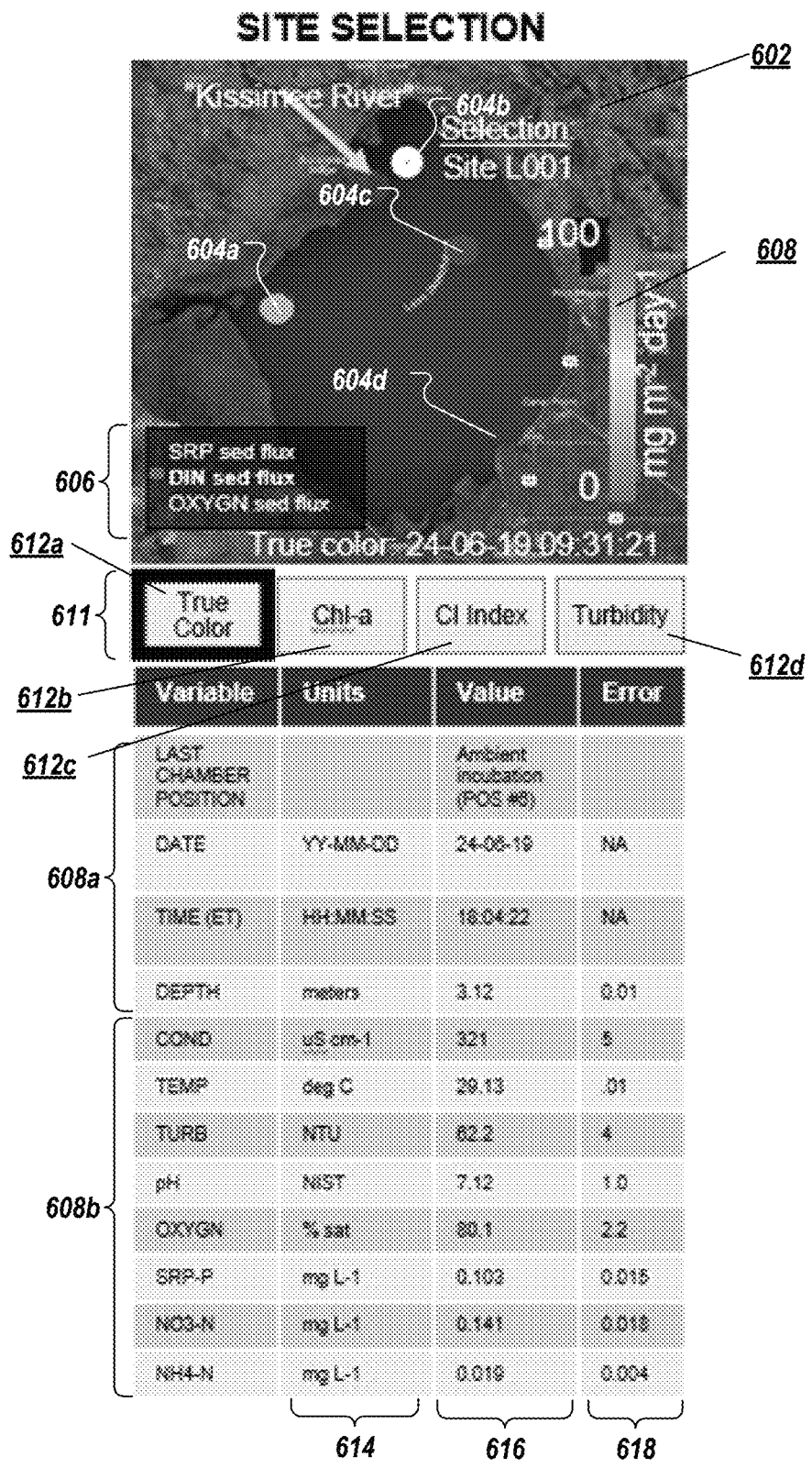

In the example shown in FIG. 6A, as shown in FIG. 6B, the data portal 600 includes a map display 602 generated from a map API having a selectable set of sites 604 (shown as 604a, 604b, 604c, 604d, corresponding to 4 platforms in this example) to which data is available. The type of data for the sites (e.g., 604a-604d) may be toggled per widget 606 (e.g., soluble reactive phosphorus sedimentary flux "SRP sed flux," dissolved inorganic nitrogen sedimentary flux ("DIN sed flux"), and dissolved oxygen sedimentary flux "OXYGN sed flux"), with the corresponding concentration based on a color code (e.g., mg/day·m²); the color having a quantitative scale shown per legend 608. In the example, the "DIN sed flux" data is selected, so such data values are used to color the four icons.

The most-recent values 608 for the measurement at the site are also shown in FIG. 6B. In the example, the environment measurements 608a are shown, including chamber position identifier (shown as "Ambient Incubation (POS #6)"), measurement date (shown as "24-06-19"), measurement time (shown as "18:04:22"), sample depth (shown as "3.12" meters) are presented. The chemical measurements 608b are also shown, including sample conductivity (shown as "321" uS cm⁻¹), sample temperature (shown as "29.13" ° C.), sample turbidity (shown as "62.2" NTU), sample pH (shown as "7.12"), sample dissolved oxygen saturation (shown as "80.1" % sat), sample soluble reactive phosphorus "SRP-P" (shown as "0.103" ml/L), sample nitrate/NO3-N concentration (shown as "0.141" ml/L), and sample ammonium/NH4-N concentration (shown as "0.019" mg/L). The display can provide the units 614, the values 616, and the errors/uncertainties of the measurement 618.

The display 600 allows the selection among different airborne/satellite remote sensing data types 611 (shown as "true color" 612a, a type of satellite optical measurement), chlorophyll-a (shown as "Chl-a" 612b), cyanobacterial index (shown as "CI index" 614c), and turbidity (shown as "Turbidity" 612d).

The display 600 can provide the hourly-scale raw data over the course of a day or sub-day in time series plots 620, the inferred, calculated flux data over the course of weeks or months (in this case one incubation of each type Benthic and Ambient are conducted daily) in time series plots 622, and most useful, the derived daily information determined for a period of month or weeks in plots 624.

Figure 6C:
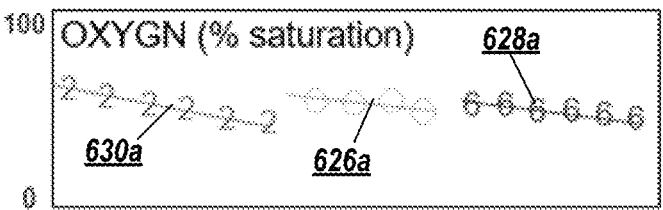
Figure 6C:
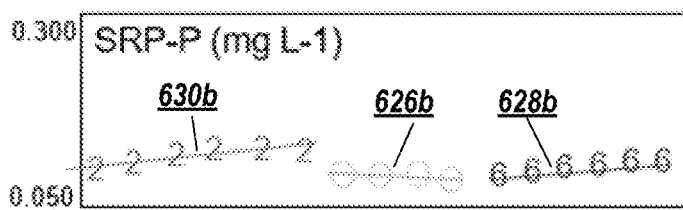
Figure 6C:
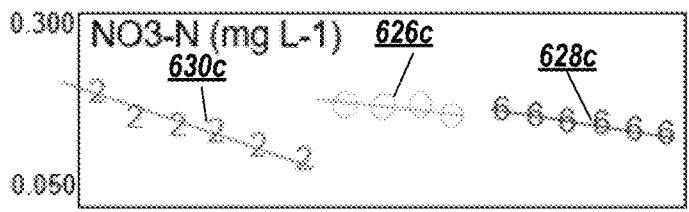
Figure 6C:
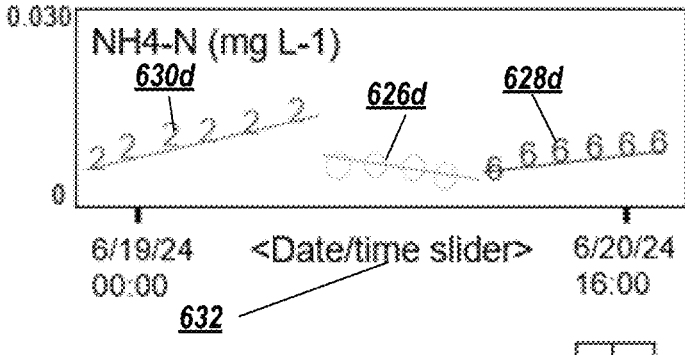

Raw time series data. In FIG. 6A, as shown in FIG. 6C, the raw data time series plots 620 plots provide the benthic incubation 630a-630d, the ambient water incubation (628a-628d), and water column measurements (626a-626d) for the current sampling position over a period of time (e.g., last 12 hours of measurements). Plots 620 includes subplots for dissolved oxygen concentration (626a, 628a, 630a), soluble reactive phosphorus "SRP-P" (626b, 628b, 630b), nitrate NO3-N (626c, 628c, 630c), and ammonium NH₄ (626d, 628d, 630d). The data symbols themselves each correspond to the chamber position at the time that measurement was collected, e.g., shown as position "2" (630, for benthic incubation), position "6" (628, for ambient water incubation), or position "O" (for open chamber ambient water measurements) (626). The "water column" measurements correspond to open chamber measurements, and the "ambient water incubations" correspond to sediment-isolated incubation measurements. In the example shown in FIG. 6A, four data points of the benthic incubation are shown, four data points of the water-column measurements are shown, and four data points of the ambient water incubation measurements are shown. The period of time is adjustable in scale and can be panned via data/time slider input 632. The presented measurement time series variables can be modified (added/removed) via input 634.

The plots 620 in combining the three measurement types in a single visualization output allows a more readily interpretable analysis of changes and trends in the various measurements. It is contemplated that other visualizations can be used, e.g., presenting each of the measurement types in its own plots.

Figure 6D:
Figure 6D:
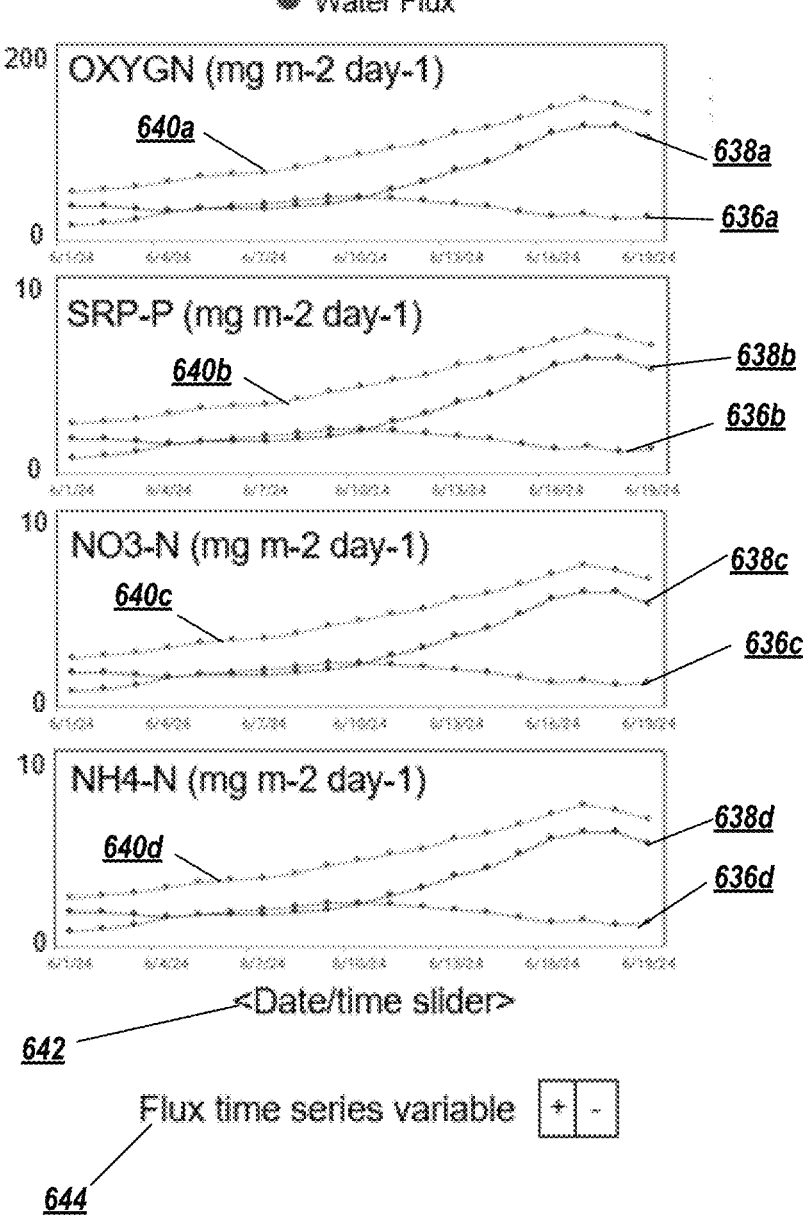

Flux visualization. In the example shown in FIG. 6A, as shown in FIG. 6D, visualization of fluxes calculated from each of the paired benthic incubation 630 and ambient water incubation 628 time series are presented as daily flux data (i.e., one type of each incubation was performed daily) over the course of a month or weeks in plots 622. The total flux (640) corresponds directly to the results of the benthic incubations, the water column flux (636) corresponds directly to the results of the ambient water column incubations, and the sediment (only) flux (638) corresponds to the difference 638 minus 636. Plots 622 includes subplots for dissolved oxygen fluxes (636a, 638a, 640a), soluble reactive phosphorus fluxes ("SRP-P fluxes" 636b, 638b, 640b), nitrate fluxes NO3 (636c, 638c, 640c), and ammonium fluxes ("NH4 fluxes" 636d, 638d, 640d). The period of time is adjustable in scale and can be panned via data/time slider input 642. The presented measurements can be modified (added/removed) via input 644.

Long-term trend visualization. The web-based data portal and associated software may include long-term time-scale visualization to examine seasonal and annual trends, e.g., as influenced by land-use change, water management practices, or climatic patterns. Water managers are also interested in knowing the relative annualized contribution of nutrients to a water body from the underlying sediment-derived flux in comparison to that from an external source, e.g., dominant river inputs. Alternative applications are also possible, including any of those in Table 4. For example, global carbon emissions (fluxes) are often reported over annual timescales, and the platform 100 provides sufficient temporal granularity for comparison to other carbon sources, while long-term visualizations again reveal seasonal influences.

Figure 6E:
Figure 6E:
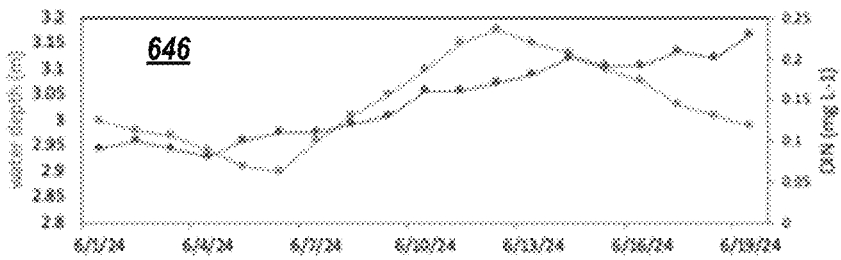
Figure 6E:
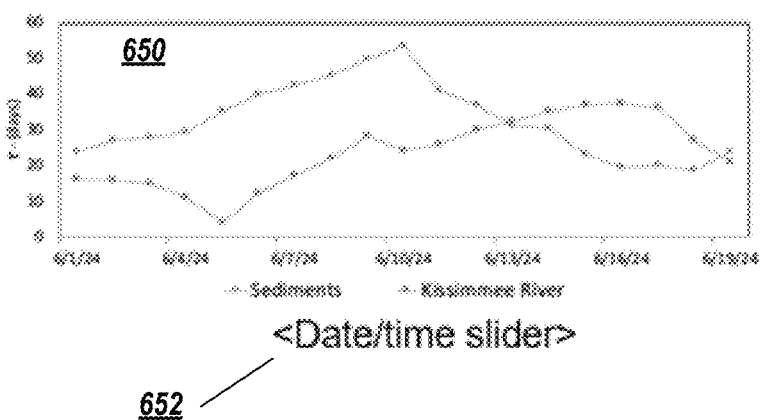
Figure 6E:

FIG. 6A, as shown in FIG. 6E, presents visualization of the most potentially impactful information derived from platform 100 benthic flux and ancillary data, as well as external data that is often available publicly from, e.g., water management or ocean-observing agencies. Daily information determined for a period of month or weeks are presented in plots 624, including a measured water depth and dissolved inorganic nitrogen plot 646, and relative water column turnover time plot 650. The period of time is adjustable in scale and can be panned via data/time slider input 652. The presented measurements can be modified (added/removed) via input 654.

The "true" Sediment Flux (determined by the difference between the Benthic Flux Incubations and the Ambient Water Incubations) is valuable information for water researchers and is superior to conventional benthic flux measurements, which cannot isolate the influence of water column-located processes. For example, over long-term time scales, a water management agency may be interested in knowing the relative annualized contribution of phosphate to a lake from the underlying sediment-derived phosphate flux in comparison to that from an external source, e.g., a dominant river input. In this case, for a time-series set (or array) of Sediment Flux measurements acquired daily for an extended period of time (e.g., one year with fluxes in units of moles/m²·day collected at daily intervals) annualized sediment loading in units of moles for a water body with a variable surface area S.A. in units of m² is determined per Equation 1.

$$\text{Annual Sediment Loading} = \int_1^{365} S.A.(t) \times SedimentFlux(t)dt \qquad \text{(Eq. 1)}$$

In Equation 1, while an integration is shown, the operator can be a summation of the data over the noted period. For the River Flux, loading is defined as the volumetric flow rate Q (m³/year), which is often measured hourly and reported in units of cubic feet or meters per second, multiplied by the corresponding concentration of phosphate in the river water $C_{River}$ (moles per m³). These parameters are typically reported hourly by the responsible monitoring agency, resulting in 8,760 measurements per year, and this information is often publicly available. Thus, the Annual River Loading can be defined per Equation 2.

$$\text{Annual River Loading} \int_1^{8,760} Q(t) \times C_{River}(t)dt \qquad \text{(Eq. 2)}$$

In Equation 2, while an integration is shown, the operator can be a summation of the data over the noted period. With the normalization of the Sediment Flux and River Flux loading to equivalent annual timescales, water managers can weigh decisions regarding where to focus funding and efforts in an attempt to improve water quality. If the total goal is to remove or offset the greatest magnitude of phosphate via nutrient control technologies, then the relative nutrient-removal efficiency of both of these technologies can be weighed against the cost to determine the most appropriate course of action. Assuming, for example, that the goal is to remove the maximum amount of nutrients entering the water body, then if the Annualized Sediment Flux is much greater than the Annualized River Flux, nutrient removal via dredging sediments may be a much more viable solution than adding phosphorous-adsorbing pellets in the river if the costs are similar. Substantial federal, state, and municipal funding is expended for nutrient removal and thus the platform 100 and derived data products provides critical information otherwise unobtainable from conventional techniques.

Relative water column turnover time plot (650). While the cumulative sediment loading calculation may be useful to obtain high-level information about the relative magnitude of inputs to a water body, it does not consider if that magnitude of the sediment flux is actually significant with respect to the water column inventory. For the phosphate example, even if sediment phosphate fluxes into a lake are larger than a river flux, they may not be impactful if the overall water column volume and/or water column nutrient inventory is large. To this end, the platform can also output the turnover time of the water column nutrient inventory with respect to sediment flux inputs by using the Ambient Water Column Measurements feature (i.e., measurements obtained deliberately in the unsealed/open chamber position), along with a simple water pressure-based depth sensor equipped onto the platform to derive a time-series water depth vector D in units of meters.

Ambient Water Column Measurements (producing a time-series vector CWC) can be obtained more frequently (e.g., 30-minute frequency) than fluxes determined through a Benthic or Ambient Water Column Incubation as these latter two only yield a single flux over the course of an incubation; however, these Ambient Water Column Measurements are only obtained when incubations are not being conducted. Ideally, the Ambient Water Column Measurements can be conducted both immediately before and after a completed set of a sequential Benthic Incubation and an Ambient Water Column Incubation. If one assumes a column of water overlying a sediment cross-sectional surface area (set to equal 1 m²) and depth D (in meters), then this volume is D m³. If the time series of Ambient Water Column Concentration measurements (CWC), output in units of moles/L directly by the instrument is now transformed via multiplication by 1,000 to yield moles/m³, then the water column molar inventory at time-series element/is determined via the product $D \times C_{WC}$, although this assumes a vertically well-mixed water column.

Water depth and dissolved inorganic nitrogen plot (646). Plot 646 can show an example of water depth and dissolved inorganic nitrogen (DIN) data (obtained from the sum of concentrations of ammonium and nitrate sensors equipped on the platform 100, e.g., those in Table 4 for the Eutrophication monitoring application). In the example, the data is shown as daily, but there can actually be multiple measurements per day at 30-minute intervals, except when incubations are being performed. Depending on platform 100 programming, one may expect to obtain consecutive water column concentration measurements for ~12 hours (at 30-minute intervals), and then a Benthic Chamber Incubation and Ambient Water Incubation each performed for the remaining 12 hours, during which time Ambient Water Concentration measurements are not conducted as the chamber can be closed and not equilibrated with the external ambient water. In plot 646, the multiplication of the water depth by the water column DIN (converting the Water Column DIN to mg per m³ instead of mg per L) would provide the water column inventory, which can be additionally displayed (not shown).

For the two DIN concentration measurements bookending the consecutive Benthic Incubation and Ambient Water Column Incubation, the average can be determined and multiplied by the depth to determine the inventory, as in the numerator below. The turnover time (τ) (e.g., for plot 650) at time-series element i can be determined by dividing the average water column molar inventory (i.e., the presumed temporal midpoint before and after the incubations) by the Sediment Flux (i.e., the Benthic Flux minus Water Column Flux) per Equation 3.

$$\tau(i) = \frac{\left(\frac{[D(i-1)C_{WC}(i-1) + D(i+1)C_{WC}(i+1)]}{2}\right)}{SedFlux(i)} \qquad \text{(Eq. 3)}$$

The turnover time (e.g., 650) is an actionable metric, particularly for short-term environmental management response decision-making. Short turnover times essentially indicate that the sediment fluxes are dominating the water column chemistry at that moment in time. After sustained monitoring of a water body of interest, specific thresholds may emerge that have a predictive capacity to select for, e.g., harmful algal bloom species, given that most lakes experiencing these blooms are shallow and turbid (i.e., influenced by the benthos). The sediment influence is not seasonally constant, and thus, temporal variabilities in turnover times may be a powerful predictive indicator variable that does not require extensive ancillary modeling techniques otherwise designed to understand the short-term regulators of harmful algal blooms. Furthermore, turnover times of the water column nutrient inventory may be determined with respect to river nutrient inputs if an appropriate river/water body mixing area and volume are assumed. This now provides a path towards evaluating the dominant control on biological nutrient availability. The turnover time plot may also be useful for other analytes such as dissolved oxygen when evaluating the Sediment Oxygen Demand. If sediments are drawing down the dissolved oxygen rapidly, e.g., due to high respiration and stagnant waters not well-mixed with the atmosphere, then a potential course of action would be to modulate water control structures to encourage mixing. A resulting water column DIN turnover time graph (650) is shown in FIG. 6 in the right column, bottom graph, with associated label.

The data plot uses, as an example, externally-ingested Kissimmee River flow and DIN concentration data (per the user-selectable River in 602) and all three types of platform 100 data generated types (Benthic Incubations, Ambient Water Column Incubations, and Water Column Concentration measurements), demonstrating the ultimate utility of the platform 100 measurements.

Additional Data Product: Nutrient input ratios. A commonly used metric to evaluate the nutrient ecological status of a water body is the nitrogen-to-phosphorous ratio. At high N:P ratios, the formation of harmful algal blooms is more likely. The commonly accepted N:P molar ratio of phytoplankton is 16:1 (the Redfield Ratio). While this mostly applies to water column chemistry, if instantaneous sediment nutrient flux inputs of dissolved inorganic, organic, or total N and P, are greater than or less than this ratio, then the sediments can be perceived as an influence that would affect the overlying water body system to either encourage or discourage the formation of harmful algal blooms. The generalization of this ratio approach for other analytes beyond N and P is possible. For example, for carbon monitoring, the sediment flux ratio of alkalinity to dissolved inorganic carbon can influence the pH and carbon storage capacity of the overlying water body. This knowledge may enable decision making regarding $CO_2$ mitigation strategies, e.g. to adjust alkalinity via mineral additions or electrochemical techniques to retain inorganic carbon in the dissolved state.

Additional Data Product: Photosynthesis and Respiration. If the single benthic chamber is transparent or if two separate chambers are used (transparent and opaque), then it is possible to isolate fluxes resulting from benthic respiration and photosynthetic processes. For embodiments with only a single transparent chamber, then night-time incubations substitute for the "dark" chamber and day-time incubations for "light" incubations. It is common practice in this discipline to inhibit photosynthetic processes by conducting night-time incubations, allowing inference of flux processes linked to benthic respiration. Alternatively, light incubations allow both benthic respiration and photosynthesis to occur simultaneously, and thus photosynthesis-linked processes can be inferred by difference. The platform 100 can allow further partitioning of these effects. For example, photosynthesis-linked fluxes due to surface-sediment located benthic flora (submerged aquatic vegetation and macroalgae) can be partitioned from those occurring in the benthic water column when using the solid plate to isolate sediment effects during Ambient Water Incubations. Essentially, all pathways: benthic respiration, benthic photosynthesis, water column respiration, and water column photosynthesis can all be inferred from the various permutations of sequential or simultaneous (i.e. multiple incubation chambers) platform 100 incubations.

In some embodiments, the true sediment flux may be determined by a transfer function/equation that employs the data values of the first measurement set associated with benthic flux incubation and the data values of the second measurement set associated with ambient water incubation. In some embodiments, the true sediment flux can be determined by a machine learning classifier using the measurements as inputs. Data values may be (i) raw values acquired from each incubation acquired per hour, calculated rates (e.g., not adjusted for volume or sediment surface area), or fluxes (i.e., normalized for sediment surface area).

Machine Learning. The machine learning features discussed above can be implemented using one or more artificial intelligence and machine learning operations. The term "artificial intelligence" can include any technique that enables one or more computing devices or comping systems (i.e., a machine) to mimic human intelligence. Artificial intelligence (AI) includes but is not limited to knowledge bases, machine learning, representation learning, and deep learning. The term "machine learning" is defined herein to be a subset of AI that enables a machine to acquire knowledge by extracting patterns from raw data. Machine learning techniques include, but are not limited to, logistic regression, support vector machines (SVMs), decision trees, Naïve Bayes classifiers, and artificial neural networks. The term "representation learning" is defined herein to be a subset of machine learning that enables a machine to automatically discover representations needed for feature detection, prediction, or classification from raw data. Representation learning techniques include, but are not limited to, autoencoders and embeddings. The term "deep learning" is defined herein to be a subset of machine learning that enables a machine to automatically discover representations needed for feature detection, prediction, classification, etc., using layers of processing. Deep learning techniques include but are not limited to artificial neural networks or multilayer perceptron (MLP).

Machine learning models include supervised, semi-supervised, and unsupervised learning models. In a supervised learning model, the model learns a function that maps an input (also known as feature or features) to an output (also known as target) during training with a labeled data set (or dataset). In an unsupervised learning model, the algorithm discovers patterns among data. In a semi-supervised model, the model learns a function that maps an input (also known as a feature or features) to an output (also known as a target) during training with both labeled and unlabeled data.

Neural Networks. An artificial neural network (ANN) is a computing system including a plurality of interconnected neurons (e.g., also referred to as "nodes"). This disclosure contemplates that the nodes can be implemented using a computing device (e.g., a processing unit and memory as described herein). The nodes can be arranged in a plurality of layers such as an input layer, an output layer, and optionally one or more hidden layers with different activation functions. An ANN having hidden layers can be referred to as a deep neural network or multilayer perceptron (MLP). Each node is connected to one or more other nodes in the ANN. For example, each layer is made of a plurality of nodes, where each node is connected to all nodes in the previous layer. The nodes in a given layer are not interconnected with one another, i.e., the nodes in a given layer function independently of one another. As used herein, nodes in the input layer receive data from outside of the ANN, nodes in the hidden layer(s) modify the data between the input and output layers, and nodes in the output layer provide the results. Each node is configured to receive an input, implement an activation function (e.g., binary step, linear, sigmoid, tanh, or rectified linear unit (ReLU), and provide an output in accordance with the activation function. Additionally, each node is associated with a respective weight. ANNs are trained with a dataset to maximize or minimize an objective function. In some implementations, the objective function is a cost function, which is a measure of the ANN's performance (e.g., error such as L1 or L2 loss) during training, and the training algorithm tunes the node weights and/or bias to minimize the cost function. This disclosure contemplates that any algorithm that finds the maximum or minimum of the objective function can be used for training the ANN. Training algorithms for ANNs include but are not limited to backpropagation. It should be understood that an ANN is provided only as an example machine learning model. This disclosure contemplates that the machine learning model can be any supervised learning model, semi-supervised learning model, or unsupervised learning model. Optionally, the machine learning model is a deep learning model. Machine learning models are known in the art and are therefore not described in further detail herein.

A convolutional neural network (CNN) is a type of deep neural network that has been applied, for example, to image analysis applications. Unlike traditional neural networks, each layer in a CNN has a plurality of nodes arranged in three dimensions (width, height, depth). CNNs can include different types of layers, e.g., convolutional, pooling, and fully-connected (also referred to herein as "dense") layers. A convolutional layer includes a set of filters and performs the bulk of the computations. A pooling layer is optionally inserted between convolutional layers to reduce the computational power and/or control overfitting (e.g., by downsampling). A fully-connected layer includes neurons, where each neuron is connected to all of the neurons in the previous layer. The layers are stacked similar to traditional neural networks. GCNNs are CNNs that have been adapted to work on structured datasets such as graphs.

Other Supervised Learning Models. A logistic regression (LR) classifier is a supervised classification model that uses the logistic function to predict the probability of a target, which can be used for classification. LR classifiers are trained with a data set (also referred to herein as a "dataset") to maximize or minimize an objective function, for example, a measure of the LR classifier's performance (e.g., error such as L1 or L2 loss), during training. This disclosure contemplates that any algorithm that finds the minimum of the cost function can be used. LR classifiers are known in the art and are therefore not described in further detail herein.

An Naïve Bayes' (NB) classifier is a supervised classification model that is based on Bayes' Theorem, which assumes independence among features (i.e., the presence of one feature in a class is unrelated to the presence of any other features). NB classifiers are trained with a data set by computing the conditional probability distribution of each feature given a label and applying Bayes' Theorem to compute the conditional probability distribution of a label given an observation. NB classifiers are known in the art and are therefore not described in further detail herein.

A k-NN classifier is an unsupervised classification model that classifies new data points based on similarity measures (e.g., distance functions). The k-NN classifiers are trained with a data set (also referred to herein as a "dataset") to maximize or minimize a measure of the k-NN classifier's performance during training. This disclosure contemplates any algorithm that finds the maximum or minimum. The k-NN classifiers are known in the art and are therefore not described in further detail herein.

A majority voting ensemble is a meta-classifier that combines a plurality of machine learning classifiers for classification via majority voting. In other words, the majority voting ensemble's final prediction (e.g., class label) is the one predicted most frequently by the member classification models. The majority voting ensembles are known in the art and are therefore not described in further detail herein.

Additional Data Product: Amendment performance. The platform 100 can monitor the performance of chemical, physical, or biological amendment or treatment to sediments for the purposes of achieving some environmental goal such as nutrient, contaminant, or carbon sequestration. Each sediment porthole can receive a different amendment, although some degree of replication is ideal. Thus, for a six-porthole embodiment there would be two controls and two sets of treatments. The data portal can track fluxes over time and can potentially subtract fluxes obtained from the control treatment incubations so that the relative efficacy (i.e. benefit or not) of amended treatments over the control can be revealed.

Experimental Results and Additional Examples

A study is being conducted to demonstrate the implementation of the CAROSEL platform. The platform is designed to be constructed for shallow water monitoring, which greatly lowers cost and simplifies material design, although the fundamental design and mechanism are not different for a deep version. The monitored analytes are selected for freshwater eutrophication monitoring and include phosphate, ammonium, conductivity, temperature, dissolved oxygen, and redox parameters measurable via Hg/Au electrochemistry ($O_{2.aq}$; hydrogen sulfide, $\Sigma H_2S$; dissolved ferrous iron, $Fe^{2+}$; and dissolved manganese (II), $Mn^{2+}$) [22] [23]. The prototype platform 100 with sensors (except for the ammonium sensor) is depicted in FIG. 5.

The reliable in situ sensors are readily available, and there is a strong global need for sediment nutrient and dissolved oxygen monitoring from lake and estuarine sediments subject to eutrophication. Fortuitously, intense sensor development is ongoing for environmental and wastewater monitoring, so new sensor options emerge routinely [24].

Discussion

The ocean is a current focal point of societal relevance with the growing recognition of the importance of the Blue Economy and the UN Ocean Decade [18]. Generally, there is a bias towards water column processes in contrast to sediments due to easier sampling access and a relative paucity of expertise, despite general recognition that sediments are critical controls of the geochemistry of natural waters. However, this paradigm is currently shifting given the increasing appreciation of ecosystem services along the entire terrestrial-aquatic continuum [19] and common convergent scientific themes between the ocean and soils (e.g., the National Science Foundation Signals in the Soil Program), including ensuring their sustainability, sensing technological development, wireless data transfer, big data analyses, etc. Sediment monitoring, and benthic fluxes in particular, are likely poised to become an important piece of the blue economy landscape with direct connections to restoration, aquaculture, and the provisioning of goods; climate regulation, carbon sequestration and ocean acidification; water quality and recreation; marine industry, and others (Table 5). Within this context, the invention is poised to become one of the first long-term sediment observation platforms designed to fit the emerging needs of applied lake, estuarine, and marine monitoring programs.

The four main customer bases for the platform may include: 1) regulatory agencies, 2) private enterprises for monitoring for regulatory purposes or improving products and efficiency, 3) ecosystem service quantification, and 4) maritime ocean-observing and awareness.

First, as examples, benthic fluxes may become a routine part of many agency-led monitoring programs (e.g., water management, and environmental protection) as part of eutrophication, hypoxia, and harmful algal bloom monitoring. Seagrass restoration programs may be interested in determining if transplantation has resulted in reducing benthic nutrient fluxes linked to eutrophication. Additionally, new offshore finish aquaculture facilities are mandated by the Environmental Protection Agency to monitor hydrogen sulfide production in downstream sediments. For the deep-sea mining industry, regulatory requirements are currently being implemented regarding the release of contaminants which could affect deep-sea water quality.

Second, for private enterprises, benthic fluxes can guide corporate decision-making to enhance the efficiency of profit-linked activities, for either regulatory monitoring or verification (e.g., for carbon or nutrient mitigation credits). An enterprise developing and optimizing carbon mitigation technologies for the carbon credit offsetting may seek to test the total $CO_2$ (carbonate system parameters) or dissolved organic carbon (DOC) leakage occurring from sediments as a function of various protocols in an effort to best optimize their strategies. For operational carbon mitigation efforts, these dissolved leakages can be subtracted from the particulate carbon being deposited to sediments (measured by some other technique) to derive an improved estimate of sediment-sequestered carbon. From the regulatory perspective, agencies have recently discussed how to regulate and monitor Carbon Capture and Storage (CCS) efforts that seek to inject carbon dioxide into defunct marine oil and gas reservoirs. Leaks of carbon dioxide in the form of benthic fluxes in nearby sediments could lead to ocean acidification in nearby regions. As another example, aquaculture facilities may seek to alter feeding practices to seek a certain balance of sediment nutrient inputs with allochthonous food additions, thus optimizing food costs while minimizing undesirable excess nutrient eutrophication.

Third, sediments are valuable for their contribution to ecosystem services. For example, greenhouse gas emissions and the quality of water used and returned to the environment are reported by corporations as part of Environmental and Social and Governance (ESG) criteria, with direct measurements or validation often holding more weight. Corporations with high ESG scores may be well-poised relative to market peers both from the perspective of attracting investors but also a larger customer base. Additionally, a new type of asset class called "Natural Asset Companies" aims to develop markets in which virtually any geographical entity (i.e., farms, state parks, etc.) can be incorporated and traded on the market with their value determined by their overall output of ecosystem services. While sediment-related services beyond those related to carbon sequestration or water purification are not explicitly and separately represented within ecosystem service frameworks, these are new concepts that are only gaining traction in the last few years. Potential customers would be those with a financial interest in the quality of the service output, e.g., consulting firms conducting the initial appraisals and routine monitoring or even organizations insuring the output.

Finally, a real-time understanding of oceanographic conditions is required for safe and effective underwater activities. For example, underwater visibility is affected by sediment fluxes of colored-dissolved organic matter, potentially creating challenges for recreational or naval diving operations.

To date, it is likely that the most scientifically or industrially useful benthic flux measurements for which a market already exists are for 1) nutrient flux monitoring for eutrophication/hypoxia/algae bloom monitoring for the protection of human and ecosystem health, 2) carbon credit offsets for sequestered greenhouse gases (total aqueous $CO_2$ and $CH_4$) and dissolved organic carbon (DOC), and 3) contaminant fluxes. The systems, methods, and devices described herein are inspired for use by work monitoring nutrients for the purpose of understanding harmful algal blooms in Lake Okeechobee (Florida), a system in which relatively high-frequency processes may drive geochemical dynamics. With respect to potential environments, benthic flux incubation chambers provide the most trustworthy and comprehensive data in lacustrine and coastal environments with more fine-grained, non-permeable sediments and minimal advective forcing. These sediments tend to be diffusion-dominated and exhibit high near-surface pore water concentration gradients that result in rapid equilibration of chamber waters with sediments. Advective influences are less important both with and without chamber presence, so long as the chamber mixing mechanism does not create pressure gradients (example embodiments employ a pump with a diffusor instead of a central stirrer for this reason [1]). These fine-grained environments tend to be the terrestrial or nearshore environments for which applied monitoring is needed and that example embodiments can be marketed (e.g., eutrophication and algae bloom monitoring). On the other hand, even deep-sea sediments are dominated by clay-sized particles, so example embodiments may be considered for use for deep-sea mining monitoring [20], for example. In contrast, more permeable, sandy, advectively-influenced sediments or those hosting bio-irrigation processes may still be probed with example embodiments, particularly if the target processes are those that dominate at the sediment-water interface and thus have fast exchange times, e.g., measurements of benthic productivity or respiration, alkalinity consumption, or mineral-mediated nutrient release processes [21].

Additional Discussion

In situ analyses of sedimentary environments has numerous advantages over other techniques, such as sediment coring and lab analysis. The main advantages include improved sampling resolution, cost savings on labor, and the reduction of sampling artifacts (i.e., changes to the natural system).

In the field of chemical oceanography, both direct chemical concentrations and material fluxes are the two most common types of measurements. Benthic flux chamber incubations are the most common in situ technique for measuring fluxes, i.e., exchanges of geochemical analytes between sediments and the overlying water column [1][2]. Essentially, this consists of isolating a parcel of water in contact with the sediments for a period of hours to days, followed by time-series measurements of the chamber contents. Fundamentally, this technique allows the concentration of sediment-derived analytes into a smaller confined volume, thus increasing their concentration to a level more easily detectable by analytical chemical techniques while limiting water column advective influences that would otherwise result in rapid dilution of the sediment-derived analytes entrained in the overlying water column.

Sediments are typically a sink for aqueous dissolved oxygen ($O_{2.aq}$) due to microbial respiration processes, so the $O_{2.aq}$ concentration in benthic chambers usually decreases over the course of 2 to 48 hours from that concentration at the beginning of the incubation. The concentration at the beginning of incubation should be approximately equivalent to that of the surrounding ambient waters so long as the chamber is sufficiently flushed, e.g., with the lid open when emplaced onto the sediments, prior to the lid closing and the incubation commending. Inorganic dissolved nutrients, such as phosphate ($\Sigma PO_4$) or ammonium ($NH_4^+$), are generated in sediments or bottom waters due mainly to the respiration-linked degradation of their respective organic precursor forms or mineral-mediated processes and can subsequently flux from sediments. Their concentration can typically increase in the chamber over time unless other processes are at play, such as their biological uptake, conversion to other nutrient forms (e.g., nitrite, $NO_2^-$; or nitrate, $NO_3^-$), or their partitioning onto solid phase minerals either in the surface sediment layer or in suspension inside the chamber. Each dissolved analyte's accumulation (or depletion) rate in an individual chamber (i.e., time-series concentration data) can be used to back-calculate the sediment area-normalized flux in units of moles or grams of $NH_4^+$ per day, for example.

Time-series measurements of the analytes of interest can be achieved directly in situ by the benthic lander platform if the appropriate sensor technology is available, equipped, and programmed to collect data at appropriate times. Alternatively, or in addition, samples can be collected as a function of time (e.g., hourly), typically with a programmable syringe system, for later lab analyses. The samples may also be filtered as they are being introduced, or a stabilizer/preservative can be preloaded into the syringes [3]. Conventionally, a selection of analytes measured in situ includes salinity, dissolved oxygen, pH, and turbidity, because existing commercially available sensors are available for monitoring these analytes in situ, whereas those most often measured upon return to the laboratory using collected samples may include nutrients or metabolites such as ammonium ($NH_4^+$), nitrate ($NO_3^-$), phosphate ($PO_4^{3-}$), dissolved silica (e.g., $H_4SiO_4$), dissolved inorganic carbon (DIC; a product of respiration), and contaminants. Typical logistics involve 1) the deployment of a benthic lander platform, 2) the gentle mixing of chamber contents via a mechanical stirrer or recirculating pump, 3) the start of the incubation via the mechanical closing of the chamber's lid, which is initially open to avoid trapping of air and water during descent to the seafloor and to provide a period for settling/equilibration, 4) the possible injection of a tracer or treatment compound to allow quantification of effective chamber size or physical mixing, to trace reactions, or to affect the biogeochemical processes, and 5) continuous or periodic monitoring and/or sampling until lander retrieval.

Most current benthic flux chamber incubations have been conducted for the purposes of fundamental monitoring, such as establishing oceanic carbon, dissolved oxygen, nutrient, or contaminant biogeochemical budgets. The major problem with current in situ benthic flux monitoring devices is the tendency to be research-grade, the requirement of expert operators, and the complicated logistics, often requiring a moderately-sized oceanographic research vessel. Currently, available benthic lander incubation seafloor platform systems are preparation- and labor-intensive and require several technicians a few hours to prepare, not including the initial lander reconstruction upon boarding a research vessel, which can take a day or more. Deployments are usually "one-off," generating only a single flux value per deployment (multiple chambers can be used simultaneously for redundancy but fluxes are typically averaged to ultimately still generate only a single time point measurement), and if multiple deployments are conducted in a region, it is typically to obtain better spatial characterization if part of a single cruise/campaign [4] or to obtain seasonal flux data at a few locations as part of a larger project [5]. Theoretically, the chamber lid could be opened (allowing re-equilibration with the ambient water) and then closed again to allow the restart of the next incubation, but the underlying sediment biogeochemistry would be fundamentally altered from the period that it was physically blocked from receiving natural sediment deposition, potentially resulting in serious artifacts. One issue that can arise due to work performed in deeper, less dynamic environments and due to technological limitations is that lander operators typically assume that changes in the incubated parcel of water are entirely due to sediment influence, with bottom water processes relatively negligible [2], despite acknowledging this is often not the case. This leads to flawed data interpretation, but current benthic lander systems are not capable of correcting ambient bottom water processes. For example, in shallow coastal systems, benthic harmful algal blooms (HABs) may limit the accumulation of sediment-derived nutrients in the benthic flux chamber due to simultaneous biological assimilative uptake, depressing the apparent sediment flux. Ideally, a device would also be capable of conducting ambient bottom water reference (i.e., control) incubations in order to account for the influence of ambient benthic water column processes and, thus, ultimately obtain a more accurate estimate of sediment-only processes.

Four main techniques are currently used to measure benthic fluxes: 1) sediment coring and measurement of the near-surface pore water gradient and calculation of fluxes using Fick's Law, 2) sediment core incubations and monitoring of the overlying water, 3) eddy covariance, 4) gradient flux techniques, and 5) benthic flux chambers. The first two techniques are not conducive to continuous measurement and are subject to artifacts associated with removing a sediment sample from the natural environment. Eddy covariance is a relatively new option and represents a potentially powerful technique for monitoring fluxes of solutes even in high permeability environments where benthic flux chambers may present problems (for example, in the case of sandy hydrodynamic sediments), as the system minimally interferes with and inherently incorporates advective influences. With eddy covariance, simultaneous measurements of both the analyte concentration and instantaneous vertical velocity are obtained at the exact same location immediately above the sediments, with their time-integrated multiplicative product yielding a time-resolved flux. However, the selection of potential monitoring analytes is limited to those that can be measured in situ with a response time at least as good as 2 Hz (<500 milliseconds) and can be measured at a single point in 3D space with a sensor that is small enough to not interfere with physical water transport processes at that exact location. Typically, only microelectrodes or optical measurements satisfy these criteria. Data interpretation is challenging and requires substantial validation [6]. To date, measurements have been limited to dissolved oxygen (measured most frequently), salinity, hydrogen sulfide, pH, and nitrate [7]. While the systems, methods, and devices disclosed herein still require an in-situ sensor for long-term deployment, the required minimum sensor response times are three to four orders of magnitude less (i.e., hours vs. split seconds), and virtually any sensor type (e.g., fluidic, electrochemical, optical) is possible. Gradient flux techniques, on the other hand, are an emerging technique within the aquatic science community that does allow for less frequent measurements and, thus, a theoretically greater selection of analytes. However, turbulence measurements must be carefully monitored or parameterized, and a significant gradient is required with respect to the analyte's concentration immediately above the sediment-water interface versus within approximately a meter above this interface [22].

The concept of in situ benthic flux chambers has been documented at least as early as with the use of "bell jar" incubations to measure community dissolved oxygen consumption [8]. The first modern landers with benthic flux chambers and sampling capabilities for the measurement of multiple analytes were developed in the 1980s [9][10], and many benthic landers equipped with flux incubation chambers have been described since, but the design has not fundamentally changed [11][12]. The number of commercially available benthic flux incubation chamber systems is limited, probably because most groups conducting this work are already established, and the cost and training required for a novice to pursue these measurements are not trivial. These include landers complete with a single benthic chamber and sample collection equipment available from Unisense® (MiniChamber Lander System™) or KC Denmark® (Benthic Flux Chamber™), or standalone chambers capable of accepting in situ sensors available from KC Denmark® (Benthic Flux Chamber™). Each of these existing systems conducts only a single incubation per deployment.

Numerous prior researchers have used in situ benthic flux monitoring devices to monitor aqueous sediments or have optimized chamber geometries and procedures. In an article written by A. Tengberg, et al. [11], fourteen different designs of chambers were analyzed, most of which are used in situ on landers. Measurements of mixing time, pressure gradients at the bottom, and diffusive boundary layer thickness were used to describe the hydrodynamic properties of the chambers and sediment.

In an example application, an article written by S. Sommer, et al. [12] discusses the use of benthic landers to measure benthic fluxes of dinitrogen gas, nitrate, nitrite, ammonium, hydrogen sulfide, and dissolved oxygen in marine environments. Flux measurements on the shelf were made under extreme geochemical conditions consisting of a lack of dissolved oxygen, nitrate, and nitrite in the bottom water and elevated seafloor hydrogen sulfide release.

The article written by John W. Morse, et al. [13] discusses an improved benthic chamber system that utilizes an artificial 'gill' to maintain close to ambient dissolved oxygen concentrations within the chamber. One issue with benthic incubation chambers is that sediment dissolved oxygen consumption, and thus the induction of anaerobic overlying waters now in contact with sediments, can affect benthic flux rates of other analytes due to complex geochemical processes (e.g., methane, hydrogens sulfide, and ammonium) [14]. This is problematic in the case of these types of analytes that have a long flux timescale relative to that of dissolved oxygen. While this "gill" system enables the measurement of benthic fluxes of analytes that require long periods of monitoring chamber contents to resolve, each deployment still only results in a single incubation concentration time series and, thus, a single discrete flux measurement.

The addition of a long (>1 meter), small gauge tubing extending from the chamber and open to the ambient bottom water has been previously employed to avoid pressure-related analytical artifacts. In the absence of this pressure equilibration tube, the removal of water from the chamber associated with sampling or analyses creates suction which can generally enhance the transport of sediment pore water analytes into the chamber. At the expense of slight dilution of the chamber contents with the external ambient water, the pressure equilibration tube can somewhat mitigate this issue.

The benthic flux chambers discussed above are all designed for single use and must be reset onboard a research vessel prior to redeployment. Each deployment usually has complex logistics and typically yields only a single flux measurement per analyte, thus precluding simultaneous spatial monitoring while requiring retrieval, resetting, and redeployment for time series flux measurements (i.e., researchers are limited to one or two deployments per day. Benthic flux chamber lids have been previously reopened during a singular, otherwise stationary deployment to "reset" the incubation or evaluate the effects of some other treatment/perturbation, such as the injection of a suspension into the chamber [25]. This could enable multiple incubation time series but also invites artifacts due to potential impacts on deposition and sediment biogeochemistry caused by the first incubation. In [25], the discussed system conducted an incubation with deliberate sediment resuspension as a follow-up to incubation with minimal stirring to examine the induced effects on dissolved oxygen and nutrient cycling.

Long-term chamber static incubations are available to the soil science community. For example, the Li-Cor® 8200 Smart Chamber™ enables monitoring repeat soil flux measurements of greenhouse gases with a single, static chamber. Soil dynamics, however, are 1) less subject to memory effects from enclosure relative to sediment dynamics, in which the induction of anoxia can cause dramatic biogeochemical changes in the latter, and 2) are less affected by new surface deposition as soils tend to instead form "from below" via interactions with pedogenetic processes and interactions with bedrock in contrast to sedimentation from above.

The development of a benthic lander platform capable of conducting repeated, benthic flux incubations to obtain long time series is thus motivated or enabled by the following: 1) the continuous observation of chamber contents is now possible via the emergence of a variety of in situ, robust sensors that can be equipped on the example platform and deployed long term; 2) the high cost of oceanographic research cruises and long transits to sites of interest may prohibit frequent deployment-retrieval cycles. While conventional discrete "one-off" benthic flux measurements (typically conducted seasonally at best) may be more acceptable in the ocean given generally less dynamic biogeochemical cycling than in estuaries, for example, the current technology still likely limits the characterization of many processes; 3) more specifically, the need for applied monitoring is now growing due to emerging environmental threats and markets; 4) continuous observation is necessary to capture the heterogeneity involved for many of these potential applications (Table 5); 5) the collection of infrequent benthic flux data is not useful to those outside of the scientific community, but outside interest is growing, for example with the use of greenhouse gas dynamics and fluxes as environmental social and governance (ESG) performance metrics; and 7) ocean observing technology development is set to be one of the most societally important themes in the 2020s with the rise of the blue economy, the United Nations Ocean Decade; however, in situ sediment monitoring activities and technologies are not yet widely appreciated, perhaps due to a lack of easy-to-use commercially available sediment-specific sensors and platforms. The overall scientific and public appreciation of sediments is growing, but sensing and platform technological innovation has lagged relative to sensors designed for the overlying water column.

TABLE 5

| Restoration & provisioning | |
| --- | --- |
| Sea vegetable aquaculture | Sediment growing conditions, including mineralogy. Fluxes are diagnostic and inform nutrient balance. Sulfide can be toxic. |
| Shellfish aquaculture & restoration | Fluxes are diagnostic of a healthy environment and indicate any toxins, e.g., sulfide. |
| Seagrass/mangrove restoration | Sediment growing conditions, including mineralogy. Fluxes are diagnostic and inform nutrient balance. Sulfide can be toxic. |
| Coral restoration | Adjacent sediments host accelerated carbon remineralization and nutrient fluxes that may contribute to reef support or decline. |
| Finfish stock health and aquaculture | Nutrient exchanges indirectly regulate fisheries by regulating submerged vegetation habitats, and aquaculture may have secondary effects on sediment quality. |
| Seaweed farming | Deliberate sedimentation of seaweed to bury carbon requires monitoring of the leakage fraction. |
| Ornamental resources | Sediment growing conditions. |
| Carbon and Ocean Acidification | |
| Trawling | Modifies sediment carbon sequestration and nutrient fluxes may slow or accelerate carbon degradation. |
| Blue carbon/CO2 sequestration | Accounting for burial requires quantification of leakage of both inorganic and organic carbon. |
| Climate prediction Geoengineering | Monitoring of greenhouse gas exchanges Pre- and post-site monitoring for predicted or actual efficacy |
| Alkalinity generation | Monitor the efficacy of deliberate strategies to mitigate ocean acidification based upon alkalization, such as enhanced rock weathering. |
| Water quality | |
| Legacy load monitoring (O2 vs. DIC flux) | Continuously monitor fluxes of nitrogen and phosphorous as part of eutrophication management programs. |
| Wastewater treatment | Monitor sediment nutrient fluxes in holding tanks. |
| Septic field efficacy | Monitor outflow fields of shorelines hosting septic tanks for nutrients. |
| N/P sequestration | Monitor the efficacy of natural or deliberate nutrient sequestration processes, e.g., dentrification rates |
| Sediment Oxygen Demand or hypoxia mitigation | Monitor sediment oxygen demand or natural, artificial, or oxygen regenerative systems. |
| Harmful Algal Bloom monitoring | Monitoring nutrient dynamics or toxin fluxes |
| Harmful Algal Bloom mitigation | Treatments to mitigate algae blooms may have secondary effects on sediments, e.g., nutrient flux enhancement feedbacks. |
| Underwater visibility | Colored material fluxes impede underwater visibility, e.g., for naval operations. |
| Recreation, | Colored material fluxes impede underwater |

TABLE 5-continued

| Driving, Tourism | visibility, e.g., for recreational fishing or diving. |
| --- | --- |
| Industry & Management | |
| Wind farms, Oil platforms, etc. | Affects carbon and nutrient cycling in the region and should be monitored. |
| Energy generation from Sediment Microbial Fuel Cells | Evaluate the energy-generating potential for deployment of sediment "bio-batteries." |
| Sulfide mitigation (corrosion & biological perspectives) | Hydrogen sulfide is strong toxicant and also a corrosion agent - relevance increasing with global deoxygenation and regional algae blooms |
| Hydrocarbon spill resilience | If a spill occurs, to what extent |
| Hydrocarbon exploration | Natural gas fluxes as indicators of deposits, e.g., methane fluxes |
| Deep sea mining ecosystem monitoring | Modifies sediment carbon sequestration and nutrient fluxes, may slow or accelerate carbon degradation. |
| Upstream land use, water transport management | Upstream land use decisions combined with water transport decisions (e.g., diversion) affect downstream sediment quality |
| Dredging/ Renourishment | Dredge sites or spoils can be a fertilizer resource but can also be a liability and leach sulfide, salt, and acid. |
| Island building | Consider sediment quality/fluxes pre- and post- construction. |
| Architectural site suitability | Examine corrosion potential, e.g., hydrogen sulfide fluxes, in regard to corrosion of pilings, pipelines, cables |
| Marine natural products (e.g., drug discovery) | Locate hotspots of biogeochemical activity based on flux signatures , e.g., for subsequent drug isolation/discovery efforts |
| Contaminant remediation | Directly measure organic or inorganic contaminants fluxing from sediments at waste disposal sites, adjacent to industry |
| Seafloor mapping | Incorporate sediment fluxes as critical portion of global ocean mapping projects. Relate benthic fluxes to substrate cover to aid extrapolation. |

Despite the foregoing developments, there is still a need for systems and methods for benthic flux monitoring devices for long-term applied monitoring of aqueous sediments.

While the systems, methods, and devices disclosed herein are, in some implementations, primarily envisioned for autonomous operation while deployed to the seafloor at a single location with data to be collected upon retrieval of the platform, other implementations are possible. For example, the system may be tethered to a surface buoy or fixed structure with remote communication capability to allow transmission of data to the operator in near-real time; 2) Fixed-location water column sensor suites are widely employed for environmental monitoring of water column conditions. Example implementations can be interfaced with these existing fixed-location sensor suites to augment the functionality and provide the capability to conduct benthic incubations and thus obtain benthic flux and ambient water column incubation measurements while still maintaining the ability to monitor ambient water column concentrations as originally intended, with data being transmitted to the operator in real-time. In this implementation, example systems do not necessarily require their own sensors onboard its platform as it instead utilizes existing sensor infrastructure; and 2) Autonomous environmental monitoring mobile platforms such as Autonomous Underwater Vehicles (AUVs) or Autonomous Surface Vehicles (ASVs) can periodically visit the example system to download the data, and periodically transmit the data to the operator via remote means such as satellite communications. This is especially useful if the example system is deployed at depths prohibiting direct tethering to surface communication infrastructure.

It should be appreciated that the logical operations for the data portal, data store, or user device interfacing therewith, described above can be implemented (1) as a sequence of computer-implemented acts or program modules running on a computing system and/or (2) as interconnected machine logic circuits or circuit modules within the computing system. The implementation is a matter of choice dependent on the performance and other requirements of the computing system. Accordingly, the logical operations described herein are referred to variously as state operations, acts, or modules. These operations, acts and/or modules can be implemented in software, in firmware, in special purpose digital logic, in hardware, and any combination thereof. It should also be appreciated that more or fewer operations can be performed than shown in the figures and described herein. These operations can also be performed in a different order than those described herein.

Various computing systems may be employed to implement the exemplary system and method described herein. The computing device may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computing device to provide the functionality of a number of servers that is not directly bound to the number of computers in the computing device. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or maybe hired on an as-needed basis from a third-party provider. Some cloud computing environments may comprise cloud computing resources owned and operated by the enterprise as well as cloud computing resources hired and/or leased from a third-party provider.

In its most basic configuration, a computing device typically includes at least one processing unit and system memory. Depending on the exact configuration and type of computing device, system memory may be volatile (such as random-access memory (RAM)), non-volatile (such as read-only memory (ROM), flash memory, etc.), or some combination of the two. The processing unit(s) may be a standard programmable processor that performs arithmetic and logic operations necessary for the operation of the computing device. As used herein, processing unit and processor refers to a physical hardware device that executes encoded instructions for performing functions on inputs and creating outputs, including, for example, but not limited to, microprocessors (MCUs), microcontrollers, graphical processing units (GPUs), and application-specific circuits (ASICs). Thus, while instructions may be discussed as executed by a processor, the instructions may be executed simultaneously, serially, or otherwise executed by one or multiple processors. The computing device 200 may also include a bus or other communication mechanism for communicating information among various components of the computing device.

The computing device may have additional features/functionality. For example, computing devices may include additional storage such as removable storage and non-removable storage including, but not limited to, magnetic or optical disks or tapes. The computing device may also contain network connection(s) that allow the device to communicate with other devices, such as over the communication pathways described herein. The network connection(s) may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. The computing device may also have input device(s) 270 such as keyboards, keypads, switches, dials, mice, trackballs, touch screens, voice recognizers, card readers, paper tape readers, or other well-known input devices. Output device(s) 260 such as printers, video monitors, liquid crystal displays (LCDs), touch screen displays, displays, speakers, etc., may also be included. The additional devices may be connected to the bus in order to facilitate the communication of data among the components of the computing device. All these devices are well known in the art and need not be discussed at length here.

The processing unit may be configured to execute program code encoded in tangible, computer-readable media. Tangible, computer-readable media refers to any media that is capable of providing data that causes the computing device (i.e., a machine) to operate in a particular fashion. Various computer-readable media may be utilized to provide instructions to the processing unit for execution. Example tangible, computer-readable media may include but is are not limited to volatile media, non-volatile media, removable media, and non-removable media implemented in any method or technology for storage of information such as computer-readable instructions, data structures, program modules, or other data. System memory 230, removable storage, and non-removable storage are all examples of tangible computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In light of the above, it should be appreciated that many types of physical transformations take place in the computer architecture in order to store and execute the software components presented herein. It also should be appreciated that the computer architecture may include other types of computing devices, including hand-held computers, embedded computer systems, personal digital assistants, and other types of computing devices known to those skilled in the art.

In an example implementation, the processing unit may execute program code stored in the system memory. For example, the bus may carry data to the system memory, from which the processing unit receives and executes instructions. The data received by the system memory may optionally be stored on the removable storage or the non-removable storage before or after execution by the processing unit.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high-level procedural or object-oriented programming language to communicate with a computer system. However, the program(s) can be implemented in assembly or machine language, if desired. In any case, the language may be a compiled or interpreted language, and it may be combined with hardware implementations.

It should be appreciated that any of the components or modules referred to with regards to any of the present embodiments discussed herein may be integrally or separately formed with one another. Further, redundant functions or structures of the components or modules may be implemented. Moreover, the various components may be communicated locally and/or remotely with any user/clinician/patient or machine/system/computer/processor.

Moreover, the various components may be in communication via wireless and/or hardwire or other desirable and available communication means, systems, and hardware. Moreover, various components and modules may be substituted with other modules or components that provide similar functions.

Although example embodiments of the present disclosure are explained in some instances in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an," and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the name compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g., 1 to 5 includes 1, 1.5, 2, 2.75, 3, 3.90, 4, 4.24, and 5).

Similarly, numerical ranges recited herein by endpoints include subranges subsumed within that range (e.g., 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

The following patents, applications, and publications, as listed below and throughout this document, are hereby incorporated by reference in their entirety herein.

[1] Tengberg, A., et al. (1995). "Benthic chamber and profiling landers in oceanography—A review of design, technical solutions and functioning." Progress in Oceanography 35(3): 253-294.
[2] Kononets, M., et al. (2021). "In situ incubations with the Gothenburg benthic chamber landers: Applications and quality control." Journal of Marine Systems 214: 103475.
[3] Orcutt, B. N. et al. (2017). "Microbial response to oil enrichment in Gulf of Mexico sediment measured using a novel long-term benthic lander system." Elementa: Science of the Anthropocene 5.
[4] Friedl, G., C. Dinkel and B. Wehrli (1998). "Benthic fluxes of nutrients in the northwestern Black Sea." Marine Chemistry 62(1-2): 77-88.
[5] Berelson, W., J. McManus, K. Coale, K. Johnson, D. Burdige, T. Kilgore, D. Colodner, F. Chavez, R. Kudela and J. Boucher (2003). "A time series of benthic flux measurements from Monterey Bay, CA." Continental Shelf Research 23(5): 457-481.
[6] Long, M. H. (2021). "Aquatic Biogeochemical Eddy Covariance Fluxes in the Presence of Waves." Journal of Geophysical Research: Oceans 126(2).
[7] Johnson, K. S., et al. (2011). "Nitrate and oxygen flux across the sediment-water interface observed by eddy correlation measurements on the open continental shelf." Limnology and Oceanography Methods 9(11):543-553.

[8] Pamatmat, M. M. and D. Fenton (1968). "AN INSTRU-MENT FOR MEASURING SUBTIDAL BENTHIC METABOLISM IN SITU 1." Limnology and Oceanography 13(3): 537-540.

[9] Berelson, W. M. and D. E. Hammond (1986). "The calibration of a new free-vehicle benthic flux chamber for use in the deep sea." Deep Sea Research Part A. Oceanographic Research Papers 33(10): 1439-1454.

[10] Jahnke, R. A. and M. B. Christiansen (1989). "A free-vehicle benthic chamber instrument for sea floor studies." Deep Sea Research Part A. Oceanographic Research Papers 36(4): 625-637.

[11] Tengberg, A., et al. (2005). "Intercalibration of benthic flux chambers." Marine Chemistry 94(1-4): 147-173.

[12] Sommer, et. al. (2016). "Depletion of oxygen, nitrate and nitrite in the Peruvian oxygen minimum zone cause an imbalance of benthic nitrogen fluxes." Deep Sea Research Part I: Oceanographic Research Papers 112: 113-122.

[13] Morse, J. W., G. Boland and G. T. Rowe (1999). "A 'gilled' benthic chamber for extended measurement of sediment-water fluxes." Marine Chemistry 66: 255-230.

[14] Sommer, S., M. Türk, S. Kriwanek and O. Pfannkuche (2008). "Gas exchange system for extended in situ benthic chamber flux measurements under controlled oxygen conditions: First application-Sea bed methane emission measurements at Captain Arutyunov mud volcano." Limnology and Oceanography: Methods 6(1): 23-33.

[15] Spagnoli, F., P. Penna, G. Giuliani, L. Masini and V. Martinotti (2019). "The AMERIGO Lander and the Automatic Benthic Chamber (CBA): Two New Instruments to Measure Benthic Fluxes of Dissolved Chemical Species." Sensors (Basel) 19 (11).

[16] Sayles, F. L. and W. H. Dickinson (1991). "The ROLAI2D lander: A benthic lander for the study of exchange across the sediment-water interface." Deep Sea Research Part A. Oceanographic Research Papers 38(5): 505-529.

[17] Nielsen, L. P. and R. N. Glud (1996). "Denitrification in a coastal sediment measured in situ by the nitrogen isotope pairing technique applied to a benthic flux camber." Marine Ecology Progress Series 137: 181-186.

[18] Jouffray, J.-B., R. Blasiak, A. V. Norstrom, H. Österblom and M. Nyström (2020). "The Blue Acceleration: The Trajectory of Human Expansion into the Ocean." One Earth 2(1): 43-54.

[19] Apitz, S. E. (2012). "Conceptualizing the role of sediment in sustaining ecosystem services: Sediment-ecosystem regional assessment (SEcoRA)." Sci Total Environ 415: 9-30.

[20] Haffert, L., M. Haeckel, H. de Stigter and F. Janssen (2020). "Assessing the temporal scale of deep sea mining impacts on sediment biogeochemistry." Biogeosciences 17(10): 2767-2789.

[21] Jahnke, R. A., J. R. Nelson, R. L. Marinelli and J. E. Eckman (2000). "Benthic flux of biogenic elements on the Southeastern US continental shelf: influence of pore water advective transport and benthic microalgae." Continental Shelf Research 20(1): 109-127.

[22] Glazer, B. T., A. G. Marsh, K. Stierhoff and G. W. Luther (2004). "The dynamic response of optical oxygen sensors and voltametric electrodes to temporal changes in dissolved oxygen concentrations." Analytica Chimica Acta 518(1-2): 93-100.

[23] Meiggs, D. and M. Taillefert (2011). "The effect of riverine discharge on biogeochemical processes in estuarine sediments." Limnology and Oceanography 56(5): 1797-1810.

[24] Mahmud, M. A. P., F. Ejeian, S. Azadi, M. Myers, B. Pejcic, R. Abbassi, A. Razmjou and M. Asadnia (2020). "Recent progress in sensing nitrate, nitrite, phosphate, and ammonium in aquatic environment." Chemosphere 259.

[25] Niemist ö, J., et al. Benthic fluxes of oxygen and inorganic nutrients in the archipelago of gulf of Finland, Baltic Sea—effects of sediment resuspension measured in situ. J. Sea Res. 135, 95-106, 2018.

[26] Coogan, J., Rheuban, J. E. and Long, M. H. (2022), Evaluating benthic flux measurements from a gradient flux system. Limnol Oceanogr Methods, 20: 222-232. https://doi.org/10.1002/lom3.10482.

[27] U.S. Pat. No. 7,856,899.

[28] U.S. Pat. No. 5,473,952.

What is claimed is:

1. A system for measuring benthic fluxes of dissolved analytes, the system comprising:

an isolation structure having a plurality of pre-defined benthic flux sampling regions, including a first sampling region and a second sampling region, wherein each of the plurality of pre-defined benthic flux sampling regions is defined by a set of isolation walls;

a sampling chamber movably coupled to the isolation structure to move among the plurality of pre-defined benthic flux sampling regions, including the first sampling region and the second sampling region, wherein the sampling chamber and a benthic flux sampling region define a sampling volume for a benthic flux measurement;

an actuator coupled to the isolation structure to move the sampling chamber among the plurality of pre-defined benthic flux sampling regions; and a sample collection mechanism or a set of one or more sensors for collecting or measuring the benthic flux, wherein the set of one or more sensors includes a first sensor and is operatively coupled to the sampling chamber.

2. The system of claim 1, wherein the first sensor is fixably mounted to the system, and wherein the sampling chamber includes a sampling port that is routed, via a fluidic cable, to the first sensor or the sample collection mechanism.

3. The system of claim 1, wherein the first sensor is fixably mounted to the sampling chamber, including a first sensor, and wherein a sensor head of the first sensor or an intake port is in direct contact with contents of the sampling chamber.

4. The system of claim 1, wherein the sampling chamber comprises a chamber body and a chamber lid configured, via an actuator, to move between an open configuration and a closed configuration.

5. The system of claim 1, wherein the first sampling region has a perimeter defined by a sampling hole in the isolation structure.

6. The system of claim 1, wherein each benthic flux sampling region of the isolation structure includes a downward facing rim along its perimeter.

7. The system of claim 1, wherein the first sensor includes an electrochemical, optical, or fluidic sensor.

8. The system of claim 7, wherein the set of one or more sensors further includes a second sensor comprising at least one of an optical sensor, a temperature sensor, an acoustic sensor, a light sensor, a pressure sensor, a pH sensor, an optode sensor, or a combination thereof.

9. The system of claim 1, wherein the isolation structure forms a circular array of the benthic flux sampling regions.

10. The system of claim 1, wherein the isolation structure forms a non-circular array of the benthic flux sampling regions.

11. The system of claim 1, further comprising:

a controller, the controller having computer-readable instruction stored thereon, wherein execution of the instruction by a processor causes the processor to perform a positioning operation of the system, a measuring operation of the system, and a storing operation of the system.

12. A method for measuring seafloor benthic flux, the method comprising:

placing a benthic flux sampling system at a seafloor, the benthic flux sampling system comprising:

an isolation structure having a plurality of pre-defined benthic flux sampling regions, including a first sampling region and a second sampling region, wherein each of the plurality of pre-defined benthic flux sampling regions is defined by a set of isolation walls;

a sampling chamber movably coupled to the isolation structure to relocate among the plurality of pre-defined benthic flux sampling regions, including the first sampling region and the second sampling region, wherein the sampling chamber and a benthic flux sampling region define a constant volume for a seafloor benthic flux measurement;

an actuator coupled to the isolation structure to move the sampling chamber among the plurality of pre-defined benthic flux sampling regions; and a set of one or more sensors for measuring the seafloor benthic flux, wherein the set of one or more sensors is operatively coupled to the sampling chamber;

positioning the sampling chamber at the first sampling region;

measuring the benthic flux at the first sampling region according to a first pre-defined measurement protocol during a pre-defined period and;

positioning the sampling chamber at the second sampling region;

measuring the benthic flux at the second sampling region according to a second pre-defined measurement protocol after the pre-defined period; and storing the measured benthic flux of the first sampling region and the second sampling region for analysis.

13. The method of claim 12, wherein the steps of positioning the sampling chamber at the first sampling region and measuring the benthic flux employ a motorized actuation that is guided by a controller.

14. The method of claim 12, wherein the step of measuring the benthic flux at the first sampling region is guided by a controller.

15. The method of claim 12, wherein the step of measuring the benthic flux occurs when the sampling chamber is in an open structure configuration and when the sampling chamber is later in a closed structure configuration.

16. The method of claim 12 further comprising:

measuring ambient water incubations contemporaneously with the measuring of the benthic flux, wherein the measured ambient water incubation is employed to adjust the measured benthic flux to a true benthic flux measurement.

17. The method of claim 16, wherein the ambient water incubations are measured in the sampling chamber prior to or after the benthic flux measurement.

18. The method of claim 16, wherein the ambient water incubations are measured in a second sampling chamber prior to, concurrent with, or after the benthic flux measurement.

19. The method of claim 12, wherein the sampling chamber is perturbed immediately prior to and/or during the step of measuring the benthic flux.

20. The method of claim 12 further comprising:

receiving, by a processor, data values of measurements acquired from sensors of benthic flux for a body of water, including a first measurement associated with benthic flux incubation and a second measurement associated with ambient water incubation;

determining, by the processor, a value for true sediment flux via a computing operator that combines the data values of the first measurement associated with benthic flux incubation with the data values of the second measurement associated with ambient water incubation, wherein the value for true sediment flux is made accessible for presentation in monitoring, assessment, or treatment of the body of water.

21. The method of claim 20, further comprising:

receiving, by the processor, data values of a third measurement associated with open chamber water column measurements; and determining, by a processor, a value for turnover time using the determined value for true sediment flux and the data values of the third measurements associated with open chamber water column measurements, wherein the value for turnover time is made accessible for presentation in the monitoring, assessment, or treatment of the body of water.

* * * * *